the recurrence of a latent Mtb infection.

(12) United States Patent
Shafferman et al.

(10) Patent No.: US 8,361,482 B2
(45) Date of Patent: Jan. 29, 2013

(54) **RECOMBINANT BCG TUBERCULOSIS VACCINE DESIGNED TO ELIC

A.

```
  1 mqlvdrvrga vtgmsrrlvv gavgaalvsg lvgavggtat agafsrpglp veylqvpsps
 61 mgrdikvqfq sgganspaly lldglraqdd fsgwdintpa fewydqsgls vvmpvggqss
121 fysdwyqpac gkagcqtykw etfltselpg wlqanrhvkp tgsavvglsm aassaltlai
181 yhpqqfvyag amsglldpsq amgptligla mgdaggykas dmwgpkedpa wqrndpllnv
241 gklianntrv wvycgngkps dlggnnlpak flegfvrtsn ikfqdaynag gghngvfdfp
301 dsgthsweyw gaqlnamkpd lqralgatpn tgpapqga
```

B.

```
ATGCAGCTTGTTGACAGGGTTCGTGGCGCCGTCACGGGTATGTCGCGTCGACTCGTGGTC
GGGGCCGTCGGCGCGGCCCTAGTGTCGGGTCTGGTCGGCGCCGTCGGTGGCACGGCGACC
GCGGGGGCATTTTCCCGGCCGGGCTTGCCGGTGGAGTACCTGCAGGTGCCGTCGCCGTCG
ATGGGCCGTGACATCAAGGTCCAATTCCAAAGTGGTGGTGCCAACTCGCCCGCCCTGTAC
CTGCTCGACGGCCTGCGCGCGCAGGACGACTTCAGCGGCTGGGACATCAACACCCCGGCG
TTCGAGTGGTACGACCAGTCGGGCCTGTCGGTGGTCATGCCGGTGGGTGGCCAGTCAAGC
TTCTACTCCGACTGGTACCAGCCCGCCTGCGGCAAGGCCGGTTGCCAGACTTACAAGTGG
GAGACCTTCCTGACCAGCGAGCTGCCGGGGTGGCTGCAGGCCAACAGGCACGTCAAGCCC
ACCGGAAGCGCCGTCGTCGGTCTTTCGATGGCTGCTTCTTCGGCGCTGACGCTGGCGATC
TATCACCCCAGCAGTTCGTCTACGCGGGAGCGATGTCGGGCCTGTTGGACCCCTCCCAG
GCGATGGGTCCCACCCTGATCGGCCTGGCGATGGGTGACGCTGGCGGCTACAAGGCCTCC
GACATGTGGGGCCCGAAGGAGGACCCGGCGTGGCAGCGCAACGACCCGCTGTTGAACGTC
GGGAAGCTGATCGCCAACAACACCCGCGTCTGGGTGTACTGCGGCAACGGCAAGCCGTCG
GATCTGGGTGGCAACAACCTGCCGGCCAAGTTCCTCGAGGGCTTCGTGCGGACCAGCAAC
ATCAAGTTCCAAGACGCCTACAACGCCGGTGGCGGCCACAACGGCGTGTTCGACTTCCCG
GACAGCGGTACGCACAGCTGGAGTACTGGGGCGCGCAGCTCAACGCTATGAAGCCCGAC
CTGCAACGGGCACTGGGTGCCACGCCCAACACCGGGCCCGCGCCCCAGGGCGCCTAG
```

Figure 5A and B

A.

```
  1 mtdvsrkira wgrrlmigta aavvlpglvg laggaataga fsrpglpvey lqvpspsmgr
 61 dikvqfqsgg nnspavylld glraqddyng wdintpafew yyqsglsivm pvggqssfys
121 dwyspacgka gcqtykwetf ltselpqwls anravkptgs aaiglsmags samilaayhp
181 qqfiyagsls alldpsqgmg psliglamgd aggykaadmw gpssdpawer ndptqqipkl
241 vanntrlwvy cgngtpnelg ganipaefle nfvrssnlkf qdaynaaggh navfnfppng
301 thsweywgaq lnamkgdlqs slgag
```

B.

```
ATGACAGACGTGAGCCGAAAGATTCGAGCTTGGGGACGCCGATTGATGATCGGCACGGCA
GCGGCTGTAGTCCTTCCGGGCCTGGTGGGGCTTGCCGGCGGAGCGGCAACCGCGGGCGCG
TTCTCCCGGCCGGGGCTGCCGGTCGAGTACCTGCAGGTGCCGTCGCCGTCGATGGGCCGC
GACATCAAGGTTCAGTTCCAGAGCGGTGGGAACAACTCACCTGCGGTTTATCTGCTCGAC
GGCCTGCGCGCCCAAGACGACTACAACGGCTGGGATATCAACACCCCGGCGTTCGAGTGG
TACTACCAGTCGGGACTGTCGATAGTCATGCCGGTCGGCGGGCAGTCCAGCTTCTACAGC
GACTGGTACAGCCCGGCCTGCGGTAAGGCTGGCTGCCAGACTTACAAGTGGGAAACCTTC
CTGACCAGCGAGCTGCCGCAATGGTTGTCCGCCAACAGGGCCGTGAAGCCCACCGGCAGC
GCTGCAATCGGCTTGTCGATGGCCGGCTCGTCGGCAATGATCTTGGCCGCCTACCACCCC
CAGCAGTTCATCTACGCCGGCTCGCTGTCGGCCCTGCTGGACCCCTCTCAGGGGATGGGG
CCTAGCCTGATCGGCCTCGCGATGGGTGACGCCGGCGGTTACAAGGCCGCAGACATGTGG
GGTCCCTCGAGTGACCCGGCATGGGAGCGCAACGACCCTACGCAGCAGATCCCCAAGCTG
GTCGCAAACAACACCCGGCTATGGGTTTATTGCGGGAACGGCACCCCGAACGAGTTGGGC
GGTGCCAACATACCCGCCGAGTTCTTGGAGAACTTCGTTCGTAGCAGCAACCTGAAGTTC
CAGGATGCGTACAACGCCGCGGGCGGGCACAACGCCGTGTTCAACTTCCCGCCCAACGGC
ACGCACAGCTGGGAGTACTGGGGCGCTCAGCTCAACGCCATGAAGGGTGACCTGCAGAGT
TCGTTAGGCGCCGGCTGA
```

Figure 6A and B

A

```
  1 msgrhrkptt snvsvakiaf tgavlggggi amaaqataat dgewdqvarc esggnwsint
 61 gngylgglqf tqstwaahgg gefapsaqla sreqqiavge rvlatqgrga wpvcgrglsn
121 atprevlpas aamdapldaa avngepapla pppadpappv elaandlpap lgeplpaapa
181 dpappadlap papadvappv elavndlpap lgeplpaapa dpappadlap papadlappa
241 padlappapa dlappvelav ndlpaplgep lpaapaelap padlapasad lappapadla
301 ppapaelapp apadlappaa vneqtapgdq patapggpvg latdlelpep dpqpadappp
361 gdvteapaet pqvsniaytk klwqairaqd vcgndaldsl aqpyvig
```

B

```
ATGAGTGGACGCCACCGTAAGCCCACCACATCCAACGTCAGCGTCGCCAAGATCGCC
TTTACCGGCGCAGTACTCGGTGGCGGCGGCATCGCCATGGCCGCTCAGGCGACCGCG
GCCACCGACGGGGAATGGGATCAGGTGGCCCGCTGCGAGTCGGGCGGCAACTGGTCG
ATCAACACCGGCAACGGTTACCTCGGTGGCTTGCAGTTCACTCAAAGCACCTGGGCC
GCACATGGTGGCGGCGAGTTCGCCCCGTCGGCTCAGCTGGCCAGCCGGGAGCAGCAG
ATTGCCGTCGGTGAGCGGGTGCTGGCCACCCAGGGTCGCGGCGCCTGGCCGGTGTGC
GGCCGCGGGTTATCGAACGCAACACCCCGCGAAGTGCTTCCCGCTTCGGCAGCGATG
GACGCTCCGTTGGACGCGGCCGCGGTCAACGGCGAACCAGCACCGCTGGCCCCGCCG
CCCGCCGACCCGGCGCCACCCGTGGAACTTGCCGCTAACGACCTGCCCGCACCGCTG
GGTGAACCCCTCCCGGCAGCTCCCGCCGACCCGGCACCACCCGCCGACCTGGCACCA
CCCGCGCCCGCCGACGTCGCGCCACCCGTGGAACTTGCCGTAAACGACCTGCCCGCA
CCGCTGGGTGAACCCCTCCCGGCAGCTCCCGCCGACCCGGCACCACCCGCCGACCTG
GCACCACCCGCGCCCGCCGACCTGGCGCCACCCGCGCCCGCCGACCTGGCGCCACCC
GCGCCCGCCGACCTGGCACCACCCGTGGAACTTGCCGTAAACGACCTGCCCGCGCCG
CTGGGTGAACCCCTCCCGGCAGCTCCCGCCGAACTGGCGCCACCCGCCGATCTGGCA
CCCGCGTCCGCCGACCTGGCGCCACCCGCGCCCGCCGACCTGGCGCCACCCGCGCCC
GCCGAACTGGCGCCACCCGCGCCCGCCGACCTGGCACCACCCGCTGCGGTGAACGAG
CAAACCGCGCCGGGCGATCAGCCCGCCACAGCTCCAGGCGGCCCGGTTGGCCTTGCC
ACCGATTTGGAACTCCCCGAGCCCGACCCCCAACCAGCTGACGCACCGCCGCCCGGC
GACGTCACCGAGGCGCCCGCCGAAACGCCCCAAGTCTCGAACATCGCCTATACGAAG
AAGCTGTGGCAGGCGATTCGGGCCCAGGACGTCTGCGGCAACGATGCGCTGGACTCG
CTCGCACAGCCGTACGTCATCGGCTGA
```

Figure 7A and B

A mlrlvvgall lvlafaggya vaacktvtlt vdgtamrvtt mksrvidive
engfsvddrd dlypaagvqv hdadtivlrr srplqisldg hdakqvwtta
stvdealaql amtdtapaaa srasrvplsg malpvvsakt vqlndgglvr
tvhlpapnva gllsaagvpl lqsdhvvpaa tapivegmqi qvtrnrikkv
terlplppna rrvedpemnm srevvedpgv pgtqdvtfav aevngvetgr
lpvanvvvtp aheavvrvgt kpgtevppvi dgsiwdaiag ceaggnwain
tgngyyggvq fdqgtweang glryapradl atreeqiava evtrlrqgwg
awpvcaarag ar

B atgttgcgcc tggtagtcgg tgcgctgctg ctggtgttgg cgttcgccgg
tggctatgcg gtcgccgcat gcaaaacggt gacgttgacc gtcgacggaa
ccgcgatgcg ggtgaccacg atgaaatcgc gggtgatcga catcgtcgaa
gagaacgggt tctcagtcga cgaccgcgac gacctgtatc ccgcggccgg
cgtgcaggtc catgacgccg acaccatcgt gctgcggcgt agccgtccgc
tgcagatctc gctggatggt cacgacgcta agcaggtgtg gacgaccgcg
tcgacggtgg acgaggcgct ggcccaactc gcgatgaccg acacggcgcc
ggccgcggct tctcgcgcca gccgcgtccc gctgtccggg atggcgctac
cggtcgtcag cgccaagacg gtgcagctca acgacggcgg gttggtgcgc
acggtgcact tgccggcccc caatgtcgcg gggctgctga gtgcggccgg
cgtgccgctg ttgcaaagcg accacgtggt gcccgccgcg acggccccga
tcgtcgaagg catgcagatc caggtgaccc gcaatcggat caagaaggtc
accgagcggc tgccgctgcc gccgaacgcg cgtcgtgtcg aggacccgga
gatgaacatg agccgggagg tcgtcgaaga cccgggggtt ccggggaccc
aggatgtgac gttcgcggta gctgaggtca acggcgtcga gaccggccgt
ttgcccgtcg ccaacgtcgt ggtgaccccg gcccacgaag ccgtggtgcg
ggtgggcacc aagcccggta ccgaggtgcc cccggtgatc gacggaagca
tctgggacgc gatcgccggc tgtgaggccg gtggcaactg gcgatcaac
accggcaacg ggtattacgg tggtgtgcag tttgaccagg gcacctggga
ggccaacggc gggctgcggt atgcaccccg cgctgacctc gccacccgcg
aagagcagat cgccgttgcc gaggtgaccc gactgcgtca aggttggggc
gcctggccgg tatgtgctgc acgagcgggt
gcgcgctga

Figure 8A and B

A.

```
mhplpadhgr srcnrhpisp lslignasat sgdmssmtri akpliksama
aglvtasmsl stavahagps pnwdavaqce sggnwaantg ngkygglqfk
patwaafggv gnpaaasreq qiavanrvla eqgldawptc gaasglpial
wskpaqgikq iineiiwagi qasipr
```

B.

```
GTGCATCCTTTGCCGGCCGACCACGGCCGGTCGCGGTGCAATAGACAC
CCGATCTCACCACTCTCTCTAATCGGTAACGCTTCGGCCACTTCCGGCG
ATATGTCGAGCATGACAAGAATCGCCAAGCCGCTCATCAAGTCCGCCA
TGGCCGCAGGACTCGTCACGGCATCCATGTCGCTCTCCACCGCCGTTG
CCCACGCCGGTCCCAGCCCGAACTGGGACGCCGTCGCGCAGTGCGAA
TCCGGGGGCAACTGGGCGGCCAACACCGGAAACGGCAAATACGGCGG
ACTGCAGTTCAAGCCGGCCACCTGGGCCGCATTCGGCGGTGTCGGCAA
CCCAGCAGCTGCCTCTCGGGAACAACAAATCGCAGTTGCCAATCGGGT
TCTCGCCGAACAGGGATTGGACGCGTGGCCGACGTGCGGCGCCGCCTC
TGGCCTTCCGATCGCACTGTGGTCGAAACCCGCGCAGGGCATCAAGCA
AATCATCAACGAGATCATTTGGGCAGGCATTCAGGCAAGTATTCCGCG
CTGA
```

Figure 9A and B

A.

mtpgllttag agrprdrcar ivctvfieta vvatmfvall glstisskad
didwdaiaqc esggnwaant gnglygglqi sqatwdsngg vgspaaaspq
qqievadnim ktqgpgawpk csscsqgdap lgslthiltf laaetggcsg srdd

B.

ATGACACCGGGTTTGCTTACTACTGCGGGTGCTGGCCGACCACGTGAC
    AGGTGCGCCAGGATCGTATGCACGGTGTTCATCGAAACCGCCGTTGTC
    GCGACCATGTTTGTCGCGTTGTTGGGTCTGTCCACCATCAGCTCGAAA
    GCCGACGACATCGATTGGGACGCCATCGCGCAATGCGAATCCGGCGG
    CAATTGGGCGGCCAACACCGGTAACGGGTTATACGGTGGTCTGCAGAT
    CAGCCAGGCGACGTGGGATTCCAACGGTGGTGTCGGGTCGCCGGCGG
    CCGCGAGTCCCCAGCAACAGATCGAGGTCGCAGACAACATTATGAAA
    ACCCAAGGCCCGGGTGCGTGGCCGAAATGTAGTTCTTGTAGTCAGGGA
    GACGCACCGCTGGGCTCGCTCACCCACATCCTGACGTTCCTCGCGGCC
    GAGACTGGAGGTTGTTCGGGGAGCAGGGACGATTGA

Figure 10A and B

A.

```
mknarttlia aaiagtlvtt spagianadd agldpnaaag pdavgfdpnl
ppapdaapvd tppapedagf dpnlppplap dflsppaeea ppvpvaysvn
wdaiaqcesg gnwsintgng yygglrftag twranggsgs aanasreeqi
rvaenvlrsq girawpvcgr rg
```

B.

```
TTGAAGAACGCCCGTACGACGCTCATCGCCGCCGCGATTGCCGGGACG
TTGGTGACCACGTCACCAGCCGGTATCGCCAATGCCGACGACGCGGGC
TTGGACCCAAACGCCGCAGCCGGCCCGGATGCCGTGGGCTTTGACCCG
AACCTGCCGCCGGCCCCGGACGCTGCACCCGTCGATACTCCGCCGGCT
CCGGAGGACGCGGGCTTTGATCCCAACCTCCCCCCGCCGCTGGCCCCG
GACTTCCTGTCCCCGCCTGCGGAGGAAGCGCCTCCCGTGCCCGTGGCC
TACAGCGTGAACTGGGACGCGATCGCGCAGTGCGAGTCCGGTGGAAA
CTGGTCGATCAACACCGGTAACGGTTACTACGGCGGCCTGCGGTTCAC
CGCCGGCACCTGGCGTGCCAACGGTGGCTCGGGGTCCGCGGCCAACG
CGAGCCGGGAGGAGCAGATCCGGGTGGCTGAGAACGTGCTGCGTTCG
CAGGGTATCCGCGCCTGGCCGGTCTGCGGCCGCCGCGGCTGA
```

Figure 11A and B

A.

```
mssgnsslgi ivgiddspaa qvavrwaard aelrkipltl vhavspevat
wlevplppgv lrwqqdhgrh liddalkvve qaslragppt vhseivpaaa
vptlvdmskd avlmvvgclg sgrwpgrllg svssgllrha hcpvviihde
dsvmphpqqa pvlvgvdgss aselataiaf deasrrnvdl valhawsdvd
vsewpgidwp atqsmaeqvl aerlagwqer ypnvaitrvv vrdqparqlv
qrseeaqlvv vgsrgrggya gmlvgsvget vaqlartpvi vareslt
```

B.

```
atgtcatcgg gcaattcatc tctgggaatt atcgtcggga tcgacgattc
accggccgca caggttgcgg tgcggtgggc agctcgggat gcggagttgc
gaaaaatccc tctgacgctc gtgcacgcgg tgtcgccgga agtagccacc
tggctggagg tgccactgcc gccgggcgtg ctgcgatggc agcaggatca
cgggcgccac ctgatcgacg acgcactcaa ggtggttgaa caggcttcgc
tgcgcgctgg tccccccacg gtccacagtg aaatcgttcc ggcggcagcc
gttcccacat tggtcgacat gtccaaagac gcagtgctga tggtcgtggg
ttgtctcgga agtgggcggt ggccgggccg gctgctcggt tcggtcagtt
ccggcctgct ccgccacgcg cactgtccgg tcgtgatcat ccacgacgaa
gattcggtga tgccgcatcc ccagcaagcg ccggtgctag ttggcgttga
cggctcgtcg gcctccgagc tggcgaccgc aatcgcattc gacgaagcgt
cgcggcgaaa cgtggacctg gtggcgctgc acgcatggag cgacgtcgat
gtgtcggagt ggcccggaat cgattggccg gcaactcagt cgatggccga
gcaggtgctg gccgagcggt tggcgggttg gcaggagcgg tatcccaacg
tagccataac ccgcgtggtg gtgcgcgatc agccggcccg ccagtcgtc
caacgctccg aggaagccca gctggtcgtg gtcggcagcc ggggccgcgg
cggctacgcc ggaatgctgg tggggtcggt aggcgaaacc gttgctcagc
tggcgcggac gccggtcatc gtggcacgcg agtcgctgac ttag
```

Figure 12A and B

A.

msqimynypa mlghagdmag yagtlqslga eiaveqaalq sawqgdtgit
yqawqaqwnq amedlvrayh amsstheant mammardtae aakwgg

B.

atgtcgcaaa tcatgtacaa ctaccccgcg atgttgggtc acgccgggga
tatggccgga tatgccggca cgctgcagag cttgggtgcc gagatcgccg
tggagcaggc cgcgttgcag agtgcgtggc agggcgatac cgggatcacg
tatcaggcgt ggcaggcaca gtggaaccag gccatggaag atttggtgcg
ggcctatcat gcgatgtcca gcacccatga agccaacacc atggcgatga
tggcccgcga cacggccgaa gccgccaaat ggggcggcta g

Figure 13A and B

A.

```
mttardimna gvtcvgehet ltaaaqymre hdigalpicg dddrlhgmlt
drdivikgla agldpntata gelardsiyy vdanasiqem lnvmeehqvr
rvpvisehrl vgivteadia rhlpehaivq fvkaicspma las
```

B.

```
ATGACCACCGCACGCGACATCATGAACGCAGGTGTGACCTGTGTTGGC
GAACACGAGACGCTAACCGCTGCCGCTCAATACATGCGTGAGCACGA
CATCGGCGCGTTGCCGATCTGCGGGGACGACGACCGGCTGCACGGCA
TGCTCACCGACCGCGACATTGTGATCAAAGGCCTGGCTGCGGGCCTAG
ACCCGAATACCGCCACGGCTGGCGAGTTGGCCCGGGACAGCATCTACT
ACGTCGATGCGAACGCAAGCATCCAGGAGATGCTCAACGTCATGGAA
GAACATCAGGTCCGCCGTGTTCCGGTCATCTCAGAGCACCGCTTGGTC
GGAATCGTCACCGAAGCCGACATCGCCCGACACCTGCCCGAGCACGC
CATTGTGCAGTTCGTCAAGGCAATCTGCTCGCCCATGGCCCTCGCCAG
CTAG
```

Figure 14A and B

A.

```
mskprkqhgv vvgvdgsles daaacwgatd aamrnipltv vhvvnadvat
wppmpypetw gvwqedegrq ivanavklak eavgadrkls vkselvfstp
vptmveisne aemvvlgssg rgalargllg svssslvrra gcpvavihsd
davipdpqha pvlvgidgsp vselatavaf deasrrgvel iavhawsdve
vvelpgldfs avqqeaelsl aerlagwqer ypdvpvsrvv vcdrparklv
qksasaqlvv vgshgrgglt gmllgsvsna vlhaarvpvi varqs
```

B.

```
ATGTCTAAACCCCGCAAGCAGCACGGAGTTGTCGTCGGGGTAGATGGTTCGC
TCGAATCGGATGCCGCCGCCTGTTGGGGTGCCACCGATGCGGCGATGAGGAA
CATTCCGCTGACCGTGGTCCACGTGGTGAACGCCGATGTAGCGACGTGGCCG
CCGATGCCGTATCCGGAGACCTGGGGGGTTTGGCAGGAGGACGAGGGTCGCC
AGATCGTCGCCAACGCCGTCAAGCTCGCCAAAGAGGCGGTTGGAGCGGATCG
AAAGCTCAGCGTAAAGAGCGAGCTCGTATTTTCCACGCCGGTACCTACCATG
GTTGAAATCTCCAACGAGGCAGAGATGGTGGTGTTGGGCAGCTCGGGCCGGG
GAGCGCTGGCCCCGAGGCTTGCTCGGTTCGGTCAGCTCGAGCCTGGTGCGACG
CGCCGGGTGCCCGGTCGCGGTCATCCACAGCGATGATGCGGTGATCCCTGAT
CCGCAGCACGCTCCCGTGCTGGTGGGAATCGACGGTTCGCCGGTTTCGGAGC
TTGCGACGGCGGTGGCATTTGACGAGGCGTCGCGCCGCGGCGTCGAACTGAT
CGCCGTGCACGCGTGGAGTGACGTCGAAGTGGTGGAACTTCCGGGTTTGGAC
TTCTCGGCTGTACAGCAGGAAGCGGAGCTTAGTCTCGCCGAACGCTTGGCAG
GTTGGCAAGAACGCTATCCCGATGTGCCGGTGAGCCGGGTTGTCGTTTGCGA
TCGCCCGGCGCGGAAGCTGGTGCAAAAGTCGGCGTCCGCCCAGCTTGTCGTC
GTTGGCAGTCATGGCCGAGGTGGCTTGACCGGCATGCTTCTGGGGTCGGTCA
GTAACGCGGTCTTACACGCCGCGCGGGTGCCAGTGATCGTGGCACGGCAGTC
GTGA
```

Figure 15A and B

A.

```
msaqqtnlgi vvgvdgspcs htavewaard aqmrnvalrv vqvvppvita
pegwafeysr fqeaqkreiv ehsylvaqah qiveqahkva leasssgraa
qitgevlhgq ivptlanisr qvamvvlgyr gqgavagall gsvsssslvrh
ahgpvavipe eprparppha pvvvgidgsp tsglaaeiaf deasrrgvdl
valhawsdmg pldfprlnwa piewrnlede qekmlarrls gwqdrypdvv
vhkvvvcdrp aprllelaqt aqlvvvgshg rggfpgmhlg svsravvnsg
qapvivarip qdpavpa
```

B.

```
atgtcagccc aacaaacgaa cctcggaatc gtggtcggtg tggatggttc
accctgctcg catacggcag tcgaatgggc cgcgcgcgat gcgcagatgc
gcaacgttgc gctccgcgtg gtgcaggtcg tgccccggt aataaccgcc
ccggaagggt gggcatttga gtattcgcgg tttcaagaag cccaaaagcg
cgaaatcgtc gaacactcgt acctgtcgc ccaagcgcac caaatcgtcg
aacaggccca caaggtcgcc ctcgaggcat cctcctcagg tcgcgccgcg
caaatcaccg gcgaagtgct gcacggccag atagtgccca cgctggccaa
catctccagg caggtcgcga tggtcgtgct gggctaccga ggtcagggcg
ccgtagccgg cgccttgctg ggatcggtca gctcaagcct ggttcgccac
gctcatggcc ctgtcgccgt aatacccgag gagccgcgac cggcgcgccc
gccgcacgcg ccggttgtgg tgggcatcga cggctcgccc acctcgggat
tggcggccga gatcgccttc gacgaggcat cgcgccgcgg cgtggacttg
gtggcgctgc acgcgtggag cgacatgggc cccctcgact ttcctaggct
caattgggcg ccgatcgaat ggagaaacct cgaagacgag caggagaaaa
tgctcgcccg gcgtctgagc ggatggcaag accggtatcc cgatgtcgtc
gtgcacaaag tcgtggtgtg cgatcgaccg gcaccccgcc tgctcgaatt
ggcacaaacc gctcagcttg tggtggttgg cagccacggc cgcggggggt
tccccggcat gcatctcggc tcagtcagca gagcggtggt caattccggt
caggctccgg ttatcgtcgc ccgaatcccc caagatccgg cagtgccggc
ctga
```

Figure 16A and B

A.

```
makakfqrtk phvnigtigh vdhgkttlta aitkvlhdkf pdlnetkafd
qidnapeerq rgitiniahv eyqtdkrhya hvdapghady iknmitgaaq
mdgailvvaa tdgpmpqtre hvllarqvgv pyilvalnka davddeelle
lvemevrell aaqefdedap vvrvsalkal egdakwvasv eelmnavdes
ipdpvretdk pflmpvedvf titgrgtvvt grvergvinv neeveivgir
psttkttvtg vemfrklldq gqagdnvgll lrgvkredve rgqvvtkpgt
ttphtefegq vyilskdegg rhtpffnnyr pqfyfrttdv tgvvtlpegt
emvmpgdntn isvkliqpva mdeglrfair eggrtvgagr vtkiik
```

B.

```
gtggcgaagg cgaagttcca gcggaccaag ccccacgtca acatcgggac
catcggtcac gttgaccacg gcaagaccac cctgaccgcg gctatcacca
aggtcctgca cgacaaattc cccgatctga acgagacgaa ggcattcgac
cagatcgaca acgccccga ggagcgtcag cgcggtatca ccatcaacat
cgcgcacgtg gagtaccaga ccgacaagcg cactacgca cacgtcgacg
ccctggcca cgccgactac atcaagaaca tgatcaccgg cgccgcgcag
atggacggtg cgatcctggt ggtcgccgcc accgacggcc cgatgcccca
gacccgcgag cacgttctgc tggcgcgtca agtgggtgtg ccctacatcc
tggtagcgct gaacaaggcc gacgcagtgg acgacgagga gctgctcgaa
ctcgtcgaga tggaggtccg cgagctgctg gctgcccagg aattcgacga
ggacgccccg gttgtgcggg tctcggcgct caaggcgctc gagggtgacg
cgaagtgggt tgcctctgtc gaggaactga tgaacgcggt cgacgagtcg
attccggacc cggtccgcga gaccgacaag ccgttcctga tgccggtcga
ggacgtcttc accattaccg gccgcggaac cgtggtcacc ggacgtgtgg
agcgcggcgt gatcaacgtg aacgaggaag ttgagatcgt cggcattcgc
ccatcgacca ccaagaccac cgtcaccggt gtggagatgt tccgcaagct
gctcgaccag ggccaggcgg cgacaacgt tggtttgctg ctgcggggcg
tcaagcgcga ggacgtcgag cgtggccagg ttgtcaccaa gcccggcacc
accacgccgc acccgagtt cgaaggccag gtctacatcc tgtccaagga
cgagggcggc cggcacacgc cgttcttcaa caactaccgt ccgcagttct
acttccgcac caccgacgtg accggtgtgg tgacactgcc ggagggcacc
gagatggtga tgcccggtga caacaccaac atctcggtga agttgatcca
gcccgtcgcc atggacgaag gtctgcgttt cgcgatccgc gagggtggcc
gcaccgtggg cgccggccgg gtcaccaaga tcatcaagta g
```

Figure 17A and B

A.

```
msakltdlql lhelepvvek ylnrhlsmhk pwnphdyipw sdgknyyalg
gqdwdpdqsk lsdvaqvamv qnlvtednlp syhreiamnm gmdgawgqwv
nrwtaeenrh gialrdylvv trsvdpvele klrlevvnrg fspgqnhqgh
yfaesltdsv lyvsfqelat rishrntgka cndpvadqlm akisadenlh
mifyrdvsea afdlvpnqam kslhlilshf qmpgfqvpef rrkavviavg
gvydprihld evvmpvlkkw riferedftg egaklrdela lvikdlelac
dkfevskqrq ldreartgkk vsahelhkta gklamsrr
```

B.

```
ATGTCAGCCAAGCTGACCGACCTGCAGCTGCTGCACGAACTTGAACCG
GTCGTCGAGAAGTACCTGAACCGGCACCTGAGCATGCACAAGCCCTG
GAACCCGCACGACTACATCCCGTGGTCGGACGGGAAGAACTACTACG
CGCTCGGCGGGCAGGATTGGGACCCCGACCAGAGCAAGCTTTCTGAT
GTCGCCCAGGTGGCGATGGTGCAGAACCTGGTCACCGAGGACAACCT
GCCGTCGTATCACCGCGAGATCGCGATGAACATGGGCATGGACGGCG
CGTGGGGGCAGTGGGTCAACCGTTGGACCGCCGAGGAGAATCGGCAC
GGCATCGCGCTGCGCGACTACCTGGTGGTGACCCGATCGGTCGACCCT
GTCGAGTTGGAGAAACTTCGCCTCGAGGTAGTCAACCGGGGCTTCAGC
CCAGGCCAAAACCACCAGGGCCACTATTTCGCGGAGAGCCTCACCGA
CTCCGTCCTCTATGTCAGTTTCCAGGAACTGGCAACCCGGATTTCGCA
CCGCAATACCGGCAAGGCATGTAACGACCCCGTCGCCGACCAGCTCAT
GGCCAAGATCTCGGCAGACGAGAATCTGCACATGATCTTCTACCGCGA
CGTCAGCGAGGCCGCGTTCGACCTCGTGCCCAACCAGGCCATGAAGTC
GCTGCACCTGATTTTGAGCCACTTCCAGATGCCCGGCTTCCAAGTACC
CGAGTTCCGGCGCAAAGCCGTGGTCATCGCCGTCGGGGGTGTCTACGA
CCCGCGCATCCACCTCGACGAAGTCGTCATGCCGGTACTGAAGAAATG
GCGTATCTTCGAGCGCGAGGACTTCACCGGCGAGGGGGCTAAGCTGC
GCGACGAGCTGGCCCTGGTGATCAAGGACCTCGAGCTGGCCTGCGAC
AAGTTCGAGGTGTCCAAGCAACGCCAACTCGACCGGGAAGCCCGTAC
GGGCAAGAAGGTCAGCGCACACGAGCTGCATAAAACCGCTGGCAAAC
TGGCGATGAGCCGTCGTTAG
```

Figure 18A and B

A.

```
mtepaawdeg kpriitltmn paldittsvd vvrptekmrc gaprydpggg
ginvarivhv lggcstalfp aggstgsllm allgdagvpf rvipiaastr
esftvnesrt akqyrfvlpg psltvaeqeq cldelrgaaa saafvvasgs
lppgvaadyy qrvadicrrs stplildtsg gglqhissgv fllkasvrel
recvgsellt epeqlaaahe lidrgraevv vvslgsqgal latrhashrf
ssipmtavsg vgagdamvaa itvglsrgws liksvrlgna agaamlltpg
taacnrddve rffelaaept evgqdqyvwh pivnpeasp
```

B.

```
ATGACGGAGCCAGCGGCGTGGGACGAAGGCAAGCCGCGAATCATCAC
TTTGACCATGAACCCCGCCTTGGACATCACGACGAGCGTCGACGTGGT
GCGCCCGACCGAGAAAATGCGTTGTGGCGCACCTCGCTACGATCCCGG
CGGCGGCGGTATCAATGTCGCCCGCATTGTGCATGTCCTCGGCGGTTG
CTCGACAGCACTGTTCCCGGCCGGCGGGTCGACCGGGAGCCTGCTGAT
GGCGCTGCTCGGTGATGCGGGAGTGCCATTTCGCGTCATTCCGATCGC
GGCCTCGACGCGGGAGAGCTTCACGGTCAACGAGTCCAGGACCGCCA
AGCAGTATCGTTTCGTGCTTCCGGGCCGTCGCTGACCGTCGCGGAGCA
GGAGCAATGCCTCGACGAACTGCGCGGTGCGGCGGCTTCGGCCGCCTT
TGTGGTGGCCAGTGGCAGCCTGCCGCCAGGTGTGGCTGCCGACTACTA
TCAGCGGGTTGCCGACATCTGCCGCCGATCGAGCACTCCGCTGATCCT
GGATACATCTGGTGGCGGGTTGCAGCACATTTCGTCCGGGGTGTTTCT
TCTCAAGGCGAGCGTGCGGGAACTGCGCGAGTGCGTCGGATCCGAAC
TGCTGACCGAGCCCGAACAACTGGCCGCCGCACACGAACTCATTGACC
GTGGGCGCGCCGAGGTCGTGGTGGTCTCGCTTGGATCTCAGGGCGCGC
TATTGGCCACACGACATGCGAGCCATCGATTTTCGTCGATTCCGATGA
CCGCGGTTAGCGGTGTCGGCGCCGGCGACGCGATGGTGGCCGCGATT
ACCGTGGGCCTCAGCCGTGGCTGGTCGCTCATCAAGTCCGTTCGCTTG
GGAAACGCGGCAGGTGCAGCCATGCTGCTGACGCCAGGCACCGCGGC
CTGCAATCGCGACGATGTGGAGAGGTTCTTCGAGCTGGCGGCCGAACC
CACCGAAGTCGGGCAGGATCAATACGTTTGGCACCCGATCGTTAACCC
GGAAGCCTCGCCATGA
```

Figure 19A and B

A.

```
massasdgth ersafrlspp vlsgamgpfm htglyvaqsw rdylgqqpdk
lpiarptial aaqafrdeiv llglkarrpv snhrvferis qevaaglefy
gnrrwlekps gffaqppplt evavrkvkdr rrsfyriffd sgftphpgep
gsqrwlsyta nnreyalllr hpeprpwlvc vhgtemgrap ldlavfrawk
lhdelglniv mpvlpmhgpr gqglpkgavf pgedvlddvh gtaqavwdir
rllswirsqe eesliglngl slggyiaslv asleeglaca ilgvpvadli
ellgrhcglr hkdprrhtvk maepigrmis plsltplvpm pgrfiyagia
drlvhpreqv trlwehwgkp eivwypgght gffqsrpvrr fvqaaleqsg
lldaprtqrd rsa
```

B.

```
ATGGCAAGTTCTGCGAGCGACGGCACCCACGAACGCTCGGCTTTTCGC
CTGAGTCCACCGGTCTTGAGCGGCGCCATGGGACCGTTCATGCACACC
GGTCTGTACGTCGCTCAATCGTGGCGCGACTATCTGGGTCAACAGCCC
GATAAACTGCCGATCGCACGGCCCACTATTGCCTTAGCGGCGCAAGCC
TTTCGAGACGAAATCGTCCTGCTGGGCCTCAAGGCACGACGTCCGGTC
AGCAATCATCGAGTGTTCGAGCGCATCAGCCAAGAAGTGGCCGCTGG
ACTGGAGTTCTATGGGAATCGCAGATGGCTGGAGAAGCCTAGCGGATT
TTTTGCCCAGCCCCCACCGCTCACCGAGGTCGCGGTCCGAAAGGTCAA
GGACCGCAGACGCTCCTTTTATCGCATCTTCTTCGACAGTGGGTTTACG
CCGCATCCGGGTGAACCGGGCAGCCAACGGTGGCTCTCATACACTGCG
AACAATCGCGAGTACGCCCTGTTACTGCGGCACCCAGAGCCGCGTCCC
TGGCTGGTTTGTGTACACGGCACCGAGATGGGCAGGGCCCCGTTGGAT
CTCGCGGTGTTCCGCGCCTGGAAGCTGCATGACGAACTCGGCCTGAAC
ATTGTCATGCCGGTTCTTCCGATGCATGGTCCCCGCGGGCAAGGTCTG
CCGAAGGGCGCCGTTTTTCCCGGAGAAGATGTTCTCGACGATGTGCAT
GGGACGGCTCAAGCGGTGTGGGATATCCGGCGGCTGTTGTCCTGGATA
CGATCGCAGGAGGAGGAGTCGCTGATCGGGTTGAACGGTCTCTCGCTG
GCGGCTACATCGCGTCATTGGTCGCCAGCCTCGAAGAAGGTCTCGCC
TGCGCGATTCTCGGTGTCCCAGTGGCTGATCTGATCGAGTTGTTGGGC
CGCCACTGCGGTCTTCGGCACAAAGACCCCGCCGCCACACCGTCAAG
ATGGCCGAACCGATCGGCCGAATGATCTCGCCGCTCTCACTTACGCCA
CTGGTGCCCATGCCGGGCCGCTTTATCTACGCGGGCATTGCCGACCGA
CTCGTGCATCCACGCGAACAGGTGACTCGCCTCTGGGAGCACTGGGGC
AAACCCGAAATCGTGTGGTATCCAGGCGGTCACACTGGCTTCTTCCAG
TCGCGGCCGGTACGACGGTTTGTCCAGGCTGCGCTGGAGCAGTCGGGC
CTGTTGGACGCGCCACGGACACAGCGCGACCGTTCCGCCTAA
```

Figure 20A and B

A.

```
manpfvkawk ylmalfsski dehadpkvqi qqaieeaqrt hqaltqqaaq
vignqrqlem rlnrqladie klqvnvrqal tladqataag daakateynn
aaeafaaqlv taeqsvedlk tlhdqalsaa aqakkavern amvlqqkiae
rtkllsqleq akmqeqvsas lrsmselaap gntpsldevr dkierryana
igsaelaess vqgrmleveq agiqmaghsr leqirasmrg ealpaggtta
tprpatetsg gaiaeqpygq
```

B.

```
ATGGCCAATCCGTTCGTTAAAGCCTGGAAGTACCTCATGGCGCTGTTC
AGCTCGAAGATCGACGAGCATGCCGACCCCAAGGTGCAGATTCAACA
GGCCATTGAGGAAGCACAGCGCACCCACCAAGCGCTGACTCAACAGG
CGGCGCAAGTGATCGGTAACCAGCGTCAATTGGAGATGCGACTCAAC
CGACAGCTGGCGGACATCGAAAAGCTTCAGGTCAATGTGCGCCAAGC
CCTGACGCTGGCCGACCAGGCCACCGCCGCCGGAGACGCTGCCAAGG
CCACCGAATACAACAACGCCGCCGAGGCGTTCGCAGCCCAGCTGGTG
ACCGCCGAGCAGAGCGTCGAAGACCTCAAGACGCTGCATGACCAGGC
GCTTAGCGCCGCAGCTCAGGCCAAGAAGGCCGTCGAACGAAATGCGA
TGGTGCTGCAGCAGAAGATCGCCGAGCGAACCAAGCTGCTCAGCCAG
CTCGAGCAGGCGAAGATGCAGGAGCAGGTCAGCGCATCGTTGCGGTC
GATGAGTGAGCTCGCCGCGCCAGGCAACACGCCGAGCCTCGACGAGG
TGCGCGACAAGATCGAGCGTCGCTACGCCAACGCGATCGGTTCGGCTG
AACTTGCCGAGAGTTCGGTGCAGGGCCGGATGCTCGAGGTGGAGCAG
GCCGGGATCCAGATGGCCGGTCATTCACGGTTGGAACAGATCCGCGC
ATCGATGCGCGGTGAAGCGTTGCCGGCCGGCGGGACCACGGCTACCC
CCAGACCGGCCACCGAGACTTCTGGCGGGGCTATTGCCGAGCAGCCCT
ACGGTCAGTAG
```

Figure 21A and B

A.

```
   1 mnfpvlppei nsvlmysgag sspllaaaaa wdglaeelgs aavsfgqvts gltagvwqga
  61 aaaamaaaaa pyagwlgsva aqavavagqa raavaafeaa laatvdpaav avnrmamral
 121 amsnllgqna aaiaaveaey elmwaadvaa magyhsgasa aaaalpafsp paqalgggvg
 181 aflnalfagp akmlrlnagl gnvgnynvgl gnvgifnlga anvgaqnlga anagsgnfgf
 241 gnignanfgf gnsglglppg mgniglgnag ssnyglanlg vgnigfantg snnigigltg
 301 dnltgiggln sgtgnlglfn sgtgnigffn sgtgnfgvfn sgsyntgvgn agtastglfn
 361 vggfntgvan vgsyntgsfn agntntggfn pgnvntgwln tgntntgian sgnvntgafi
 421 sgnfsngvlw rgdyeglwgl sggstipaip iglelnggvg pitvlpiqil ptiplnihqt
 481 fslgplvvpd ivipafgggt aipisvgpit ispitlfpaq nfnttfpvgp ffglgvvnis
 541 gieikdlagn vtlqlgnlni dtrinqsfpv tvnwstpavt ifpngisipn nplallasas
 601 igtlgftipg ftipaaplpl tididgqidg fstppitidr iplnlgasvt vgpilingvn
 661 ipatpgfgnt ttapssgffn sgdggvsgfg nfgagssgww nqaqtevaga gsgfanfgsl
 721 gsgvlnfgsg vsglyntggl ppgtpavvsg ignvgeqlsg lssagtalnq sliinlglad
 781 vgsvnvgfgn vgdfnlgaan igdlnvglgn vgggnvgfgn igdanfglgn aglaaglagv
 841 gniglgnags gnvgfgnmgv gnigfgntgt nnlgigltgd nqtgigglns gagniglfns
 901 gtgnvglfns gtgnfglfns gsfntgigng gtgstglfna gnfntgvanp gsyntgsfnv
 961 gdtntggfnp gsintgwfnt gnantgvans gnvdtgalms gnfsngilwr gnfeglfgln
1021 vgitipefpi hwtstggigp iiipdttilp pihlgltgqa nygfavpdip ipaihidfdg
1081 aadagftapa ttllsalgit gqfrfgpitv snvqlnpfnv nlklqflhda fpnefpdpti
1141 svqiqvaipl tsatlgglal plqqtidaie lpaisfsqsi pidippidip astingisms
1201 evvpidvsvd ipavtitgtr idpiplnfdv lssagpinis iidipalpgf gnstelpssg
1261 ffntgggggs gianfgagvs gllnqasspm vgtlsglgna gslasgvlns gvdisgmfnv
1321 stlgsapavi sgfgnlgnhv sgvsidglla mltsggsggs gqpsiidaai aelrhlnpln
1381 ivnlgnvgsy nlgfanvgdv nlgagnlgnl nlgggnlggq nlglgnlgdg nvgfgnlghg
1441 nvgfgnsglg alpgignigl gnagsnnvgf gnmglgnigf gntgtnnlgi gltgdnqtgf
1501 gglnsgagnl glfnsgtgni gffntgtgnw glfnsgsynt gignsgtgst glfnagsfnt
1561 glanagsynt gslnagntnt ggfnpgnvnt gwfnaghtnt ggfntgnvnt gafnsgsfnn
1621 galwtgdhhg lvgfsysiei tgstlvdine tlnlgpvhid qidipgmslf dihelvnigp
1681 friepidvpa vvldihetmv ippivflpsm tiggqtytip ldtppapapp pfrlpllfvn
1741 algdnwivga snstgmsggf vtaptqgili htgpssattg slaltlptvt iptittspip
1801 lkidvsgglp aftlfpggln ipqnaiplti dasgvldpit ifpggftidp lplslalnis
1861 vpdssvpiii vpptpgfgna tatpssgffn sgaggvsgfg nfgagssgww nqahaalaga
1921 gsgvlnvgtl nsgvlnvgsg isglyntaiv glgtpalvsg agnvgqqlsg vlaagtaltq
1981 spiinlglad vgnynlglgn vgdfnlgaan lgdlnlglgn ignanvgfgn ighgnvgfgn
2041 sglgaalgig niglgnagst nvglanmgvg nigfantgtn nlgigltgdn qtgigglnsg
2101 agniglfnsg tgnigffnsg tgnwglfnsg sfntgignsg tgstglfnag gfttglanag
2161 syntgsfnvg dtntggfnpg sintgwfntg nantgiansg nvdtgalmsg nfsngilwrg
2221 nyeglfsysy sldvpritil dahftgafgp vvvppipvla inahltgnaa mgaftipqid
2281 ipalnpnvtg svgfgpiavp svtipaltaa ravldmaasv gatseiepfi vwtssgaigp
2341 twysvgriyn agdlfvggni isgiptlstt gpvhavfnaa sqafntpaln ihqiplgfqv
2401 pgsidaitlf pggltfpans llnldvfvgt pgatipaitf peipanadge lyviagdipl
2461 inipptpgig ntttvpssgf fntgagggsg fgnfganmsg wwnqahtala gagsgianvg
2521 tlhsgvlnlg sglsgiynts tlplgtpalv sglgnvgdhl sgllasnvgq npitivnigl
2581 anvgngnvgl gnignlnlga anigdvnlgf gnigdvnlgf gnigggnvgf gnigdanfgf
2641 gnsglaagla gmgniglgna gsgnvgwanm glgnigfgnt gtnnlgiglt gdnqsgiggl
2701 nsgtgniglf nsgtgnigff nsgtanfglf nsgsyntgig nsgvastglv naggfntgva
2761 nagsyntgsf nagdtntggf npgstntgwf ntgnantgva nagnvntgal itgnfsngil
2821 wrgnyeglag fsfgypiplf pavgadvtgd igpatiippi hipsiplgfa aighigpisi
2881 pniaipsihl gidptfdvgp itvdpitlti pglsldaavs eirmtsgsss gfkvrpsfsf
2941 favgpdgmpg gevsilqpft vapinlnptt lhfpgftipt gpihiglpls ltipgftipg
3001 gtlipqlplg lglsggtppf dlptvvidri pvelhastti gpvslpifgf ggapgfgndt
3061 tapssgffnt gggggsgfsn sgsgmsgvln aisdpllgsa sgfanfgtql sgilnrgagi
3121 sgvyntgtlg lvtsafvsgf mnvgqqlsgl lfagtgp
```

```
TTGAATTTTCCAGTTCTGCCACCGGAAATCAACTCCGTGCTGATGTATTCGGGTGCGGGG
TCGAGCCCGTTGCTGGCGGCGGCCGCGGCGTGGGATGGGCTGGCTGAGGAGTTGGGGTCG
GCGGCGGTGTCGTTTGGGCAGGTGACGTCGGGCCTGACGGCGGGGGTGTGGCAGGGTGCG
GCGGCGGCGGCGATGGCGGCCGCGGCGGCCCCGTATGCGGGGTGGTTGGGTTCGGTGGCG
GCGCAGGCCGTGGCGGTGGCCGGGCAGGCGCGGGCCGCGGTGGCGGCGTTTGAGGCGGCG
TTGGCGGCGACGGTGGATCCGGCGGCGGTGGCGGTCAACCGGATGGCGATGCGGGCGTTG
GCGATGTCGAACCTGCTGGGGCAGAACGCCGCAGCGATCGCGGCCGTCGAGGCCGAGTAC
GAGTTGATGTGGGCCGCCGATGTGGCGGCGATGGCCGGCTACCATTCCGGCGCGTCGGCT
GCTGCCGCGGCGTTGCCGGCGTTCAGCCCACCGGCGCAGGCGTTGGGGGGTGGTGTCGGC
GCGTTCCTCAATGCTCTATTTGCCGGACCCGCGAAGATGTTGAGGCTTAACGCGGGCTTG
GGCAATGTCGGTAATTACAACGTCGGGTTGGGCAATGTCGGGATATTCAACCTGGGCGCA
GCCAATGTCGGTGCGCAGAATTTGGGTGCTGCCAACGCCGGTAGCGGGAATTTCGGTTTC
GGCAATATCGGCAACGCCAACTTCGGGTTCGGCAACTCGGGTCTTGGGTTGCCGCCGGGC
ATGGGCAATATTGGGTTGGGCAATGCGGGCAGCAGCAACTACGGCCTCGCAAACCTGGGT
GTGGGCAACATCGGTTTTGCCAACACGGGTAGCAACAACATCGGGATCGGGTTGACCGGG
GACAACCTGACTGGCATTGGGGGCCTGAATTCAGGAACCGGTAATCTGGGGTTGTTCAAC
TCCGGCACCGGCAACATTGGGTTCTTCAATTCGGGGACCGGCAACTTCGGGGTATTCAAC
TCGGGCAGCTACAACACCGGTGTCGGTAATGCGGGGACGGCCAGTACCGGGTTGTTCAAC
GTTGGTGGGTTCAACACGGGTGTGGCCAACGTGGGTAGCTATAACACGGGCAGCTTCAAC
GCGGGCAACACCAATACGGGTGGCTTCAACCCGGGCAACGTCAACACCGGCTGGCTGAAC
ACCGGCAACACCAACACCGGCATCGCCAACTCGGGCAATGTCAACACCGGCGCGTTCATC
TCGGGCAACTTCAGCAACGGTGTGCTGTGGCGGGGTGACTACGAGGGCCTGTGGGGCTC
TCCGGTGGATCGACCATTCCGGCGATCCCCATTGGTCTCGAGCTCAACGGCGGCGTCGGC
CCCATCACCGTGTTGCCGATCCAGATTTTGCCCACCATCCCGCTCAACATTCACCAAACC
TTCAGCCTCGGCCCGCTGGTCGTTCCGGACATCGTGATCCCCGCTTTTGGTGGCGGTACG
GCCATACCTATCAGCGTCGGCCCCATCACCATCTCGCCCATCACCCTGTTCCCGGCTCAG
AACTTCAACACGACTTTCCCCGTCGGCCCCTTCTTTGGCTTGGGGGTCGTCAACATTTCA
GGAATCGAAATCAAAGATCTTGCCGGCAACGTCACCCTCCAATTAGGTAACCTTAATATC
GACACCAGAATTAACCAGTCATTCCCGGTGACCGTCAACTGGAGTACCCCGGCAGTAACG
ATCTTCCCGAATGGCATCAGTATTCCCAACAATCCACTGGCGCTGCTGGCCAGCGCGTCG
ATCGGCACGCTGGGATTCACGATCCCGGGCTTCACCATTCCCGCTGCGCCGCTGCCGCTG
ACGATCGACATAGACGGCCAGATTGACGGCTTCAGCACCCCGCCGATCACGATCGACCGC
ATCCCGCTGAACCTCGGCGCCAGCGTCACTGTCGGCCCTATCCTGATCAACGGCGTTAAT
ATCCCGGCGACCCCGGGCTTTGGCAACACGACCACCGCTCCGTCGTCGGGTTTCTTCAAC
TCCGGCGACGGTGGGGTGTCGGGCTTCGGGAATTTCGGTGCGGGCAGCTCGGGTTGGTGG
AACCAGGCGCAGACCGAGGTGGCTGGGGCGGGTTCGGGTTTCGCCAATTTCGGTTCGCTG
GGATCGGGTGTGCTGAACTTCGGCTCGGGTGTGTCGGGGCTGTACAACACCGGCGGGTTG
CCGCCGGGGACCCCGGCGGTGGTCTCGGGCATCGGCAATGTTGGTGAGCAGCTGTCGGGG
TTGTCCTCGGCGGGGACGGCACTCAACCAGAGCCTCATCATCAATCTCGGGTTGGCCGAT
GTGGGCAGCGTAAACGTCGGTTTCGGCAACGTCGGGGACTTCAACCTGGGTGCGGCCAAT
ATCGGCGACTTGAACGTGGGTTTGGGCAATGTCGGCGGCGGCAACGTCGGGTTCGGCAAT
ATCGGCGATGCCAACTTCGGGTTGGGCAATGCGGGTCTGGCGGCGGGCCTGGCCGGGGTG
GGCAACATCGGGTTGGGCAATGCCGGCAGCGGCAACGTCGGCTTCGGCAACATGGGTGTG
GGCAACATCGGGTTCGGTAACACCGGCACCAACAACCTCGGGATTGGGCTGACCGGGGAC
AACCAGACTGGGATCGGCGGCTTGAACTCCGGTGCCGGCAACATCGGGTTGTTCAACTCC
GGCACCGGCAACGTCGGGTTGTTCAACTCCGGGACCGGGAACTTCGGGTTGTTCAACTCG
GGCAGCTTCAACACCGGCATCGGCAATGGCGGAACGGGCAGTACTGGGCTTTTCAATGCC
GGTAATTTCAATACCGGTGTGGCCAACCCTGGGTCGTACAACACGGGCAGCTTCAATGTG
GGTGACACCAACACCGGTGGTTTCAACCCGGGCAGCATCAACACCGGCTGGTTCAACACC
GGCAACGCCAACACCGGCGTCGCCAATTCGGGCAATGTCGACACCGGCGCCCTCATGTCG
GGCAACTTCAGCAACGGCATCTTGTGGCGAGGCAACTTCGAGGGCCTGTTCGGCCTGAAC
GTCGGCATCACGATTCCCGAATTCCCGATCCACTGGACTTCAACCGGCGGCATCGGCCCC
```

Figure 22B

```
ATTATCATCCCGGACACCACGATCCTTCCCCCCATCCACCTGGGCCTCACGGGACAAGCG
AACTACGGCTTCGCCGTGCCGGACATCCCCATTCCGGCAATCCACATCGACTTCGACGGT
GCCGCCGACGCCGGCTTCACCGCCCCGGCCACCACCCTGCTTTCTGCGCTGGGCATTACC
GGACAATTCAGGTTCGGCCCGATCACCGTCTCAAACGTCCAGCTCAATCCGTTCAACGTT
AACCTCAAGCTTCAGTTCCTCCACGACGCGTTCCCAAATGAATTTCCCGATCCCACAATC
TCGGTTCAGATACAGGTCGCCATACCCCTTACTTCGGCAACGCTGGGCGGATTGGCCCTG
CCGCTGCAGCAGACCATCGACGCCATCGAATTGCCGGCAATCTCGTTCAGCCAATCCATA
CCCATCGACATTCCGCCGATCGACATCCCGGCCTCCACTATCAACGGAATTTCGATGTCG
GAGGTCGTGCCGATCGATGTGTCCGTCGACATTCCGGCGGTCACCATCACCGGCACCAGG
ATCGACCCGATTCCGCTGAACTTCGACGTTCTCAGCAGCGCCGGACCCATCAACATCTCG
ATCATCGACATTCCGGCGCTGCCGGGCTTTGGCAACTCGACCGAGCTGCCGTCGTCGGGC
TTCTTCAACACCGGCGGCGGTGGCGGCTCGGGCATCGCCAACTTCGGCGCGGGGGTGTCC
GGCTTGCTGAACCAGGCCTCGAGTCCGATGGTGGGGACGCTCTCCGGCCTGGGCAATGCC
GGCAGCCTGGCATCCGGTGTGCTGAACTCCGGCGTCGACATCTCGGGCATGTTCAACGTG
AGCACGCTGGGCTCCGCGCCGGCGGTGATCTCGGGTTTCGGCAACCTGGGCAACCACGTG
TCGGGGGTGTCCATCGATGGCCTGCTGGCGATGCTGACCAGCGGCGGGTCGGGCGGCTCC
GGGCAGCCGAGCATCATCGACGCGGCGATCGCCGAGCTGCGGCACCTGAATCCGCTGAAC
ATCGTCAACCTGGGCAACGTCGGCAGCTACAACCTCGGCTTCGCCAACGTCGGCGACGTC
AACCTGGGCGCGGGCAACCTCGGCAACCTCAACCTCGGCGGTGGCAACCTCGGCGGGCAG
AACCTGGGGTTGGGCAACCTCGGGGACGGCAACGTCGGGTTCGGCAACCTCGGCCACGGC
AATGTCGGGTTCGGCAACTCGGGCCTGGGGGCGCTGCCGGGGATCGGCAACATCGGGTTG
GGCAACGCCGGCAGCAACAACGTCGGCTTCGGCAACATGGGCCTGGGCAACATCGGGTTC
GGCAATACCGGCACCAACAACCTCGGGATCGGGCTGACCGGCGACAACCAGACCGGGTTC
GGCGGCCTGAACTCCGGTGCCGGCAACCTGGGGTTGTTCAACTCCGGCACCGGCAACATC
GGGTTCTTCAACACCGGGACCGGAAACTGGGGGTTGTTCAACTCGGGCAGCTACAACACC
GGCATCGGTAACAGCGGAACGGGCAGTACCGGGCTTTTCAATGCCGGGAGTTTCAACACG
GGTCTGGCCAATGCCGGTAGTTACAACACCGGCAGCCTCAACGCGGGCAACACCAACACC
GGCGGCTTCAACCCTGGCAATGTCAACACCGGCTGGTTCAACGCCGGCCACACCAACACC
GGCGGCTTCAACACGGGCAATGTCAACACCGGCGCGTTCAACTCCGGCAGCTTCAACAAC
GGCGCGCTGTGGACCGGTGATCACCACGGGCTGGTCGGCTTCTCCTACAGCATCGAAATC
ACCGGCAGCACCCTGGTGGACATCAACGAAACCCTCAACCTCGGTCCCGTCCACATCGAT
CAGATCGATATTCCCGGCATGTCGCTGTTCGACATCCACGAACTCGTCAACATCGGGCCC
TTCAGGATCGAGCCCATCGATGTCCCCGCAGTGGTGCTGGACATCCACGAAACGATGGTC
ATCCCGCCCATCGTCTTCCTGCCGAGCATGACGATCGGCGGTCAGACCTACACGATTCCG
CTCGACACGCCCCCGGCCCCCGCCCCGCCGCCCTTCAGACTTCCGTTGCTGTTCGTGAAT
GCGCTCGGCGACAACTGGATCGTTGGGGCGTCCAACTCAACCGGAATGAGTGGTGGCTTT
GTCACCGCACCCACTCAGGGCATCCTGATCCATACCGGTCCCAGCAGCGCAACCACCGGT
AGCCTCGCACTAACCCTCCCAACCGTCACCATCCCAACGATCACGACATCGCCTATCCCG
CTCAAGATCGATGTGTCGGGCGGTCTTCCGGCCTTCACGCTGTTCCCCGGTGGCCTCAAC
ATCCCGCAAAATGCGATCCCGTTGACCATCGATGCGTCCGGCGTGCTGGATCCGATCACG
ATATTCCCGGGTGGTTTCACGATCGATCCGCTGCCACTGAGCCTGGCCCTCAACATCAGC
GTGCCGGACAGCAGCGTTCCGATCATCATCGTTCCGCCGACGCCCGGCTTCGGGAACGCG
ACCGCCACCCCGTCGTCGGGTTTCTTCAACTCCGGCGCGGGCGGGGTGTCGGGTTTCGGC
AACTTCGGGGCCGGCAGCTCAGGCTGGTGGAACCAGGCGCATGCCGCGTTGGCGGGCGCG
GGCTCGGGCGTTCTCAACGTTGGCACGCTGAACTCGGGTGTGCTGAACGTCGGCTCGGGG
ATATCGGGGCTGTACAACACCGCTATCGTGGGTTTGGGGACGCCGGCGCTGGTGTCGGGT
GCCGGCAACGTGGGCCAGCAGCTGTCGGGGGTGTTGGCGGCCGGGACGGCGTTGACCCAA
AGCCCCATCATCAACCTCGGGTTGGCCGATGTCGGCAACTACAACCTCGGGTTGGGCAAC
GTTGGGGACTTCAACCTGGGCGCGGCCAACCTCGGCGACCTCAACCTAGGGTTGGGCAAT
ATCGGGAACGCCAACGTCGGCTTCGGCAATATCGGCCACGGCAACGTCGGGTTTGGCAAT
TCGGGCCTGGGGCGGCGCTCGGCATCGGCAATATCGGGTTGGGCAATGCGGGCAGCACC
AACGTTGGCCTGGCCAACATGGGTGTGGGCAACATCGGGTTCGCCAACACCGGCACCAAC
AACCTCGGGATTGGGCTGACCGGCGACAACCAGACCGGCATCGGCGGCTTGAACTCCGGT
GCCGGCAACATTGGCCTGTTCAACTCCGGCACCGGCAACATCGGGTTCTTCAACTCCGGG
```

Figure 22B (continued)

```
ACCGGAAACTGGGGGTTGTTCAACTCGGGCAGCTTCAACACCGGCATCGGTAATAGCGGA
ACGGGCAGTACTGGGCTTTTCAATGCCGGTGGTTTCACTACGGGTCTGGCCAACGCCGGG
TCGTACAACACGGGCAGCTTCAATGTCGGTGACACCAACACCGGTGGCTTCAACCCGGGC
AGCATCAACACCGGCTGGTTCAACACCGGTAACGCCAACACCGGCATCGCGAACTCGGGC
AATGTCGACACCGGCGCCCTCATGTCGGGCAACTTCAGCAACGGCATCCTGTGGCGGGGC
AACTACGAAGGCCTATTCAGCTATTCCTACAGCCTCGACGTTCCCCGGATCACCATCCTG
GACGCGCATTTCACCGGGGCCTTCGGCCCGGTGGTCGTCCCGCCCATCCCGGTTCTGGCG
ATCAACGCGCACCTGACCGGCAACGCGGCGATGGGCGCCTTCACCATCCCGCAAATCGAT
ATTCCCGCCCTCAATCCGAACGTCACCGGAAGCGTCGGCTTCGGCCCCATCGCGGTCCCC
TCGGTCACCATTCCCGCCCTGACCGCCGCACGAGCGGTCCTCGATATGGCCGCGTCGGTC
GGGGCGACCAGCGAAATAGAGCCGTTTATCGTCTGGACGTCATCCGGTGCGATCGGCCCA
ACGTGGTACTCGGTCGGCAGAATCTACAACGCCGGTGACCTGTTCGTCGGCGGCAATATC
ATCTCGGGAATCCCGACGCTCAGCACGACCGGCCCGGTGCATGCCGTCTTCAATGCGGCA
TCTCAGGCGTTCAACACCCCGGCGCTCAATATTCACCAGATCCCGTTGGGTTTCCAGGTG
CCGGGCAGCATCGACGCGATCACCCTGTTCCCCGGTGGTCTGACGTTCCCGGCGAACTCG
CTGCTGAACCTGGATGTGTTCGTCGGCACCCCCGGCGCCACCATTCCGGCGATCACGTTC
CCGGAGATCCCGGCGAACGCCGACGGCGAACTCTACGTCATCGCCGGCGACATCCCGCTG
ATCAACATCCCGCCCACCCCGGGCATTGGGAACACCACCACCGTTCCGTCGTCGGGCTTC
TTCAACACCGGGGCGGGCGGGGGCTCGGGTTTCGGCAACTTCGGCGCGAACATGTCGGGG
TGGTGGAACCAGGCGCACACCGCTTTGGCAGGCGCGGGTTCGGGTATTGCCAACGTCGGC
ACACTGCACTCCGGCGTGCTCAACCTCGGTTCGGGGCTGTCGGGGATCTACAACACCAGC
ACGCTGCCGCTTGGGACGCCGGCGTTGGTGTCGGGCCTGGGCAACGTCGGTGATCACCTG
TCGGGCTTGTTGGCCTCCAACGTGGGGCAAAACCCCATCACCATCGTCAACATCGGGTTG
GCTAACGTCGGCAACGGCAACGTCGGCCTCGGCAACATCGGCAACCTCAACCTGGGTGCG
GCCAACATTGGCGACGTGAACCTGGGATTCGGCAACATTGGCGACGTGAACCTGGGCTTC
GGCAACATCGGCGGCGGCAACGTCGGGTTCGGCAATATCGGCGATGCCAACTTCGGGTTC
GGGAATTCGGGTCTGGCGGCGGGCCTGGCCGGCATGGGCAATATCGGGCTGGGCAACGCC
GGCAGCGGCAACGTCGGCTGGGCCAACATGGGCCTGGGCAACATCGGGTTTGGCAACACC
GGCACCAACAACCTCGGGATCGGGCTCACCGGCGACAACCAGTCCGGCATCGGCGGCTTG
AACTCCGGCACTGGCAACATTGGCCTGTTCAACTCCGGCACAGGCAATATCGGCTTCTTC
AACTCCGGGACTGCCAACTTCGGGTTGTTCAACTCCGGCAGCTACAACACCGGTATCGGC
AACTCCGGGGTGGCCAGCACCGGGTTGGTCAACGCCGGCGGCTTCAACACCGGTGTGGCA
AACGCCGGGTCGTACAACACGGGCAGCTTCAATGCTGGTGACACCAACACCGGTGGCTTC
AACCCAGGCAGCACCAACACCGGCTGGTTCAACACCGGTAACGCCAACACCGGCGTCGCC
AACGCGGGCAATGTCAACACCGGCGCCCTCATCACGGGCAACTTTAGCAACGGCATCTTA
TGGCGGGGCAATTACGAGGGCTTGGCCGGCTTCTCCTTCGGGTACCCCATTCCGCTGTTC
CCCGCGGTGGGCGCCGACGTCACCGGCGACATCGGCCCCGCCACCATCATTCCGCCCATC
CACATCCCGTCCATCCCGTTGGGCTTCGCCGCGATCGGCCACATCGGGCCGATCAGCATC
CCGAACATCGCCATCCCCTCGATCCACCTGGGCATCGATCCCACCTTCGACGTCGGCCCT
ATCACCGTGGACCCCATCACCCTCACCATCCCTGGCCTAAGTTTGGATGCTGCCGTCTCG
GAGATCAGGATGACGTCCGGAAGCAGCTCCGGATTCAAGGTCAGACCCAGCTTTTCATTC
TTCGCGGTCGGACCCGACGGCATGCCCGGGGGCGAGGTCTCCATACTTCAACCATTCACC
GTGGCACCCATCAACTTGAACCCGACGACACTGCACTTCCCCGGATTCACCATTCCCACC
GGACCCATCCACATCGGCCTGCCGCTGTCGCTGACCATTCCGGGCTTCACCATCCCGGGC
GGCACCCTGATTCCCCAACTCCCGCTGGGCCTCGGTTTGTCCGGCGGCACCCCACCCTTT
GATCTCCCGACGGTCGTTATCGACCGGATCCCGGTGGAGTTACACGCCAGCACCACCATC
GGCCCCGTCAGCCTCCCGATTTTCGGGTTCGGCGGAGCACCGGGCTTTGGCAACGACACC
ACCGCGCCGTCGTCGGGCTTCTTCAACACCGGCGGTGGTGGCGGGTCCGGCTTCTCCAAC
TCCGGGTCGGGCATGTCGGGGGTGCTCAACGCGATCTCGGATCCGCTGCTCGGGTCGGCG
TCGGGCTTCGCCAATTTCGGCACCCAGCTCTCCGGCATCCTCAACCGTGGCGCGGGCATC
TCGGGCGTGTACAACACGGGCACGCTTGGCCTGGTCACATCGGCCTTCGTCTCGGGCTTT
ATGAACGTCGGCCAGCAGCTGTCGGGCCTGCTGTTCGCGGGCACCGGGCCGTAA
```

```
  1 mpdqdtkvrf frvfcwcpvl rmvrimlmha vrawrsaddf pctehmayki aqvaadpvdv
 61 dpevadmvcn riidnaavsa asmvrrpvtv arhqalahpv rhgakvfgve gsysadwaaw
121 angvaareld fhdtflaady shpadnippl vavaqqlgvc gaelirglvt ayeihidltr
181 giclhehkid hvahlgpava agigtmlrld qetiyhaigq alhlttstrq srkgaissswk
241 afapahagkv gieavdramr gegspapiwe gedgviawll agpehtyrvp lpapgepkra
301 ildsytkqhs aeyqsqapid lacrlrerig dldqiasivl htshhthvvi gtgsgdpqkf
361 dpdasretld hslpyifava lqdgcwhher syaperarrs dtvalwhkis tvedpewtrr
421 yhcadpakka fgaraevtlh sgevivdela vadahplgtr pferkqyvek fteladgvve
481 pveqqrflav vesladlesg avgglnvlvd prvldkapvi ppgifr
```

B.

```
   1 gtgccggatc aggacacaaa agtacgcttt tcagggtct tttgttggtg tcctgtgctg
  61 cgtatggtgc ggattatgtt gatgcatgcg gtccgggcgt ggcgcagcgc cgacgatttc
 121 ccgtgcaccg agcacatggc ctacaagatc gcccaggtgg ctgccgatcc ggttgacgtc
 181 gacccggagg tagcggacat ggtgtgcaac cgcatcatcg acaacctgc ggtgagcgcc
 241 gcatcaatgg tgcgcagacc ggtcaccggc gcccgccacc aggcactggc gcatccggtg
 301 cgacacgggg cgaaggtatt tggcgtcgag ggcagctact cggcggactg ggcggcctgg
 361 gccaacggcg tcgccgcgcg tgaacttgac tttcacgaca cgtttctggc cgccgactat
 421 tcgcacccgg cggacaacat cccccactg gtggcggtcg cccagcagct cggcgtgtgc
 481 ggcgcggagc tgatccgcgg tctggtaacc gcctatgaga tccacatcga cctaacccgc
 541 ggaatctgct tgcacgagca aagatcgac catgtcgccc acctgggccc ggcggtggcc
 601 gccggcatcg ggaccatgct gcggctcgac caagagacca tctaccacgc gatcggccag
 661 gccctgcatc tgaccaccag cacccgtcaa tcccgcaagg gcgccatctc cagctggaag
 721 gcgttcgcgc cggcgcatgc cggcaaggtc ggcatcgagg cggtcgatcg ggcgatgcgc
 781 ggcgagggct caccggctcc gatctgggag ggcgaggacg gggtgatcgc ctggctgctg
 841 gccggacccg agcacaccta ccgggtgccg ttgcccgcac ctggtgaacc caagcgcgcc
 901 attctggaca gctacaccaa gcaacactcc gcggagtacc agagccaggc gccgatcgac
 961 ctggcctgcc ggctacgtga gcgtatcggc gatctcgacc agatcgcgtc gatcgtgctg
1021 cacaccagcc accacaccca tgtagtgatc ggaacgggat ccggcgatcc gcagaagttc
1081 gacccggacg cgtcacgcga aaccctcgac cactcgctgc cctacatctt cgccgtggca
1141 ctgcaggacg gctgctggca ccacgagcgc tcctacgcgc ccgagcgggc gcgccgttcc
1201 gacacggtgg cactgtggca caagatttcc accgtcgagg atcccgagtg gacccgccgc
1261 tatcactgcg ccgatccggc caaaaaggcg ttcggggcgc gcgcggaggt gacgctgcac
1321 agcggtgaag tgatcgtgga cgaactggcg gtggccgacg cccatccgct gggcacccgg
1381 ccgttcgagc gcaagcagta cgtagagaag ttcaccgagc tcgccgatgg tgtagtggaa
1441 cccgttgaac agcaacggtt cctggccgta gtagagagtc tcgccgatct cgagagcggt
1501 gccgtgggtg ggctgaacgt gttggtcgat ccgcgggtgc tggacaaagc gccggtgatt
1561 ccaccaggaa tctttcgatg a
```

Figure 23A and B

A.

msfvttrpds igetaanlhe igvtmsahdd gvtplitnve spahdlvsiv
tsmlfsmhge lykaiarqah vihesfvqtl qtsktsywlt elanragtst

B.

GTGTCTTTTGTCACCACACGGCCCGATTCGATTGGGGAAACGGCCGCC
AACCTCCACGAGATCGGGGTGACGATGAGCGCCCATGATGACGGGGT
CACGCCGCTGATCACCAATGTGGAATCCCCCGCCCACGATCTTGTGTC
CATCGTGACGTCGATGCTGTTTTCCATGCACGGCGAGCTGTACAAGGC
GATCGCGCGCCAGGCCCATGTGATCCACGAGTCATTTGTCCAAACACT
TCAGACCAGCAAGACTTCGTATTGGCTCACCGAATTAGCCAACCGCGC
GGGCACCTCCACCTAG

Figure 24A and B

RECOMBINANT BCG TUBERCULOSIS VACCINE DESIGNED TO ELICIT IMMUNE RESPONSES TO MYCOBACTERIUM TUBERCULOSIS IN ALL PHYSIOLOGICAL STAGES OF INFECTION AND DISEASE

CROSS-REFERENCE TO RELATED APPLICATION

This application is a divisional of application Ser. No. 11/945,680, filed Nov. 27, 2007, now U.S. Pat. No. 7,670,609B2.

BACKGROUND OF THE INVENTION

1. Field of the Invention

The invention generally relates to improved *Mycobacterium tuberculosis* (Mtb) vaccines that are successful in preventing the development of symptoms of tuberculosis, both pre- and post-exposure to Mtb. In particular, the invention provides an improved recombinant Bacille Calmette-Guerin (BCG) subunit-based vaccine in which one or more Mtb antigens and one or more Mtb resuscitation or reactivation antigens are overexpressed, and in which at least a portion of the DosR regulon is up-regulated.

2. Background of the Invention

The current prophylactic (pre-exposure) *Mycobacterium tuberculosis* (Mtb) vaccine *Mycobacterium bovis* (*M. bovis*) BCG, introduced over 60 years ago, efficiently protects against severe disease manifestation in children but fails to prevent the establishment of latent TB or disease reactivation of infection in adolescents and adults. Moreover, essentially all novel Mtb vaccines currently in clinical trials are designed as prophylactic rather than both prophylactic and therapeutic (post exposure) vaccines.

It is believed that Mtb progresses through a series of stages during its infectious cycle in man as a reaction to human immune responses and that each stage is orchestrated by a distinct genetic program which directs the expression of stage-specific antigens. If this concept is valid, then a truly comprehensive tuberculosis vaccine should include antigens representing each stage as well as antigens that are stage-independent. Latent tuberculosis (LTBI/latency) appears to be one such stage and current evidence suggests that Mtb adopts a unique physiological phenotype during latency characterized by bacteriostasis (non-replicating persistence), a switch from aerobic to anaerobic respiration, expression of the α-crystalline small chaperone protein (Acr/HspX) and increased resistance to several mycobacterial antibiotics.

Maintenance of the non-replicating persistence state, believed to be typical of Mtb in latent lesions, appears to depend on the continuous production of Th1 cytokines (IFNγ, IL-12 and TNFα) and nitric oxide and the localization of MTB within stable granulomas. However, the reactivation of latent Mtb infection, characterized by resumption of bacterial replication, inflammation and cavitation, can be promptly precipitated by immunosuppressive regimens (e.g., corticosteriods or TNFα-antagonist) and occurs in 5-10% of latently infected individuals, perhaps due to acquired tolerance to environmental mycobacteria, age, and, more significantly, HIV disease. This common clinical scenario and the proven role of the cellular immune system for the maintenance of latency lead to the conclusion that non-replicating persistence is a metastable phenotype determined by three interacting processes: bacterial replication within latent lesions is constrained by effectors of the cellular immune system; bacteria within latent lesions monitor the production of immune effectors; and, decreased production of immune effectors results in resumption of replication.

To date, no successful vaccines have been developed which confer immunity to infection by Mtb and at the same time treat or prevent the development of symptoms of TB after exposure to Mtb, or as a result of reactivation of latent infection. A recombinant BCG vaccine, engineered to elicit an immune response of this kind, might reduce reactivation rates in persons with subtle degrees of immunosuppression produced, for example, by senescence, diabetes, HIV disease, acquired tolerance to environmental mycobacteria or malnutrition. There is thus an ongoing need to develop new TB vaccines, and it would be particularly useful to develop a vaccine that can be used both prophylactically and for post-exposure treatment.

SUMMARY OF THE INVENTION

The present invention is based on the development of a novel recombinant Bacille Calmette-Guerin (rBCG) for use as a vaccine. The vaccine may be used prophylactically to prevent Mtb infection in naive individuals. However, the vaccine is also effective for treating individuals who have already been exposed to and/or infected by Mtb. The vaccine prevents the establishment of infection and likewise prevents the reactivation of latent Mtb in individuals that have been previously infected. The rBCG that is used in the vaccine preparations is genetically engineered to express "classical" Mtb antigens and antigens that are relevant to several stages of the Mtb life cycle, e.g. latency, reactivation and resuscitation. Thus, the immune response that is generated as a result of immunization with the vaccine protects the vaccinated individual from developing an active Mtb infection at any and all stages of exposure to Mtb. In particular, the rBCG overexpresses 1) one or more genes encoding *Mycobacterium tuberculosis* (Mtb) antigens that are known to elicit potent, protective immune responses to Mtb; and 2) one or more genes encoding at least one Mtb resuscitation or reactivation antigen. The antigen encoding sequences are located on an extrachromosomal element or are integrated into the chromosome of the recombinant BCG. In addition, expression of all or part of the Dos R regulon is up-regulated in the novel rBCG. The embodiment of the invention in which the antigen encoding sequences are integrated into the chromosome is depicted schematically in FIG. 1.

BRIEF DESCRIPTION OF THE DRAWINGS

FIGS. 5A and B. Rv3804c amino acid sequence (A, SEQ ID NO: 1) and nucleotide sequence (B, SEQ ID NO: 2).

FIGS. 6A and B. Rv1886c amino acid sequence (A, SEQ ID NO: 3) and nucleotide sequence (B, SEQ ID NO: 4).

FIGS. 7A and B. Rv0867c amino acid sequence (A, SEQ ID NO: 5) and nucleotide sequence (B, SEQ ID NO: 6).

FIGS. 8A and B. Rv1009c amino acid sequence (A, SEQ ID NO: 7) and nucleotide sequence (B, SEQ ID NO: 8).

FIGS. 9A and B. Rv1884c amino acid sequence (A, SEQ ID NO: 9) and nucleotide sequence (B, SEQ ID NO: 10).

FIGS. 10A and B. Rv2389c amino acid sequence (A, SEQ ID NO: 11) and nucleotide sequence (B, SEQ ID NO: 12).

FIGS. 11A and B. Rv2450c amino acid sequence (A, SEQ ID NO: 13) and nucleotide sequence (B, SEQ ID NO: 14).

FIGS. 12A and B. Rv2623c amino acid sequence (A, SEQ ID NO: 15) and nucleotide sequence (B, SEQ ID NO: 16).

FIGS. 13A and B. Rv0288c amino acid sequence (A, SEQ ID NO: 17) and nucleotide sequence (B, SEQ ID NO: 18).

FIGS. 14A and B. Rv2626c amino acid sequence (A, SEQ ID NO: 19) and nucleotide sequence (B, SEQ ID NO: 20).

FIGS. 15A and B. Rv2005c amino acid sequence (A, SEQ ID NO: 21) and nucleotide sequence (B, SEQ ID NO: 22).

FIGS. 16A and B. Rv1996c amino acid sequence (A, SEQ ID NO: 23) and nucleotide sequence (B, SEQ ID NO: 24).

FIGS. 17A and B. Rv0685c amino acid sequence (A, SEQ ID NO: 25) and nucleotide sequence (B, SEQ ID NO: 26).

FIGS. 18A and B. Rv0824c amino acid sequence (A, SEQ ID NO: 27) and nucleotide sequence (B, SEQ ID NO: 28).

FIGS. 19A and B. Rv2029c amino acid sequence (A, SEQ ID NO: 29) and nucleotide sequence (B, SEQ ID NO: 30).

FIGS. 20A and B. Rv2627c amino acid sequence (A, SEQ ID NO: 31) and nucleotide sequence (B, SEQ ID NO: 32).

FIGS. 21A and B. Rv2744c amino acid sequence (A, SEQ ID NO: 33) and nucleotide sequence (B, SEQ ID NO: 34).

FIGS. 22A and B. Rv3347c amino acid sequence (A, SEQ ID NO: 35) and nucleotide sequence (B, SEQ ID NO: 36).

FIGS. 23A and B. Rv1130c amino acid sequence (A, SEQ ID NO: 37) and nucleotide sequence (B, SEQ ID NO: 38).

FIGS. 24A and B. Rv1169c amino acid sequence (A, SEQ ID NO: 39) and nucleotide sequence (B, SEQ ID NO: 40).

DETAILED DESCRIPTION OF THE PREFERRED EMBODIMENTS OF THE INVENTION

Figure 1:
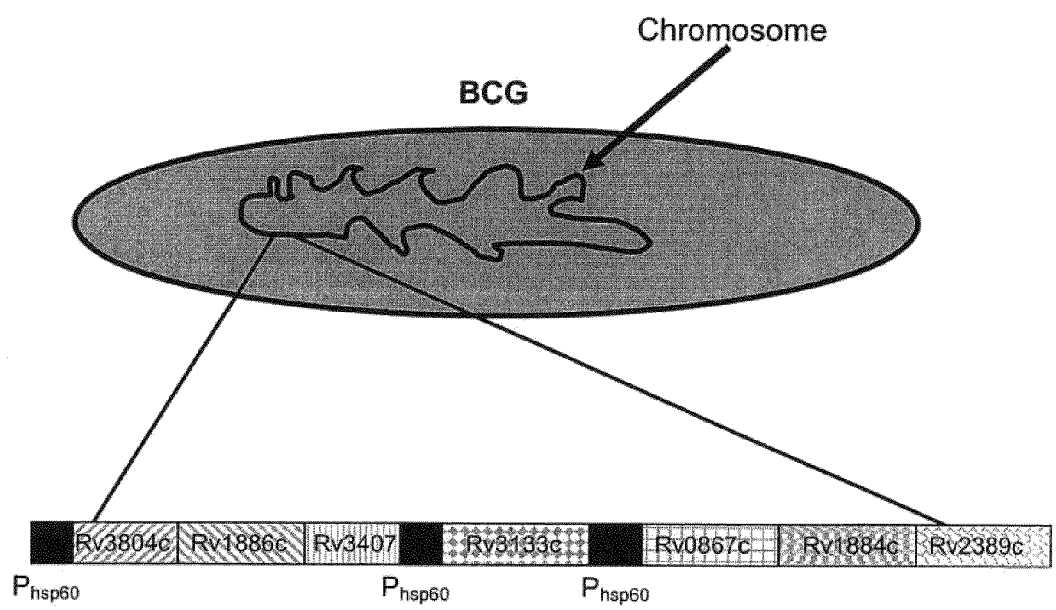
FIG. 1. Schematic representation of the rBCG of the invention.
Figure 2:
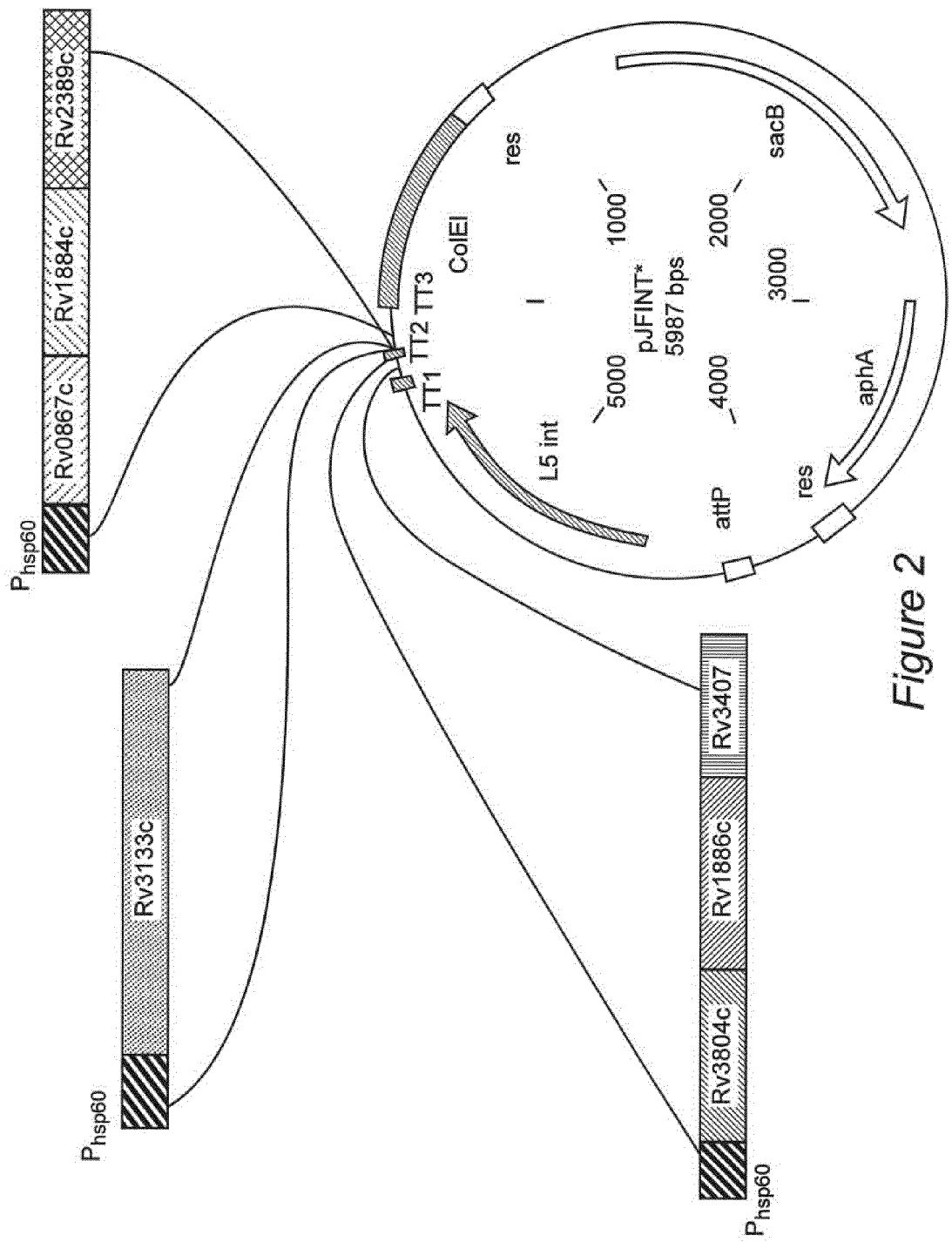
FIG. 2. Diagram of integration plasmid and expression cassette.
Figure 3A:
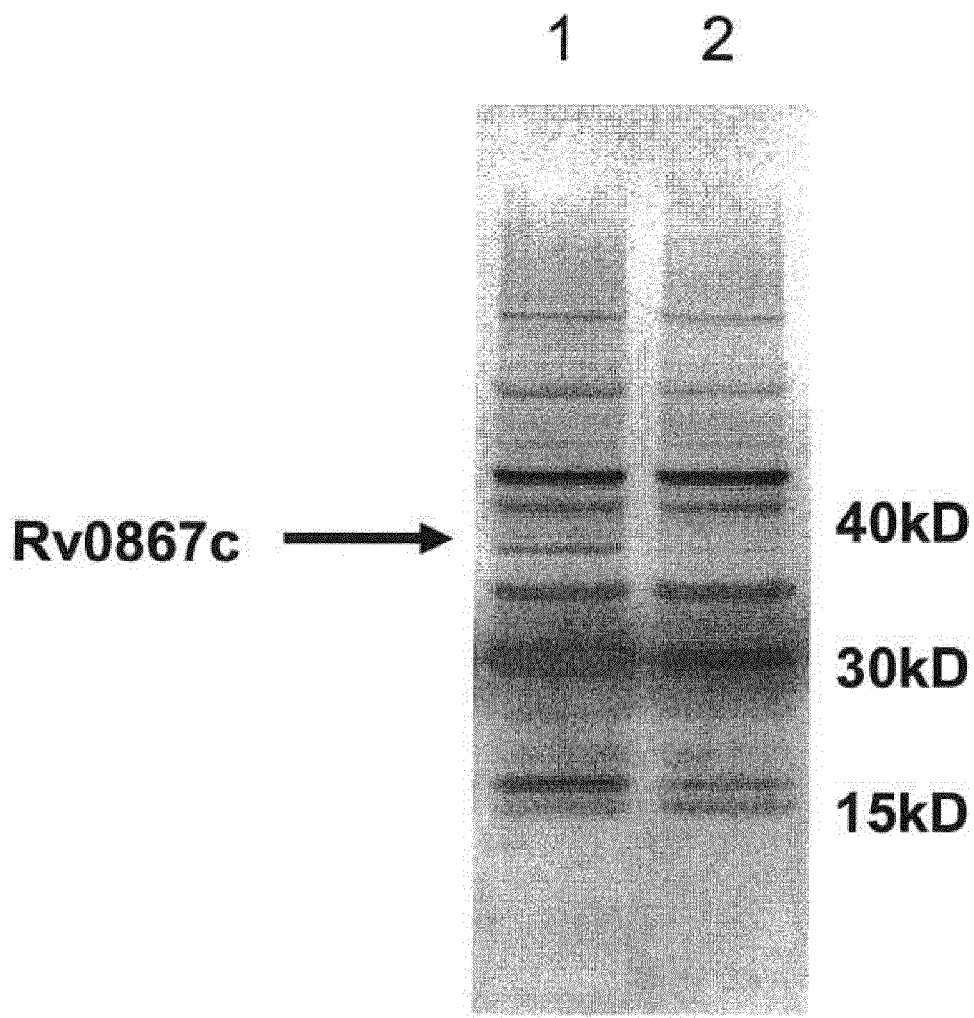
FIGS. 3A-D. Immunoblots demonstrating the expression of chromosomally integrated antigen cassettes. A, Expression or Rv0867c from AERAS-407 precursor AFV-102pRC108, Lane 1=AFV-102pRC108, Lane 2=AFV-102; B, Overexpression of Ag85A and Ag85B from AERAS-407 precursor AFV-102RC108, Lane 1=AFV-102, Lane 2=AFV-102pRC108; C, Expression of Rv3407 from AERAS-407 precursor AFV-102pRC108, Lane 1=AFV-102, Lane 2=AFV-102pRC108; D, Expression of DosR (Rv3133c) from AERAS-407 precursor AFV-102pRC108, Lane 1=AFV-102, Lane 2=AFV-102pRC108.
Figure 3B:
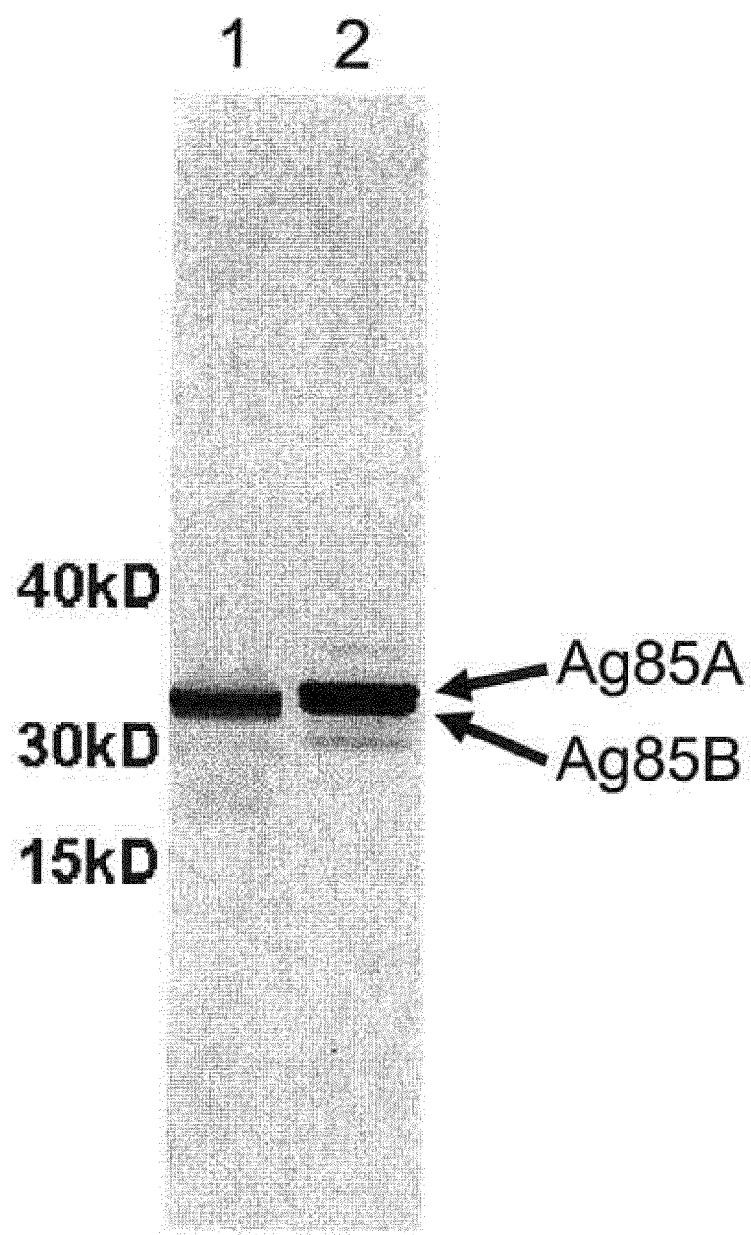
Figure 3C:
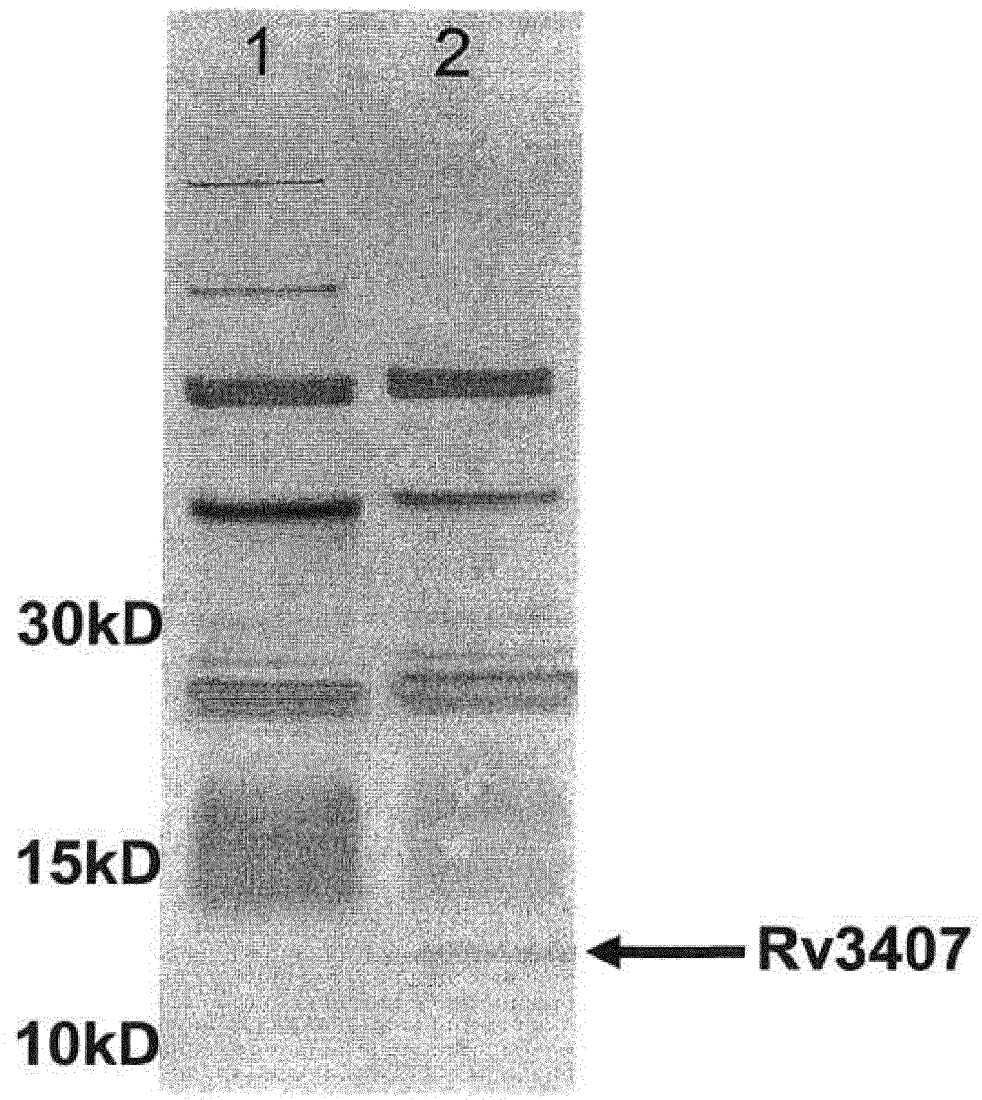
Figure 3D:
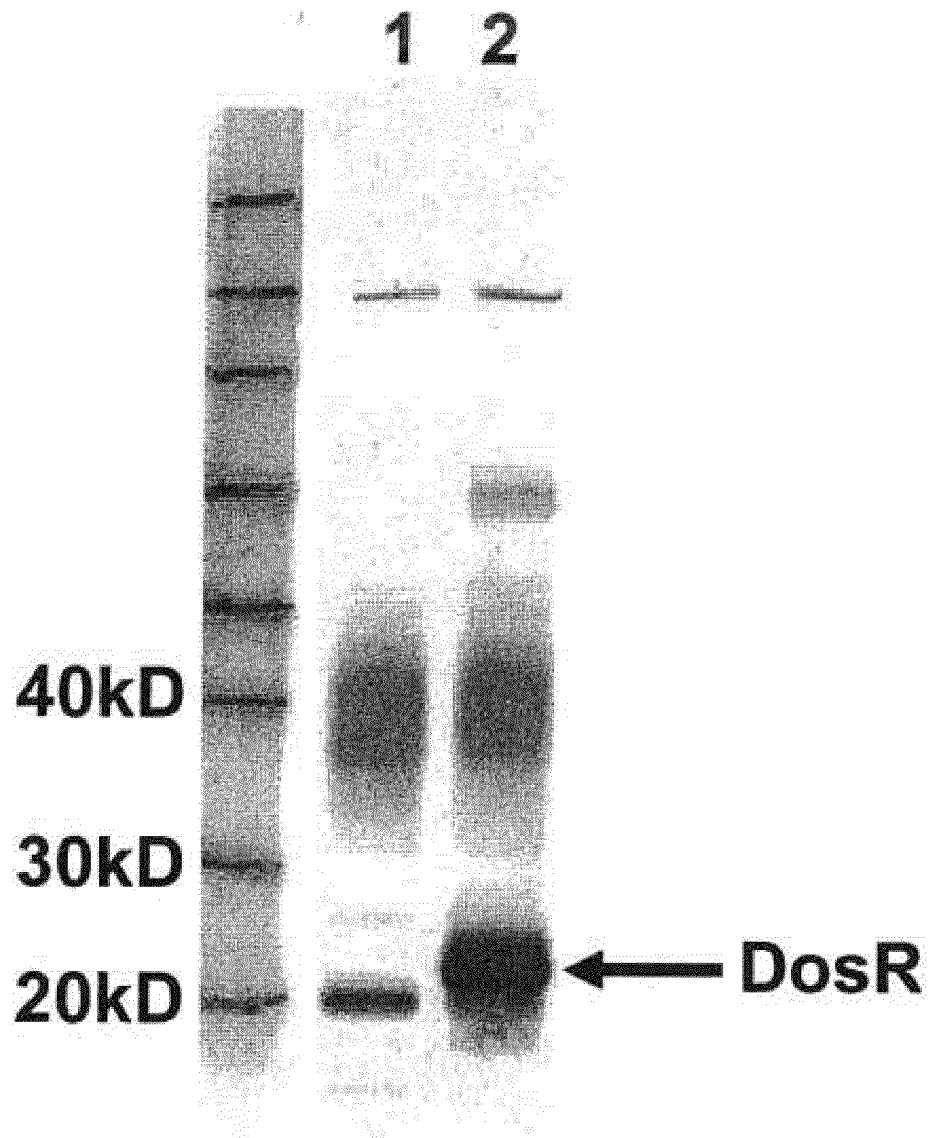
Figure 4:
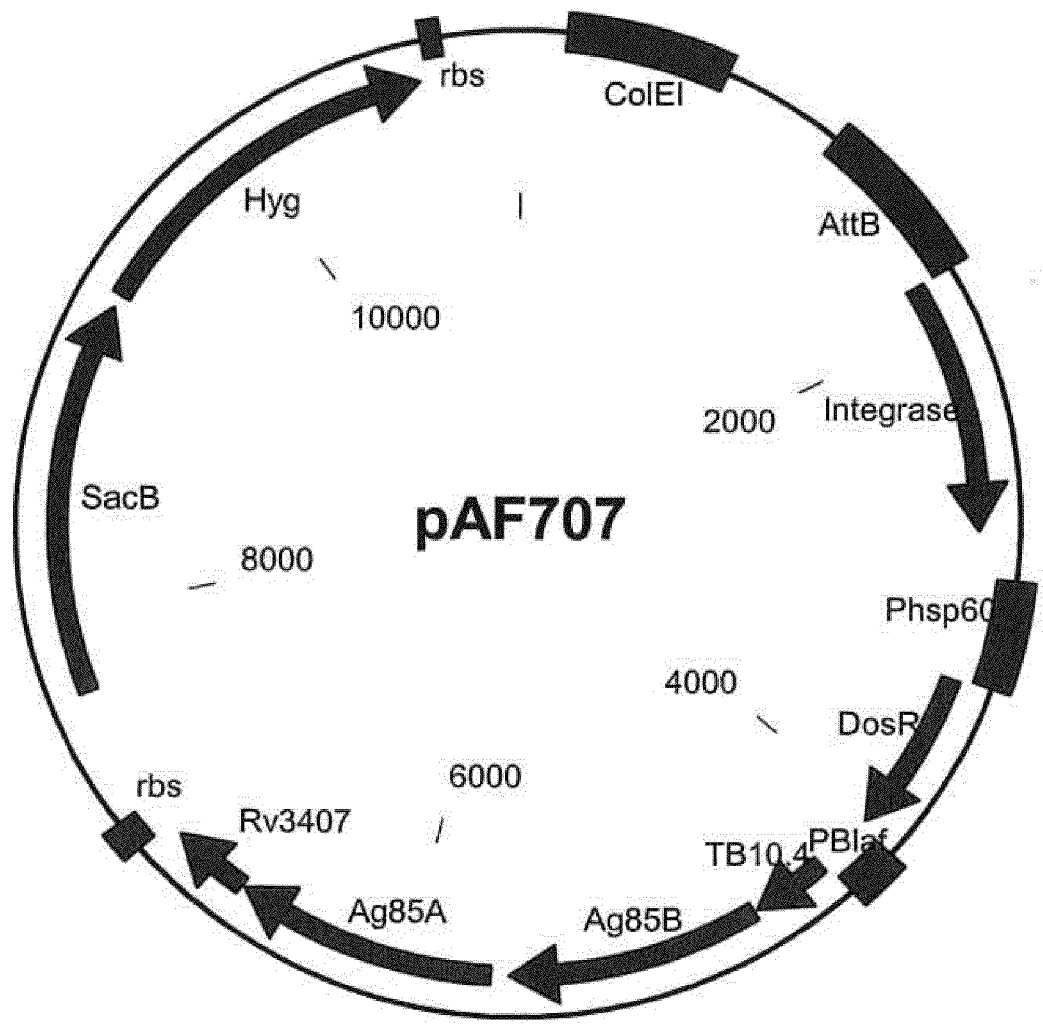
FIG. 4. Diagram of a second integration plasmid and expression cassette.

The present invention provides a novel rBCG for use in Mtb vaccine preparations. The rBCG is genetically engineered to overexpress 1) one or more Mtb antigens, which may include so-called "classical" Mtb antigens such as Rv1886c-Ag85B ("85B") and Rv3804c-Ag85A ("85A"), among others; and 2) at least one Mtb resuscitation/reactivation antigen. In addition, in the rBCG of the invention, the DosR regulon, or a portion thereof, is up-regulated. The DosR regulon, comprised of 48 genes, is typically activated in Mtb as a result of a post-infection drop in $O_2$ tension (hypoxia).

The Mtb antigens that are selected for inclusion in the rBCG of the invention are generally those which are known or predicted to elicit a protective immune response in individuals exposed to the antigens. Various criteria may be used to select suitable antigens, including but not limited to: the observation that individuals with immune responses to the antigen are able to control Mtb infection, determination that the antigen contains one or more T-cell epitopes via an immunoinformatics analysis (e.g. using a program such as that which is found at the website of the Technical University of Denmark: cbs.dtu.dk/services/NetCTL, in which the analysis is based on the identification of proteosome cleavage sites, endoplasmic reticulum (ER) transport efficiency, major histocompatibility (MHC) class 1 binding affinity, etc.); an analysis of experimental evidence based on an in-depth literature search; sorting or ranking of results according to various parameters such as macrophage survival/persistence; up-regulation of expression by the two-component system MprAB; response to hypoxia; involvement in dormancy; expression in lung tissue; genes with promoters that are co-regulated with Rv2031 (Acr); proteins that are secreted (which are more accessible to the immune system); presence of repeats (many virulence associated proteins have amino acid repeat domains); ability to act as a B-cell immunogen; cell wall associated or cell walls biogenesis (membrane-exposed/associated proteins are considered to be more accessible to the immune system; existing vaccine efficacy data; uniqueness to Mtb; etc.) Thus, antigens may be selected based on experimental data demonstrating their efficacy, or alternatively (or in addition) such antigens may be selected based on their predicted abilities. Those of skill in the art are familiar with the implementation of such analyses, and with developing scoring or ranking systems in order to assign a weighted comparative score to candidate antigens. For example, numeric scores may be assigned for each attribute under consideration, and the antigens with the highest cumulative totals may be selected for use. In addition, other considerations may play a role in the decision making process, some of which are practical in nature (e.g. the availability of the antigen, the ease of expressing the antigen, the ease of measuring immune responses to the antigen, etc.)

The starting pool of antigens may be any or all known Mtb open reading frame (ORF) products. Those of skill in the art are familiar with sources for identifying Mtb ORF products, e.g. the "Tuberculist" website sponsored by the Pasteur Institute. In one embodiment of the invention, the antigens from which a selection may be made include but are not limited to all ORF products of *M. tuberculosis* H37Rv as identified in GenBank Accession #AL123456 (NC 000962).

In a preferred embodiment of the invention, the antigens that are expressed by the rBCG are selected from but are not limited to an initial group of 189 antigens presented in Table 1.

TABLE 1

List of 189 selected antigens

| No. | Gene (name) | Size | NCBI Annotation [Updated annotation][a] |
|---|---|---|---|
| Rv0079 | | 273 | hypothetical protein |
| Rv0101 | nrp | 2512 | probable peptide synthase (nrp) |
| Rv0125 | pepA | 355 | probable serine protease pepA (MTB32A) [DegQ] |
| Rv0170 | mce1B | 346 | MCE-family protein mce1B [Ttg2C, periplasmic component ABC transporter] |
| Rv0198c | | 663 | possible zinc metalloprotease [PepO, predicted metalloendopeptidase] |

TABLE 1-continued List of 189 selected antigens

| No. | Gene (name) | Size | NCBI Annotation [Updated annotation][a] |
|---|---|---|---|
| Rv0211 | pckA | 606 | phosphoenolpyruvate carboxykinase pckA (GTP) |
| Rv0227c | | 421 | probable conserved membrane protein |
| Rv0243 | fadA2 | 440 | acetyl-coA acetyltransferase [beta keto-thiolase] |
| Rv0251c | hsp [acr2] | 159 | heat-shock protein hsp (heat-stress induced ribosome-binding protein A) |
| Rv0282 | | 631 | hypothetical protein [AAA ATPase] |
| Rv0283 | | 538 | possible conserved membrane protein [ATP/GTP-binding protein] |
| Rv0284 | [ftsk] | 1330 | possible conserved membrane protein [chromosome partition ATPase] |
| Rv0285 | PE5 | 102 | PE family protein (PE5) |
| Rv0286 | PPE4 | 513 | PPE family protein (PPE4) |
| Rv0287 | exsG | 97 | ESAT-6-like protein esxG (conserved hypothetical protein TB9.8) |
| Rv0288 | esxH (TB10.4) | 96 | low MW protein antigen 7 esxH (10 kDa antigen) CFP-7, TB10.4) |
| Rv0289 | | 295 | hypothetical protein [transporter] |
| Rv0290 | | 472 | probable conserved trans-membrane protein (mgcP3) [transporter] |
| Rv0292 | | 331 | probable conserved trans-membrane protein |
| Rv0350 | dnaK | 625 | molecular chaperone DnaK |
| Rv0351 | grpE | 235 | probable grpE protein (HSP-70 cofactor) |
| Rv0383c | | 284 | possible conserved secreted protein |
| Rv0384c | clpB | 848 | probable endopeptidase ATP binding protein ClpB (chain B) heat-shock protein F84.1 |
| Rv0450c | mmpl4 | 967 | probable conserved trans-membrane mmpL4 [drug exporting] |
| Rv0467 | icl [aceA] | 428 | isocitrate lyase (icl) |
| Rv0468 | fadB2 | 268 | 3-hydroxybutyryl-CoA dehydrogenase |
| Rv0503c | cmaA2 | 302 | cyclopropane-fatty-acyl-phospholipid-synthase 2 (cyclopropane mycolic acid synthase 2, CMAA2) |
| Rv0569 | | 88 | hypothetical protein |
| Rv0572c | | 113 | hypothetical protein |
| Rv0574c | [pgsA] | 380 | hypothetical protein [pgsA poly-gamma-glytamyl biosyntehsis] |
| Rv0588 | yrbE2B | 295 | conserved hypothetical integral membrane protein YrbE2B [putative Ttg2B, ABC-type transport system involved in resistance to organic solvents, permease component) |
| Rv0628c | | 383 | hypothetical protein |
| Rv0685 | Tuf | 396 | elongation factor Tu, tuf [iron-regulated] |
| Rv0754 | PE_PGRS11 | 584 | PE-PGRS family protein (PE_PGRS11) [phosphoglycerate mutase] |
| Rv0798c | cfp29 | 265 | 29 kDa antigen CFP-29 [linocin M-18 bacteriocin] |
| Rv0824c | desA1 | 389 | probable acyl-[-acyl-carrier-desaturase desA1] |
| Rv0847 | lpqS | 130 | probable lipoprotein LPQS |
| Rv0867c | rpfA | 407 | possible conserved trans-membrane protein [transglycosylase, rpfA] |
| Rv0885 | | 340 | hypothetical protein |
| Rv1006 | | 567 | hypothetical protein |
| Rv1009 | rpfB | 362 | possible resuscitation-promoting factor rpfB [transglycosylase, C5 adhesion domain] |
| Rv1057 | | 393 | hypothetical protein |
| Rv1094 | desA2 | 271 | possible acyl-[-acyl-carrier protein] desaturase (DESA2) |
| Rv1124 | ephC | 316 | probable epoxide hydrolase EPHC (epoxide hydratase) |
| Rv1130 | [prpD] | 526 | hypothetical protein [2 methyl-citrate dehydratase] |
| Rv1131 | gltA1 | 393 | citrate synthase (glaA1) |
| Rv1169c | PE11 | 100 | PE family protein (PE11) [triacyl glycerol lipase] |
| Rv1174c | [sak5] | 110 | low MW T-cell antigen TB8.4 [secretion antigen SA5K] |
| Rv1182 | papA3 | 472 | probable conserved polyketide synthase associated protein PAPA3 |
| Rv1186c | | 538 | hypothetical protein [regulator of polyketide synthase expression] |
| Rv1187 | rocA | 543 | probable proline-5-carboxylate dehydrogenase rocA |
| Rv1188 | | 329 | probable proline dehydrogenase |
| Rv1196 | PPE18 (mtb39a) | 391 | probable proline dehydrogenase PPE family protein [MTB39A] |
| Rv1221 | sigE | 257 | RNA polymerase sigma-70 factor (SigE) |
| Rv1347c | | 210 | hypothetical protein [GCN5-related N-acetyltransferase fold] |
| Rv1348 | [lrtA] | 859 | probable drug-transport trans-membrane ATP-binding protein ABC-transporter [MdlA/MsbA essential ABC transporter, siderophore interaction protein] |

TABLE 1-continued

List of 189 selected antigens

| No. | Gene (name) | Size | NCBI Annotation [Updated annotation][a] |
|---|---|---|---|
| Rv1349 | [irtB] | 579 | possible drug-transport trans-membrane ATP-binding protein ABC-transporter [ATM1 ABC siderophore-iron transporter] |
| Rv1411c | lprG | 236 | possible conserved lipoprotein lprG |
| Rv1436 | gap | 339 | glyceraldehyde-3-phosphate dehydrogenase |
| Rv1461 | [sufB] | 846 | hypothetical protein [sufB, cytosine desulfurase activator] |
| Rv1462 | [sufD] | 397 | hypothetical protein [sufD, cytosine desulfurase activator] |
| Rv1464 | csd [sufS] | 417 | possible cysteine desulfurase csd [SufS] |
| Rv1465 | [nifU] | 162 | possible nitrogen fixation related protein [IscU] |
| Rv1466 | | 115 | hypothetical protein [PaaD, predicted metal-sulfur cluster biosynthetic enzyme] |
| Rv1477 | ripA | 427 | hypothetical invasion protein [Nlp_p60 cell-wall hydrolase] |
| Rv1478 | | 241 | hypothetical invasion protein [Nlp_p60 cell-wall hydrolase] |
| Rv1594 | nadA | 349 | quinoline synthetase (nadA) |
| Rv1636 | TB15.3 | 146 | iron-regulated conserved hypothetical protein TB15.3 [USP] |
| Rv1733c | | 210 | probable conserved transmembrane protein |
| Rv1734c | | 80 | hypothetical protein [dihydrolysine acetyl-transferase] |
| Rv1735c | | 165 | hypothetical membrane protein |
| Rv1736c | narX | 652 | possible nitrate reductase narX |
| Rv1737c | narK2 | 395 | possible nitrate/nitrite transporter narK2 |
| Rv1738 | | 94 | hypothetical protein |
| Rv1793 | esxN | 94 | putative ESAT-6-like protein ESXN (ESAT-6-like protein 5) |
| Rv1812c | [ndH] | 400 | possible dehydrogenase [Ndh, NADH dehydrogenase, FAD-containing subunit] |
| Rv1813c | | 143 | hypothetical protein |
| Rv1876 | bfrA | 159 | probable bacterioferritin bfrA |
| Rv1884c | rpfC | 176 | probable resuscitation-promoting factor rpfC [transglycosylase] |
| Rv1886c | ftpB (Ag85B) | 325 | secreted antigen 85-B FBPB (85-B) (mycolyl-transferase 85B) |
| Rv1908c | katG | 740 | catalase-peroxidase-peroxinitritase-T katG |
| Rv1926c | mpt63 | 159 | immunogenic protein MPT63 (16 kDa immunoprotective extracellular antigen) |
| Rv1980c | mpb64 | 228 | immunogenic protein MPT64 |
| Rv1986 | | 199 | probable conserved integral membrane protein [lysine efflux permease] |
| Rv1996 | | 317 | hypothetical protein [USP] |
| Rv1997 | ctpF | 905 | probable metal cation transporter P-type APTase cptF |
| Rv1998c | | 258 | hypothetical protein |
| Rv2004c | | 498 | hypothetical protein [predicted kinase] |
| Rv2005c | | 295 | hypothetical protein [USP-like] |
| Rv2006 | otsB1 | 1327 | probable trehalose-6-phosphate phosphatase OSTB1 |
| Rv2007c | fdxA | 114 | probable ferrodoxin fdxA |
| Rv2008c | | 441 | hypothetical protein [predicted ATPase] |
| Rv2011c | | 143 | hypothetical protein[transcription regulator] |
| Rv2028c | | 279 | hypothetical protein [USP] |
| Rv2029c | pfkB | 339 | possible phosphofructokinase (pfkB) |
| Rv2030c | | 681 | hypothetical protein [putative esterase/transferase] |
| Rv2031c | acr (α-crystallin) | 144 | heat-shock protein HspX (alpha-crystallin homolog) 14 kDa antigen Hsp16.3 |
| Rv2032 | acg | 331 | conserved hypothetical protein Acg |
| Rv2110c | [prcB] | 291 | proteosome (beta subunit) PrcB [HslV protease] |
| Rv2123 | PPE37 | 473 | PPE family protein (PPE37) |
| Rv2140c | TB18.6 [pepB] | 176 | hypothetical protein (TB18.6) [PEBP, bacterial/archeal phosphatidylethanolamine-binding protein] |
| Rv2182c | [pslC] | 247 | 1-acylglycerol-3-phosphate O-acyltransferase |
| Rv2224c | [caeA] | 520 | probable exported protease [cae, carboxylase A, TAP-like protein] |
| Rv2244 | acpM | 115 | acyl-carrier protein (acpM) |
| Rv2245 | kasA | 416 | 3-oxoacyl-(acyl carrier protein) synthase (kasA) |
| Rv2246 | kasB | 438 | 3-oxoacyl-(acyl carrier protein) synthase (kasB) |
| Rv2251 | [glcD] | 475 | possible flavoprotein [GlcD, FAD/FMN-containing dehydrogenases] |
| Rv2377c | mbtH | 71 | putative conserved protein MBTH |
| Rv2378c | mbtG | 431 | lysine-N-oxygenase MBTG [lucD] |
| Rv2380c | mbtE | 1682 | peptide synthase MBTE [EntF] |
| Rv2381c | mbtD | 1004 | polyketide synthase MBTD [acyl-transferase, KR domain] |

TABLE 1-continued

List of 189 selected antigens

| No. | Gene (name) | Size | NCBI Annotation [Updated annotation][a] |
|---|---|---|---|
| Rv2382c | mbtC | 444 | polyketide synthase MBTC |
| Rv2383c | mbtB | 1414 | phenyloxazoline synthase (MBTB) [EntF, GrsT] |
| Rv2386c | mbtI | 450 | anthranilate synthase component I (MBTA) [salicylate synthase] |
| Rv2389c | rpfD | 154 | probable resuscitation-promoting factor rpfE [transglycosylase] |
| Rv2428 | ahpC | 195 | alkyl hydroxyperoxide reductase C protein ahpC |
| Rv2429 | ahpD | 177 | alkyl hydroxyperoxide reductase D protein ahpD |
| Rv2430c | PPE41 | 194 | PPE family protein (PPE41) |
| Rv2450c | rpfE | 172 | probable resuscitation-promoting factor rpfE [transglycosylase] |
| Rv2457c | clpX | 426 | ATP-dependent protease ATP-binding subunit (CplX) |
| Rv2466c | | 207 | hypothetical protein [putative DsbA__FrnE] [thiol oxidoreductase, polyketide biosynthesis] |
| Rv2510c | | 533 | hypothetical protein [ATP binding domain] |
| Rv2515c | | 415 | hypothetical protein [putative zinc peptidase] |
| Rv2516c | | 250 | hypothetical protein |
| Rv2557 | | 224 | hypothetical protein |
| Rv2590 | fadD9 | 1168 | probable fatty-acid coA ligase fadD9 |
| Rv2620c | | 141 | probable conserved trans-membrane protein |
| Rv2621c | | 224 | possible transcriptional regulatory protein |
| Rv2622 | | 273 | possible methyltransferase (methylase) |
| Rv2623 | TB31.7 | 297 | hypothetical protein TB31.7 [USP] |
| Rv2625c | | 393 | probable conserved trans-membrane alanine-rich and leucine-rich protein [zinc-protease M-50 CBS domain] |
| Rv2626c | | 143 | hypothetical protein [CBS pair-binding/regul, euk] |
| Rv2627c | | 413 | hypothetical protein |
| Rv2628 | | 120 | hypothetical protein |
| Rv2629 | | 374 | hypothetical protein [peptide chain release factor erF1] |
| Rv2657c | | 86 | probable phiRv2 prophage protein [MerR regulatory protein] |
| Rv2659c | | 375 | probable phiRv2 prophage integrase |
| Rv2660 | | 75 | hypothetical protein |
| Rv2710 | sigB | 323 | RNA polymerase sigma factor (SigB) |
| Rv2744c | 35kd-Ag [pspA] | 270 | conserved 35 kDa alanine-rich protein [phage-shock protein IM30] |
| Rv2780 | ald | 371 | secreted L-alanine dehydrogenase ald (40 kDa antigen, TB43) |
| Rv2833c | ugpB | 436 | probable Sn-glycerol-3-phosphate-binding lipoprotein UGPB |
| Rv2856 | nicT | 372 | possible nickel-transport integral membrane protein nicT |
| Rv2869c | | 404 | probable conserved trans-membrane protein [putative pdz membrane associated zinc-metalloprotease] |
| Rv2875 | mpt70 | 193 | major secreted immunogenic protein MPT70 |
| Rv2930 | fadD26 | 626 | fatty-acid-coA ligase FadD26 |
| Rv2986c | hupB | 214 | probable DNA-binding protein HU homolog HupB (histone-like protein, 21 kDa laminin-2 binding protein) |
| Rv2999 | lppY | 321 | probable conserved lipoprotein LPPY |
| Rv3126c | | 104 | hypothetical protein |
| Rv3127 | | 344 | hypothetical protein [possible nitroreductase] |
| Rv3129 | | 110 | hypothetical protein |
| Rv3130c | tgs1 | 463 | hypothetical protein [diacylglycerol acyltransferase] |
| Rv3131 | nfnB | 332 | hypothetical protein [possible nitroreductase NfnB] |
| Rv3132c | devS | 578 | two-component sensor histidine kinase DevS |
| Rv3133c | devR | 217 | two-component transcription regulatory protein DevR |
| Rv3134c | | 268 | hypothetical protein [USP] |
| Rv3139 | fadE24 | 468 | probable acyl-coA dehydrogenase FadE24 |
| Rv3140 | fadE23 | 401 | probable acyl-coA dehydrogenase FadE23 |
| Rv3173c | | 200 | probable transcriptional regulatory protein (TetR/acRR family) |
| Rv3229c | desA3 | 427 | possible linoleoyl-coA desaturase (delta-(6)-desaturase) |
| Rv3250c | rubB | 495 | probable rubredoxin rubB |
| Rv3251c | rubA | 55 | probable rubredoxin rubA |
| Rv3283 | sseA | 297 | probable thiosulfate sulfurtranserase SSEA (rhodanase) |
| Rv3290c | lat | 449 | L-lysine epsilon aminotransferase |
| Rv3347c | PPE55 | 3157 | PPE family protein (PE55) [8 copies pentapeptide repeats] |
| Rv3372 | ostB2 | 391 | possible trehalose-6-phosphate phosphatase (OSTB2) |
| Rv3515c | fadD19 | 548 | AMP-dependent fatty-acid-coA ligase FadD19 |
| Rv3516 | echA19 | 263 | enoyl-coA hydratase/isomerase (echA19) |

TABLE 1-continued

List of 189 selected antigens

| No. | Gene (name) | Size | NCBI Annotation [Updated annotation][a] |
|---|---|---|---|
| Rv3546 | fadA5 | 391 | acetyl-coA acetyltransferase (FadA5) |
| Rv3570c | [ncnH] | 394 | possible oxidoreductase [NcnH, naphthocyclinone hydroxylase] |
| Rv3593 | lpqF [penP] | 452 | probable conserved lipoprotein LPQF [PenP, beta-lactamase class A] |
| Rv3597c | lsr2 | 112 | probable iron-regulated LSR2 protein precursor |
| Rv3616c | [espB] | 392 | conserved hypothetical alanine-rich and glycine-rich protein [ESAT secretion system component] |
| Rv3619c | esxV | 94 | putative ESAT-6-like protein ESXV (ESAT-6-like protein 1) |
| Rv3660c | | 350 | hypothetical protein |
| Rv3763 | lpqH | 159 | 19 kDa lipoprotein antigen precursor LPQH |
| Rv3804c | fbpA (Ag85A) | 338 | secreted antigen 85-A FBPA (85-A) (mycolyl-transferase 85A) |
| Rv3812 | PE_PGRS62 | 504 | PE-PGRS family protein (PE_PGRS62) |
| Rv3833 | | 263 | transcriptional regulatory protein [probable araC family] |
| Rv3839 | | 258 | hypothetical protein |
| Rv3840 | | 137 | probable transcriptional regulatory protein [cell-envelope related transcription attenuator] |
| Rv3841 | bfrB | 181 | possible bacterioferritin bfrB |
| Rv3871 | [Ftsk] | 591 | hypothetical protein [FtsK_SPOIIIE] |
| Rv3873 | PPE68 | 368 | PPE family protein [PPE68, RD1 T/B immunogen] |
| Rv3874 | esxB | 100 | 10 kDa culture filtrate antigen ESXB (LHP, CFP-10) |
| Rv3875 | esxA | 95 | 6 kDa early secretory antigenic target ESXA (ESAT-6) |
| Rv3876 | [Ftsk] | 666 | conserved hypothetical proline and alanine-rich protein [chromosome partitioning ATPase] |
| Rv3878 | | 280 | conserved hypothetical alanine-rich protein |
| Rv3879c | | 729 | hypothetical alanine and proline-rich protein |

[a]NCBI annotation is based on Accession # AL123456 (NC_000962); updated annotation is based on bioinformatic analyses, data from MTB-related servers and experimental evidence.

In a more preferred embodiment of the invention, the antigens that are expressed by the rBCG are the 45 antigens presented in Tables 2 and 3.

TABLE 2

Top-ranking antigens (according to Class/Phase)

| No. | Gene (name) | Size | NCBI annotation [Updated annotation][a] | Score Qual | Score Quant |
|---|---|---|---|---|---|
| Class: DORMANCY/DosR | | | | | |
| Rv1738 | | 94 | hypothetical protein | 9 | 14 |
| Rv2623 | TB31.7 | 297 | heat-shock protein TB31.7 [universal stress protein] | 9 | 14 |
| Rv2031c | acr (α-crystalllin) | 144 | heat-shock protein HspX (alpha-crystallin homolog) 14 kDa antigen Hsp16.3 | 8 | 14 |
| Rv2032 | acg | 331 | conserved hypothetical protein Acg [nitroreductase] | 8 | 13 |
| Rv2626c | | 143 | hypothetical protein [CBS pair-binding/regulation, euk] | 8 | 13 |
| Rv2005c | | 295 | hypothetical protein [USP-like] | 8 | 12 |
| Rv3127 | | 344 | hypothetical protein [possible nitroreductase] | 8 | 12 |
| Rv1733c | | 210 | probable conserved trans-membrane protein | 8 | 11 |
| Rv1996 | | 317 | hypothetical protein [USP] | 8 | 10 |
| Rv2628 | | 120 | hypothetical protein | 8 | 9 |
| Rv0079 | | 273 | hypothetical protein | 7 | 11 |
| Rv3130c | [tgs1] | 463 | hypothetical protein [diacylglycerol acyltransferase] | 7 | 11 |
| Rv3131 | [nfnB] | 332 | hypothetical protein [possible nitroreductase NfnB] | 7 | 11 |
| Rv1813c | | 143 | hypothetical protein | 7 | 9 |
| Rv2006 | otsB1 | 1327 | probable trehalose-6-phosphate phosphatase OTSB1 | 7 | 9 |
| Rv2029c | pfkB | 339 | possible phophofructokinase (pfkB) | 7 | 9 |
| Rv2627c | | 413 | hypothetical protein | 7 | 9 |

TABLE 2-continued

Top-ranking antigens (according to Class/Phase)

| No. | Gene (name) | Size | NCBI annotation [Updated annotation][a] | Score Qual | Score Quant |
|---|---|---|---|---|---|
| Rv2030c | | 681 | [serine endopeptidase] hypothetical protein [putative esterase/transferase] | 6 | 10 |
| Rv3132c | devs | 578 | two component sensor histidine kinase DEVS | 6 | 10 |
| Rv2629 | | 374 | hypothetical protein [peptide release factor erf-1] | 6 | 9 |

Class: RESUSCITATION

| Rv2450c | rpfE | 172 | probable resuscitation-promoting factor rpfE [transglycosylase] | 9 | 14 |
|---|---|---|---|---|---|
| Rv1009 | rpfB | 362 | possible resuscitation-promoting factor rpfB [transglycosylase, C5 adhesion domain] | 9 | 13 |
| Rv0867c | rpfA | 407 | possible conserved trans-membrane protein [transglycosylase, rpfA] | 9 | 12 |
| Rv2389c | rpfD | 154 | probable resuscitation-promoting factor rpfD [transglycosylase] | 8 | 10 |
| Rv1884c | rpfC | 176 | probable resuscitation-promoting factor rpfC [transglycosylase] | 7 | 8 |

Class: REACTIVATION

| Rv1009 | rpfB | 362 | possible resuscitation-promoting factor rpfB [transglycosylase, C5 adhesion domain] | 9 | 13 |
|---|---|---|---|---|---|
| Rv0867c | rpfA | 407 | possible conserved trans-membrane protein [transglycosylase, rpfA] | 9 | 12 |
| Rv0288 | esxH (TB10.4) | 96 | low MW protein antigen 7 esxH (10 kDa antigen) CFP-7, TB10.4) | 8 | 13 |
| Rv0685 | Tuf | 396 | elongation factor Tu [iron-regulated] | 8 | 9 |
| Rv0824c | desA1 | 389 | probable acyl[-acyl-carrier-desaturase desA1] | 7 | 10 |
| Rv2744c | 35kd-Ag [pspA] | 270 | conserved 35 kDa alanine-rich protein [phage-shock protein IM30] | 7 | 8 |
| Rv3347c | PPE55 | 3157 | PPE 55 Family Protein [8 copies pentapeptide repeats] | 6 | 10 |
| Rv1130 | prpD | 526 | hypothetical protein [2 methyl-citrate dehydratase] | 6 | 9 |
| Rv1169c | PE11 | 100 | PE family protein (PE11) [triacyl glycerol lipase] | 6 | 9 |

Class: CLASSICAL

| Rv1886c | fbpB (Ag85B) | 325 | mycolyl transferase/fibronectin binding | 8 | 14 |
|---|---|---|---|---|---|
| Rv1980c | mpb64 | 228 | antigen MPT64/MPB64 | 7 | 13 |
| Rv3804c | fbpA (Ag85A) | 338 | mycolyl transferase/fibronectin binding | 7 | 13 |
| Rv3875 | esxA | 95 | 6 kDa early secretory antigen esxA | 6 | 11 |
| Rv1926c | mpt63 | 159 | immunogenic protein MPT63 (16 kDa immunoprotective extracellular protein) | 6 | 10 |
| Rv0467 | icl | 428 | isocitrate lyase (icl) [AceA] | 6 | 9 |

Class: OTHERS

| Rv3873 | PPE68 | 368 | hypothetical protein | 8 | 13 |
|---|---|---|---|---|---|
| Rv1908c | katG | 740 | catalase-peroxidase-peroxinitritase-T (KATG heme dependent) | 7 | 10 |
| Rv1174c | sak5 | 110 | low MW T-cell antigen TB8.4 (secreted) | 7 | 9 |
| Rv1349 | irtB | 579 | probable drug transport ATP-binding protein ABC transporter [ATM1 ABC siderophor-iron transporter] | 7 | 9 |
| Rv2780 | ald | 371 | secreted L-alanine dehydrogenase ALD (40 kDa antigen) (TB4.3, cell associated pyridine nucleotide transhydrogenase) | 7 | 9 |
| Rv2620c | | 141 | probable conserved transmembrane protein | 7 | 8 |
| Rv1793 | esxN | 94 | putative ESAT-6 like protein (ESXN, ESAT-6 like protein 5) | 6 | 9 |

[a]NCBI annotation is based on Accession # AL123456 (NC_000962); updated annotation is based on bioinformatic analyses, data from MTB-related servers and experimental evidence.

The list of 45 high-ranking antigens were classified according to the following classes:

DosR regulon genes (Voskuil et al., 2003, J. Exp Med 198(5):705-713; Voskuil et al. 2004, Tuberculosis 84, 218-227)
Resuscitation genes
Reactivation genes (essentially according to Talaat et al., 2007, Proc. Natl. Acad. Sci. 189(21):7877-7886)
Classical genes
Others (mainly involved in persistence and stress response)
Some of the antigens appear in more than one class in Table 3.

TABLE 3

Top-ranking antigens sorted by qualitative and quantitative scores

| No. | Gene (Name) | Size | NCBI Annotation [Updated annotation][a] | Score (Qual) | Score (Quant) | Class/Phase |
|---|---|---|---|---|---|---|
| GROUP 1 | | | | | | |
| Rv1738 | | 94 | hypothetical protein | 9 | 14 | DosR |
| Rv2450c | rpfE | 172 | probable resuscitation-promoting factor rpfE [transglycosylase] | 9 | 14 | Resuscitation |
| Rv2623 | TB31.7 | 297 | hypothetical protein TB31.7 [USP] | 9 | 14 | DosR |
| Rv1009 | rpfB | 362 | possible resuscitation-promoting factor rpfB [transglycosylase, C5 adhesion domain] | 9 | 13 | Reactivation Resuscitation |
| Rv0867c | rpfA | 407 | possible conserved trans-membrane protein [transglycosylase, rpfA] | 9 | 12 | Reactivation Resuscitation |
| Rv2031c | acr (α-crystallin) | 144 | heat-shock protein HspX (α-crystallin homolog) 14 kDa antigen Hsp 16.3 | 8 | 14 | DosR |
| Rv1886c | fbpB (Ag85B) | 325 | secreted antigen 85-B FBPB (85-B) (mycolyl-transferase 85B) | 8 | 14 | Classical |
| Rv0288 | esxH (TB10.4) | 96 | low MW protein antigen 7 esxH (10 kDa antigen) CFP-7, TB10.4) | 8 | 13 | Reactivation |
| Rv2032 | acg | 331 | conserved hypothetical protein Acg [nitroreductase] | 8 | 13 | DosR |
| Rv2626c | | 143 | hypothetical protein [CBS pair-binding/regulation, euk] | 8 | 13 | DosR |
| Rv3873 | PPE68 | 368 | PPE family protein [PPE68, RD1 T/B immunogen] | 8 | 13 | Others |
| Rv2005c | | 295 | hypothetical protein [USP-like] | 8 | 12 | DosR |
| Rv3127 | | 344 | hypothetical protein [possible nitroreductase] | 8 | 12 | DosR |
| GROUP II | | | | | | |
| Rv1733c | | 210 | probable conserved trans-membrane protein | 8 | 11 | DosR |
| Rv1996 | | 317 | hypothetical protein [USP] | 8 | 10 | DosR |
| Rv2389c | rpfD | 154 | probable resuscitation-promoting factor rpfD [transglycosylase] | 8 | 10 | Resuscitation |
| Rv0685 | Tuf | 396 | elongation factor Tu [iron-regulated] | 8 | 9 | Reactivation |
| Rv2628 | | 120 | hypothetical protein | 8 | 9 | DosR |
| Rv1980c | mpb64 | 228 | immunogenic protein MPT64 | 7 | 13 | Classical |
| Rv3804c | fbpA (Ag85A) | 338 | secreted antigen 85-A FBPA (85-A) (mycolyl-transferase 85A) | 7 | 13 | Classical |
| Rv0079 | | 273 | hypothetical protein | 7 | 11 | DosR |
| Rv3130c | [tgs1] | 463 | hypothetical protein [diacylglycerol acyltransferase] | 7 | 11 | DosR |
| Rv3131 | [nfnB] | 332 | hypothetical protein [possible nitroreductase NfnB] | 7 | 11 | DosR |
| Rv0824c | desA1 | 389 | probable acyl[-acyl-carrier-desaturase desA1] | 7 | 10 | Reactivation |
| Rv1908c | katG | 740 | catalase-peroxidase-peroxinitritase-T katG | 7 | 10 | Others |
| Rv1174c | [sak5] | 110 | Low Mw T-cell antigen TB8.4 [secretion antigen SA5K] | 7 | 9 | Others |

TABLE 3-continued

Top-ranking antigens sorted by qualitative and quantitative scores

| No. | Gene (Name) | Size | NCBI Annotation [Updated annotation][a] | Score (Qual) | Score (Quant) | Class/Phase |
|---|---|---|---|---|---|---|
| Rv1349 | [irtB] | 579 | probable drug transport ATP-binding protein ABC transporter [ATM1 ABC siderophore-iron transporter] | 7 | 9 | Others |
| Rv1813c | | 143 | hypothetical protein | 7 | 9 | DosR |
| Rv2006 | otsB1 | 1327 | probable trehalose-6-phosphate phosphatase OSTB1 | 7 | 9 | DosR |
| Rv2029c | pfkB | 339 | possible phosphofructokinase (pfkB) | 7 | 9 | DosR |
| Rv2627c | | 413 | hypothetical protein [serine endopeptidase] | 7 | 9 | DosR |
| Rv2780 | ald | 371 | secreted L-alanine dehydrogenase ald (40 kDa antigen, TB43) | 7 | 9 | Others |
| GROUP III | | | | | | |
| Rv1884c | rpfC | 176 | probable resuscitation-promoting factor rpfC [transglycosylase] | 7 | 8 | Resuscitation |
| Rv2620c | | 141 | probable conserved transmembrane protein | 7 | 8 | Others |
| Rv2744c | 35kd-Ag [pspA] | 270 | conserved 35 kDa alanine-rich protein [phage-shock protein IM30] | 7 | 8 | Reactivation |
| Rv3875 | esxA | 95 | 6 kDA early secretory antigenic target ESXA (ESAT-6) | 6 | 11 | Classical |
| Rv1926c | mpt63 | 159 | immunogenic protein MPT63 (16 kDa immunoprotective extracellular protein) | 6 | 10 | Classical |
| Rv2030c | | 681 | hypothetical protein [putative esterase/transferase] | 6 | 10 | DosR |
| Rv3132c | devs | 578 | two component sensor histidine kinase DEVS | 6 | 10 | DosR |
| Rv3347c | PPE55 | 3157 | PPE family protein (PE55) [8 copies pentapeptide repeats] | 6 | 10 | Reactivation |
| Rv0467 | icl | 428 | isocitrate lyase(icl) [AceA] | 6 | 9 | Classical |
| Rv1130 | [prpD] | 526 | hypothetical protein [2 methyl-citrate dehydratase] | 6 | 9 | Reactivation |
| Rv1169c | PE11 | 100 | PE family protein (PE11) [triacyl glycerol lipase] | 6 | 9 | Reactivation |
| Rv1793 | esxN | 94 | putative ESAT-6-like protein ESXN (ESAT-6-like protein 5) | 6 | 9 | Others |
| Rv2629 | | 374 | hypothetical protein [peptide release factor erF1] | 6 | 9 | DosR |

[a]NCBI annotation is based on Accession # AL123456 (NC_000962); updated annotation is based on bioinformatic analyses, data from MTB-related servers and experimental evidence.

The list of 45 high-ranking antigens were sorted by the qualitative score and then by the quantitative score according to this invention and as discussed in Example 1. This method leads to 3 groups as follows:

Group I: antigens with qualitative scores 9-8, and within the antigens with a qualitative score of 8, the quantitative score cutoff is 12.

Group II: antigens with qualitative scores 8-7, the quantitative score cutoff of 7 is 9.

Group III: antigens with qualitative score 7-6, the quantitative score cutoff of 6 is 9. Antigens with more than 5 transmembrane segments were removed from the list.

In general, at least one such antigen will be overexpressed and several different antigens may be overexpressed. For example, about 1-20 or more of such antigens, or alternatively about 19, 18, 17, 16, 15, 14, 13, 12, 11, 10, 9, 8, 7, 6, 5, 4, 3, 2, or only 1 of such antigens will be overexpressed by the rBCG. Further, multiple copies of one or more of the antigens may be encoded and overexpressed in the rBCG. The amino acid sequences of selected antigens, and the nucleic acid sequences that encode them, are depicted in FIGS. 5A-B to 25A-B.

In addition, the rBCG contains nucleic acid sequences comprising one or more genes that encodes and overexpresses at least one Mtb resuscitation/reactivation antigen. Those of skill in the art will be aware that the precise definition of "resuscitation" and "reactivation" antigens may vary somewhat within the field, and in some cases, the definitions may overlap. For the purposes of the invention, it is not necessary to separate resuscitation and reactivation antigens as all are identified as being of significance in the outgrowth of Mtb from the latent state. In the most accurate sense, resuscitation antigens (i.e. resuscitation promoting factors) are a subset of reactivation antigens defined as having significant sequence or functional homology to the resuscitation promoting factor of *Micrococcus luteus* (G Mukamolova et al, Archives of Microbiology, Volume 172, 1999). For the purposes of the present application, a "reactivation" antigen is a protein expressed by *M. tuberculosis* which elicits an immune response in humans with active tuberculosis but not latent Mtb infection. They may also be identified as immunogens expressed by Mtb during outgrowth from a non-replicative stationary phase in the Wayne model of latent tuberculosis. This may include molecules that are expressed during the emergence of Mtb from the dormant latent state into active tubercle bacilli. Examples of suitable reactivation/resuscitation antigens include Rv0867c, Rv0288, Rv1009, Rv0685, Rv0824c, Rv2744c, Rv3347c, Rv1130, Rv1169c, Rv1009, Rv1884c, Rv2389c, and Rv2450c. In a preferred embodiment, the reactivation/resuscitation antigens expressed are Rv0867c, Rv1884c, and Rv2389c.

In addition, in the rBCG of the invention the genes of the DosR (Dormancy Survival Regulator) regulon, or a portion thereof, are upregulated and expressed. The entire regulon may be upregulated, or a suitable portion thereof. For example, genes that encode antigens that are recognized by individuals with latent TB may be the most suitable for upregulation. Examples of DosR upregulated antigens include Rv1738, Rv2623, Rv2031c, Rv2032, Rv2626c, Rv2005c, Rv3127, Rv1733c, Rv1996, Rv2628, Rv0079, Rv3130c, Rv3131, Rv1813c, Rv2006, Rv2029c, Rv2627c, Rv2030c, Rv3132c, and Rv2629. It is noteworthy that some overlap exists between latency and reactivation antigens, possibly reflecting the extended presence of latency related antigens in previously dormant organisms re-entering an active growth phase or their function in both the dormant and actively replicating state after reactivation in the mammalian host. Antigens that may be considered to overlap between latency and reactivation are listed in Table 4.

TABLE 4

Antigens that overlap latency and reactivation
Reactivation/dosR Antigens

| Rv1996 | Rv2005 | Rv2029 | Rv2623 | Rv2626 | Rv2727 |
|---|---|---|---|---|---|

By "up-regulate" we mean that expression of each of the individual genes of the regulon or their translated proteins is increased above the level at which they are expressed when the regulon is in a "repressed" state. Proteins of the DosR regulon are normally expressed at a relatively low level. Upon oxygen starvation and/or the presence of oxidative nitrogen compounds the DosS and DosT proteins of TB complex organisms autophosphorylate and transfer this phosphate to DosR. DosR then binds to discrete sequences upstream of DosR regulated genes thereby activating their transcription and upregulating this group of genes and gene products which constitute the DosR regulon. Upregulation within the practice of this invention mimics this oxygen starvation effect where the DosR genes have increased transcription.

Those of skill in the art are familiar with approaches to genetically engineering an organism in order to up-regulate selected genes of interest, or selected regulons of interest. Such approaches include but are not limited to overexpression of the regulator, introduction of mutations in the regulator or sensor which render them constitutively active, the introduction of regulators which mimic the function of the regulator in question, introduction of kinases or feedback loop products which activate the sensor or regulator, or the introduction of genes/gene products which mimic the environmental state which causes activation of the sensor or regulator. In a preferred embodiment, the DosR regulon is upregulated by over expressing the response regulator DosR (Rv3133c) of the DosRST "two component" regulatory system.

In another preferred embodiment, the vaccine includes one or more of Rv1908, Rv3873, Rv2780 and Rv1349. These are immunopotent antigens which were identified in silico and/or by experimentation.

In addition, the rBCG of the invention may encode antigens selected based on other criteria, such as demonstrated protective efficacy in an animal model or the expression of the antigen by Mtb but not BCG (J Mattow et al., Electrophoresis, 22:2936-2946, 2001, P. R. Jungblut, Molecular Microbiology, 33:1103-1117, 1999, H. J. Mollenkopf et al., Infection and Immunity, 72:6471-6479, 2004). In a preferred embodiment, the rBCG of the invention expresses Rv3407, which is normally expressed by Mtb but not BCG and has been shown to protect against tuberculosis in a mouse model.

The BCG that is genetically engineered as described herein may be of any BCG strain considered suitable, including but not limited to BCG strains $BCG_{1331}$, BCG Pasteur, BCG Tokyo, BCG Copenhagen, BCG Moreau, or BCG Moscow.

In a preferred embodiment, the strain is $BCG_{1331}$. In addition, the rBCG may be further genetically engineered to possess other traits, for example: a perfringolysin O (pfo) gene (in order to facilitate escape from the endosome); to express various selection markers such as antibiotic resistance or an auxotrophic selection marker in which a gene critical to the rBCG (e.g. for leucine or lysine synthesis) is deleted and must be complemented (e.g. by an extrachromsomal element that encodes the missing crucial gene) in order for the bacterium to survive; by deletion of genes or inhibition of the function of gene products which suppress apoptosis, etc.

In general, the rBCG of the invention is genetically engineered to overexpress selected antigens by introduction of genes encoding the antigens of interest into the chromosome of the rBCG under the transcriptional control of highly active expression control sequences, which may include those which are most active during mammalian infection. However, the genes encoding the antigens of interest could also be expressed from an extrachromosomal plasmid under the transcriptional control of highly active expression control sequences. Expression control sequences include but are not limited to promoters, ribosomal entry sites, etc.

The present invention further provides compositions for use in eliciting an immune response in and/or vaccinating a mammal. The compositions may be utilized as a vaccine against Mtb. The compositions of the invention include genetically engineered rBCG as described herein, and a pharmacologically suitable carrier. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain other adjuvants. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of rBCG in the formulations may vary. However, in general, the amount in the formulations will be from about 1-99%. The compositions may further comprise additional adjuvants, suitable examples of which include but are not limited to Seppic, Quil A, Alhydrogel, etc.

Vaccine formulation also involves studies to determine maximum bacterial viability and stability throughout the manufacturing process. This includes determination of maximum organism viability (live to dead) during culture utilizing a variety of commonly used medium for the culture of *Mycobacteria* to include the addition of glycerol, sugars, amino acids, and detergents or salts. After culture cells are harvested by centrifugation or tangential flow filtration and resuspended in a stabilizing medium that allows for protection of cells during freezing or freeze-drying process. Commonly used stabilizing agents include sodium glutamate, amino acids or amino acid derivatives, glycerol, sugars or commonly used salts. The final formulation will provide sufficient viable organisms to be delivered by intradermal, percutaneous injection, perfusion or oral delivery with sufficient stability to maintain and adequate shelf life for distribution and use.

The methods of the present invention involve administering a composition comprising the rBCG of the invention in a pharmacologically acceptable carrier to a subject, usually a human mammal. The vaccine preparations of the present invention may be administered by any of the many suitable means which are well known to those of skill in the art, including but not limited to by injection, orally, intranasally, by ingestion of a food product containing the antigen, etc. However, in a preferred embodiment, the mode of administration is intradermal injection. In addition, the compositions may be administered alone or in combination with other medicaments or immunogenic compositions, e.g. as part of a multi-component vaccine. Further, administration may be a single event, or multiple booster doses may be administered at various timed intervals to augment the immune response. In one embodiment, the vaccine preparation of the invention is used for an initial immunization, and the individual receiving the initial vaccine is then "boosted" with one or more different vaccine compositions, e.g. a known attenuated BCG vaccine. Alternatively, an individual may be vaccinated with another vaccine preparation and boosted one or more times with the vaccine preparation of the present invention. In some embodiments of the invention, the boosting compositions include nucleic acids encoding one or more Mtb antigens, for example: i) one or more antigens such as Rv1738, Rv2623, Rv2031c, Rv2032, Rv2626c, Rv2005c, Rv3127, Rv1733c, Rv1996, Rv2628, Rv0079, Rv3130c, Rv3131, Rv1813c, Rv2006, Rv2029c, Rv2627c, Rv2030c, Rv2629, Rv2450c, Rv1009, Rv0867c, Rv2389c, Rv1884c, Rv0288, Rv0685, Rv0824c, Rv2744, Rv3347c, Rv1130, Rv1169c, Rv1886, Rv1980c, Rv3804c, Rv3875, Rv1926c, Rv0467, Rv3873, Rv1908c, Rv1174c, Rv2780, Rv2620c, Rv1793, Rv1349 and Rv3132; ii) one or more antigens such as Rv1996, Rv2005, Rv2029, Rv2623, Rv2626 and Rv2727; iii) one or more antigens such as Rv2626, Rv1738, Rv2623, Rv1733, Rv2032, Rv3131, Rv3127, Rv3130c, Rv3804c and Rv1886c; and iv) one or more antigens including at least one of a dosR antigen, a reactivation antigen and/or a resuscitation antigen e.g., one antigen from each stage (latency, reactivation and resuscitation) of the life cycle of *M. tuberculosis*.

A particular advantage of the vaccine preparation of the present invention is that administration may be prophylactic, i.e. before exposure to the bacteria has occurred, or is suspected to have occurred, or after the fact, i.e. after a known or suspected exposure, or therapeutically, e.g. after the occurrence of disease symptoms associated with bacterial infection. This is because antigens that are involved in Mtb life cycle or infection and disease processes such as resuscitation and reactivation are included in the vaccine. Thus, the vaccine is useful not only for preventing the initial establishment of an Mtb infection, but also for preventing the reactivation of a latent Mtb infection.

Prior to administration to humans as a vaccine, the genetically engineered rBCG strains of the present are tested according to methods that are well-known to those of skill in the art. For example, tests for toxicity, virulence, safety, etc. are carried out in suitable animal models, e.g. in mice, guinea pigs, etc., some of which are immunocompromised. The ability of the vaccine preparations to elicit an immune response is likewise typically tested in suitable animal models, e.g. mice, guinea pigs, etc. In addition, protection studies involving vaccination, boosting, and subsequent challenge with live Mtb may be carried out using suitable animal models such as mice, guinea pigs, and non-human primates. Finally, those of skill in the art are familiar with the arrangements for carrying out clinical trials in consenting humans, in order to test the efficacy of the vaccine preparations. For details, see, for example, United States patent application 20060121054 (Sun et al.) published Jun. 8, 2006, and references cited therein.

By "eliciting an immune response" we mean that administration of the vaccine preparation of the present invention causes the synthesis of specific antibodies (at a titer in the range of 1 to $1\times10^6$, preferably $1\times10^3$, more preferable in the range of about $1\times10^3$ to about $1\times10^6$, and most preferably greater than $1\times10^6$) and/or cellular proliferation, as measured, e.g. via cellular assays in which IFN-γ production is assessed, for example, by $^3$H thymidine incorporation, or other suitable means. In a preferred embodiment, the immune response is a protective immune response, i.e. the immune response protects the vaccinated individual from future challenge with Mtb. However, those of skill in the art will recognize that a vaccine or immunostimulating preparation need not provide total protection in order to convey some benefit to a patient. For example, the preparations may elicit immune responses that slow or lessen the progress of disease symptoms, without fully eradicating them.

The following non-limiting Examples serve to illustrate the practice of this invention.

EXAMPLES

Example 1

Selection of Suitable Antigens and Design of rBCG Based on this Selection

An initial group of Mtb proteins (189 antigens, see Table 1) was selected from all possible 3989 Mtb ORFs, according to the following selection procedure:

(1) Compilation of available data for all 3989 TB ORF products: Literature scan for global analyses (e.g. up/down regulation of expression under various conditions such as hypoxia, dormancy, interaction with macrophage, location and persistence in lung tissue; iron regulation; transcriptomics and proteomics profiles; mutation leading to attenuation of virulence; potential high immune response etc.).

(2) Establishing a subset of genes by cross matching the accumulated data: Selection of antigens that demonstrate positive evidence in any two independent studies originating from different criteria mentioned above.

(3) Iterative trimming of the above subset, aiming at selecting an initial group of candidates (Table 1, 189 antigens), based on the extent of effect documented in the individual studies.

(4) Conducting bioinformatic studies for:
  a) Further characterization of the initial group of 189 candidates by domain analyses, prediction of cellular localization, inspection of genome context, identification of repeat proteins, and assignment of putative function for the unknown/hypothetical Ag (sequence similarity searches by blast against the nr database, NCBI, domain/motifs databases, and Mtb-related servers and databases: TBsgc—The TB Structural Genomics Consortium, Tuberculist—the database on *Mycobacterium tuberculosis* genetics, TBDB—an integrated platform for TB drug discovery MTBreg—The Database of Conditionally Regulated Proteins in *Mycobacterium tuberculosis* and the BioHealthBase server.
  b) Immunoinformatic analysis for prediction of human leukocyte antigen (HLA)-binding targets (by NetCTL) and experimentally documented T-cell epitopes by database (IEDB) and literature searches. Implementing various measures for the determination of epitopes as putative strong binders, and for the selection of most potent candidates according to the predictions (i.e. thresholds, and number of supertypes/population coverage).

(5) In depth literature search for data pertaining to aspects of virulence and vaccine development, for each of the 189 antigens (Table 1) and/or their orthologs.

(6) Setting up a knowledge dataset of the 189 candidates (Table 1), by integrating all literature and data analyses (steps 4&5 above).

The selected antigens in the initial group presented in Table 1, include known vaccine candidates, and proteins known to be: involved in various stages of the life cycle of Mtb (dormancy, reactivation, resuscitation); tissue specific antigens; antigens affected by starvation; and, antigens originating in genomic sequences present in a virulent Mtb strain.

The 189 candidate antigens were ranked in order of likely importance by the following 14 analyses:
1) macrophage survival/persistence;
2) up-regulation of expression by the two-component system MprAB;
3) response to hypoxia;
4) involvement in reactivation;
5) involvement in dormancy;
6) expression in lung tissue;
7) co-regulation with Rv2031 (Acr);
8) whether or not the protein is secreted;
9) the ability to act as a B-cell immunogen;
10) iron-regulated genes;
11) cell wall association or cell wall biogenesis;
12) existing vaccine efficacy data;
13) the presence of repeat domains;
14) T-cell response, determined by a) known experimental evidence (e.g. from the literature) and b) a determination that the antigen likely contains one or more T-cell epitopes as assessed by the immunoinformatics program of the Technical University of Denmark (cbs.dtu.dk/services/NetCTL);

The presence or absence of each of these traits was scored for each of the 189 genes and a qualitative score was determined and employed as a measure to rank the list of 189 antigens and choose for the 45 best hits.

The 45 candidates were then further ranked using the same 13 criteria, by assigning internal numerical scores to each of the criteria, according to the intensity of the results and/or relevance to vaccine development. A list of the top-ranking 45 antigens is given in Table 2, along with their subgrouping according to the class/phase of infection (latency/dormancy, resuscitation/reactivation, classical and others); within the classes, the antigens are sorted by their scores. Table 3 presents the 45 antigens prioritization into 3 subset groups according to their quantitative, and subsequently—qualitative scores.

Based on this analysis, final selections of groups of antigens for use in the rBCGs were made, usually based on the antigens with the highest overall scores. In addition, for the final selection, antigens were grouped according to "type" in that the rBCG includes at least 1) one or more Mtb antigens, including the so-called "classical" Mtb antigens such as 85A, 85B and TB 10.4; and
2) at least one Mtb resuscitation/reactivation antigen selected from Rv0867c, Rv1009, Rv1884c, Rv2389c, Rv2450c, Rv0867c, Rv0288, Rv1009, Rv0685, Rv0824c, Rv1349, Rv2744c, Rv3347c, Rv1130, and Rv1169c.

In addition, antigens were selected based on other criteria such as demonstrated protective efficacy in an animal model, the expression of the antigen by Mtb but not BCG, or diminished expression of the antigen in BCG (J Mattow et al., Electrophoresis, 22:2936-2946, 2001, P. R. Jungblut, Molecular Microbiology, 33:1103-1117, 1999, H. J. Mollenkopf et al, Infection and Immunity, 72:6471-6479). Such Mtb-specific antigens include Rv1511, Rv2520c, Rv3407, Rv2802c and Rv3710.

Preferred combinations of antigens to be expressed in an rBCG include the following:
1) Classical antigens Rv1886c, Rv3804c;
2) Resuscitation and Reactivation antigens Rv0867c, Rv1884c, Rv2389c; and
3) Mtb-specific antigen Rv3407.

Example 2

Construction of a Recombinant BCG Genetically Engineered to Express at Least One Classical Mtb Antigen, at Least One Mtb Resuscitation/Reactivation Antigen and in which the DosR Regulon is Upregulated Materials and Methods: General For the construction of an rBCG described in the following sections, restriction endonucleases (herein "REs"); New England Biolabs Beverly, Mass.), T4 DNA ligase (New England Biolabs, Beverly, Mass.) and Taq polymerase (Invitrogen, Carlsbad, Calif.) were used according to the manufacturers' protocols; Plasmid DNA was prepared using small-scale (Qiagen MiniprepR kit, Santa Clara, Calif.) or large-scale (Qiagen MaxiprepR kit, Santa Clara, Calif.) plasmids DNA purification kits according to the manufacturer's protocols (Qiagen, Santa Clara, Calif.); Nuclease-free, molecular biology grade Milli-Q water, Tris-HCl (pH 7.5), EDTA pH 8.0, 1M $MgCl^{-2}$, 100% (v/v) ethanol, ultra-pure agarose, and agarose gel electrophoresis buffer were purchased from Invitrogen, Carlsbad, Calif. RE digestions, PCRs, DNA ligation reactions and agarose gel electrophoresis were conducted according to well-known procedures (Sambrook, et al., Molecular Cloning: A Laboratory Manual. 1, 2, 3; 1989); (Straus, et al., Proc Natl Acad Sci USA. March; 87(5): 1889-

93; 1990). Nucleotide sequencing to verify the DNA sequence of each recombinant plasmid described in the following sections was accomplished by conventional automated DNA sequencing techniques using an Applied Biosystems automated sequencer, model 373A.

PCR primers were purchased from commercial vendors such as Sigma (St. Louis, Mo.) or synthesized using an Applied Biosystems DNA synthesizer (model 373A). PCR primers were used at a concentration of 150-250 µM and annealing temperatures for the PCR reactions were determined using Clone manager software version 4.1 (Scientific and Educational Software Inc., Durham, N.C.). PCRs were conducted in a BioRad thermocycler (BioRad, Hercules, Calif.). The PCR primers for the amplifications were designed using Clone Manager® software version 4.1 (Scientific and Educational Software Inc., Durham N.C.). The RE digestions and the PCRs were subsequently analyzed by agarose gel electrophoresis using standard procedures (Straus et al, supra 1990; and Sambrook et al., supra 1989). A positive clone is defined as one that displays the appropriate RE pattern and/or PCR pattern. Plasmids identified through this procedure were further evaluated using standard DNA sequencing procedures, as described above.

*Escherichia coli* strains, such as DH5α and Stable2$^R$, were purchased from Invitrogen (Carlsbad, Calif.) and served as initial host of the recombinant plasmids. Recombinant plasmids were introduced into *E. coli* strains by electroporation using a high-voltage eletropulse device, such as the Gene Pulser (BioRad Laboratories, Hercules, Calif.), set at 100-200≠, 15-25 µF and 1.0-2.5 kV, as described (Straus et al, supra 1990). Optimal electroporation conditions were identified by determining settings that resulted in maximum transformation rates per mcg DNA per bacterium.

*E. coli* strains are typically grown on tryptic soy agar (Difco, Detroit, Mich.) or in tryptic soy broth (Difco, Detroit, Mich.), which was made according to the manufacturer's directions. Unless stated otherwise, all bacteria were grown at 37° C. in 5% (v/v) $CO_2$ with gentle agitation. When appropriate, the media was supplemented with antibiotics (Sigma, St. Louis, Mo.). Bacterial strains were typically stored at −80° C. suspended in (Difco) containing 30% (v/v) glycerol (Sigma, St. Louis, Mo.) at ca. $10^9$ colony-forming units (herein referred to as "cfu") per ml.

Mycobacterial strains were cultured in liquid media, such as Middlebrook 7H9 or Saulton Synthetic Medium, preferably at 37° C. The strains can be maintained as static or agitated cultures. In addition, the growth rate of BCG can be enhanced by the addition of oleic acid (0.06% v/v; Research Diagnostics Cat. No. 01257) and detergents such as Tyloxapol (0.05% v/v; Research Diagnostics Cat. No. 70400). The purity of BCG cultures can be evaluated by evenly spreading 100 mcl aliquots of the BCG culture serially diluted (e.g. 10-fold steps from Neat—$10^{-8}$) in phosphate buffered saline (herein referred to PBS) onto 3.5 inch plates containing 25-30 ml of solid media, such as Middlebrook 7H10. In addition, the purity of the culture can be further assessed using commercially available medium such as thioglycolate medium (Science Lab, catalogue number 1891) and soybean-casein medium (BD, catalogue number 211768).

In order to insert the desired antigen expression cassettes into the chromosome of the perfringolysin expressing BCG1331 derivative described elsewhere, a plasmid was designed in silico and synthesized by DNA2.0 (Menlo Park, Calif.). The salient features of this vector (pJFINT) include an *E. coli* colE1 origin of replication, 3 multiple cloning sites separated by transcriptional terminators rmBT1, T2 of pEX18gm, and rnhA, the attP phage integration region of bacteriophage L5 and the integrase gene of bacteriophage L5 (GenBank #Z18946). Immediately upstream of the L5 sequence, a selectable marker cassette consisting of a kanamycin resistance allele aphA from Tn10 (GenBank #AAM97345) and a sacB gene (Genbank # NP_391325) were included. This marker cassette was flanked by direct repeats of the γΔ resolvase binding site from transposon Tn1000. This plasmid is incapable of replication in mycobacterial species and the L5 attP sequence allows for high frequency recombination with the attB region of mycobacterial chromosomes to facilitate integration of the plasmid sequence into the chromosome. The marker cassette can then be removed from the chromosome of the integrant by the introduction of γΔ resolvase and selection of markerless strains on solid media containing 10% sucrose.

An antigen expression cassette was designed in silico to encode Rv0867c, Rv1884c, and Rv2389c separated by optimized ribosomal sites under the transcriptional control of the hsp60 promoter of *Mycobacterium bovis* and synthesized by DNA2.0 (Carlsbad Calif.). A second expression cassette was similarly designed and constructed to encode Rv1886c, Rv3804c and Rv3407c under transcriptional control of the hsp60 promoter. Finally, a third cassette encoding Rv3133c (DosR) under the transcriptional control of the hsp60 promoter was designed and constructed. These three antigen expression cassettes were ligated into pJFINT such that each was separated by a transcriptional terminator (FIG. 2). The resulting plasmid, pRC108, was electroporated into *E. coli* Stable2 and the plasmid sequence of a kanamycin resistant clone was verified.

The pRC108 plasmid was isolated from a 100 ml *E. coli* culture and electroporated into a pfo expressing derivative of BCG Danish 1331. After electroporation, the cells were cultured overnight in 7H9 medium with 10% (v/v) OADC and 0.05% (v/v) of Tyloxapol supplementation and plated on 7H10 agar containing 50 ug/ml of kanamycin. As the plasmid does not encode a mycobacterial origin of replication, kanamycin resistance in all colonies tested was conferred by integration of the plasmid into the attB site of the BCG genome. Individual colonies were picked for PCR analysis and inoculated into 7H9 medium with 10% (v/v) OADC and 0.05% (v/v) tyloxapol for analysis of antigen expression. PCR characterization of the kanamycin resistant colonies demonstrated the presence of the entire plasmid sequence in the chromosome of the recombinant BCG, designated AFV-102pRC108. AFV-102pRC108 cultures were washed with 7H9 and used to inoculate protein-free 7H9 tyloxapol cultures. Supernatants of the AFV-102pRC108 cultures were harvested by centrifugation and immunoblotted with rabbit polyclonal antisera to the transglycolase domain of the Rpf protein. Rv1009, which is cross reactive with the transglycosylase domains of all Rpf's or rabbit polyclonal antisera raised against peptides of Rv0867c. This demonstrated the enhanced production of Rv0867c, Rv1884c, and Rv2389c above the background of the BCG homologs of these proteins (FIG. 3A). This supernatant was similarly immunoblotted with rabbit polyclonal antisera to Ag85 complex and the overexpression of Rv1886c and Rv3804c was observed (FIG. 3B). The cell pellet was immunoblotted with rabbit polyclonal antisera to Rv3407 and the expression of Rv3407, the homolog of which is normally silent in BCG, was confirmed (FIG. 3C). Cell pellets were also immunoblotted with DosR-specific rabbit polyclonal antisera to demonstrate the overexpression of DosR itself and with rabbit antisera to Rv1733c to demonstrate the upregulation of a DosR regulated protein (FIG. 3D).

In order to complete the construction of this vaccine to make it suitable for human use, the marker cassette of the integrated plasmid was then removed. Electrocompetent AFV-102pRC108 cells were electroporated with plasmid pYUB870hyg, which encodes the γΔ resolvase of Tn1000, a sacB allele, and a hygromycin resistance gene (GenBank #ABD64366). Transformants resistant to both kanamycin and hygromycin were selected on 7H10 media and inoculated into 7H9 liquid media with 10% (v/v) OADC and 0.05% (v/v) tyloxapol and no antibiotics. After seven days growth, dilutions of these liquid cultures were plated on 7H10 containing 10% sucrose to select for recombinants from which the aphA-sacB marker has been excised and the pYUB870hyg plasmid has been lost by dilution and selection against the sacB allele.

Sucrose-resistant transformants were picked for PCR analysis of the integrated antigen cassettes and were inoculated into 7H9 liquid media for immunoblot analysis as before. PCR analysis revealed that the antigen expression cassettes were still present in the chromosome and that the hygromycin resistance marker and sacB gene had been excised. Immunoblotting of supernatants and cell pellets with antisera to Rpf, Ag85 complex, Rv3407, and DosR confirmed that excision of the marker cassette from the chromosome did not effect the expression of the inserted antigen cassettes.

Strain AERAS-407 was constructed by removal of the anti-biotic resistance marker from AFV-102pRC108.

Example 3

Demonstration of the Immunogenicity and Protection Elicited by Vaccination with AERAS-407 in Mice To illustrate the immune responses elicited by AERAS-407 and to demonstrate its protective efficacy against tuberculosis, four groups of 10 C57/BL6 mice are vaccinated subcutaneously with either 1) saline, 2) BCG, 3) BCG-PfoA or 4) AERAS-407. Mice in groups 2, 3, and 4 receive $5\times10^5$ cfu of BCG or recombinant BCG. After 10 weeks, five mice from each group are sacrificed for immune assays and the remaining animals are challenged with 100 cfu aerosolized *M. tuberculosis* Erdman.

To measure humoral immune responses, a peptide microarray chip has been designed. The chip is spotted with overlapping 50 amino acid peptides generated from the sequences of Rv1886c, Rv3804c, Rv3407c, Rv0867c, Rv1884c, Rv2389c, Rv3133c, and all BCG encoded DosR-regulated proteins which are at least 2 fold induced by the overexpression of DosR (i.e. DosR regulated genes for which transcription is at least 2 fold greater in BCG constitutively expressing the DosR regulon than the wild-type parent strains under aerobic conditions). Pooled sera from each group is incubated with 3 peptide chips for 1 hr at 37° C. The chips are then washed with phosphate-buffered saline (PBS) pH7.2 and incubated with fluorescein isothiocyanate (FITC) conjugated goat anti-mouse IgG sera (Abcam, Cambridge, Mass.) for 1 hour at 37° C. The chips are then washed again with PBS and the immunofluorescence is read with a Genepix 4000B Array Scanner (Molecular Devices, Sunnyvale, Calif.). Values for each peptide spot are averaged for the 3 chips in each group. Mice receiving AERAS-407 show greater antibody responses to peptides derived from Rv1886c, Rv3804c, Rv3407c, Rv0867c, Rv1884c, Rv2389c and DosR regulated proteins than unvaccinated mice or mice vaccinated with BCG or BCG-PfoA.

To measure cellular immune responses elicited by AERAS-407, spleens are harvested from each and homogenized. Splenocyte concentrations are adjusted to $5\times10^5$ cells/well in R10 media in multichamber plates and are incubated for 3 days at 37° C. with purified Rv1886c, Rv3804c, Rv3407c, Rv0867c, Rv1884c, or Rv2389c at a concentration of 1 μg/ml. In addition, splenocytes from each mouse are incubated with Rv2623 and Rv3130c as these proteins are known to be highly upregulated in DosR overexpressing strains and are known to be potent T cell immunogens. After the 3 day incubation, supernatants are harvested from the splenocyte cultures and assayed by ELISA for interferon-γ produced in response to antigen stimulation. Control cultures of unstimulated splenocytes or PMA/PHA stimulated splenocytes are included as negative and positive controls, respectively.

To quantify protection afforded by vaccination with AERAS-407, the 5 remaining mice from each group are sacrificed 10 weeks after challenge with *M. tuberculosis* and lungs and spleens are aseptically harvested from each animal. Lungs and spleens are homogenized in PBS and dilutions are plated on 7H10 agar. After 4 weeks of incubation, the number of *M. tuberculosis* colonies are enumerated for each animals lungs and spleen and corrected for the dilution factor. This value is the number of live tubercle bacilli present in the lungs and spleen of each animal. BCG vaccination typically results in approximately a 1 log reduction in cfu/lung and spleen versus saline vaccination. AERAS-407 vaccination results in a greater reduction of Mtb load in the lungs and spleens of mice.

Example 4

Construction of a Second Recombinant BCG Vaccine Genetically Engineered to Over Express Selected Classical *M. tb* Antigens and the DosR Regulon A second combination of antigens (TB10.4, Ag85B, Ag85A and Rv3407) was also overexpressed in the rBCG AFV102 strain by integration into the chromosome at the attB site. This was carried out in a manner similar to that described in Example 2 for the Aeras 407 construct. To integrate this second antigen set, the integration plasmid pAF707 (depicted schematically in FIG. 4) was constructed as described for pJFINT in Example 2 except for the following differences: a hygromycin resistance gene was used in place of the kanamycin resistance gene, and the PBlaf promoter was used to drive antigens TB10.4, Ag85B, Ag85A and Rv3407 for over expression in the order listed. All other general materials and methods were similar to those described in Example 2. The resultant strain was designated Aeras 406. The final strain was further analyzed by PCR followed by sequencing analysis and confirmed to have the desired genotype. The strain was further demonstrated to overexpress the selected antigens by SDS-PAGE analysis and immunoblot testing as described in Example 2 (data not shown).

Example 5

Protection of Non-Human Primates from Tuberculosis by Vaccination with AERAS-407

The protective efficacy of AERAS-407, particularly in relation to the enhanced capacity to prevent latent infection and reactivation of disease, is best tested in rhesus macaques as mice do not create granulomatous latent foci as humans and other primates do. To evaluate the protective efficacy of AERAS-407 in NHP's, four groups of six weight and sexmatched rhesus macaques are vaccinated with 1) saline, 2) BCG 1331, 3) BCG-Pfo, or 4) AERAS-407. Each animal in groups 2-4 receives 5×10$^5$ cfu of the respective BCG or rBCG by intradermal injection. Fifteen weeks after vaccination, all animals are challenged by bronchial installation of approximately 300 cfu of *M. tuberculosis* Erdman. All animals are evaluated monthly for six months for clinical symptoms of tuberculosis by chest X-ray, weight, feeding, cough, lethargy, and immune responses to TB specific proteins. All animals that die during the six month observation period are necropsied and tissue pathology and Mtb burden by organ is measured as in Example 3. All moribund animals are humanely euthanized and similarly examined. Six months post-challenge all surviving animals are euthanized and necropsied for tissue pathology and Mtb burden in lungs, liver and spleen. AERAS-407 vaccination results in decreased mortality, decreased tissue damage and lower counts of viable Mtb organisms in the lungs of experimentally infected animals.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

---

We claim:

1. A method for immunizing a subject against infection by *Mycobacterium tuberculosis* (Mtb) or for eliciting an immune response to Mtb in said subject or for preventing a recurrence of symptoms of tuberculosis in a patient with a latent Mtb, comprising the step of
administering to said subject a composition comprising a recombinant Bacille Calmette-Guerin (BCG) comprising
at least one DosR regulon gene that is up-regulated, and
at least two nucleic acid sequences which are different from each other, each of which encode one or more genes that are overexpressed, said at least two nucleic acid sequences including
i) a first nucleic acid sequence encoding at least one *Mycobacterium tuberculosis* (Mtb) antigen; and
ii) a second nucleic acid sequence encoding at least one Mtb reactivation antigen that is not a DosR antigen.

2. The method of claim 1, further comprising the step of administering a boosting composition at timed intervals to augment said immune response, said boosting composition comprising said one or more Mtb antigens identical to those administered initially, or one or more Mtb antigens different from those administered initially.

3. The method of claim 2, wherein said one or more antigens is selected from the group consisting of Rv1738, Rv2623, Rv2031c, Rv2032, Rv2626c, Rv2005c, Rv3127, Rv1733c, Rv1996, Rv2628, Rv0079, Rv3130c, Rv3131, Rv1813c, Rv2006, Rv2029c, Rv2627c, Rv2030c, Rv2629, Rv2450c, Rv1009, Rv0867c, Rv2389c, Rv1884c, Rv0288, Rv0685, Rv0824c, Rv2744, Rv3347c, Rv1130, Rv1169c, Rv1886, Rv1980c, Rv3804c, Rv3875, Rv1926c, Rv0467, Rv3873, Rv1908c, Rv1174c, Rv2780, Rv2620c, Rv1793, Rv1349 and Rv3132.

4. The method of claim 2, wherein said one or more antigens is selected from the group consisting of Rv1996, Rv2005, Rv2029, Rv2623, Rv2626 and Rv2727.

5. The method of claim 2, wherein said one or more antigens is selected from the group consisting of Rv2626, Rv1738, Rv2623, Rv1733, Rv2032, Rv3131, Rv3127, Rv3130c, Rv3804c and Rv1886c.

6. The method of claim 2, wherein said one or more antigens include at least one antigen from each of the following stages of the life cycle of Mtb: latency, reactivation, and resuscitation stages.

7. The method of claim 1
wherein a first nucleic acid sequence of said at least two nucleic acid sequence encodes an antigen selected from the group consisting of Rv2450c, Rv1009, Rv0867c, Rv2389c, Rv1884c, Rv0288, Rv0685, Rv0824c, Rv2744, Rv3347c, Rv1130, Rv1169c; and
wherein a second nucleic acid sequence of said at least two nucleic acid sequences encodes an antigen selected from the group consisting of Rv1738, Rv2623, Rv2031c, Rv2032, Rv2626c, Rv2005c, Rv3127, Rv1733c, Rv1996, Rv2628, Rv0079, Rv3130c, Rv3131, Rv1813c, Rv2006, Rv2029c, Rv2627c, Rv2030c, Rv2629, Rv2450c, Rv1009, Rv0867c, Rv2389c, Rv1884c, Rv0288, Rv0685, Rv0824c, Rv2744, Rv3347c, Rv1130, Rv1169c, Rv1886, Rv1980c, Rv3804c, Rv3875, Rv1926c, Rv0467, Rv3873, Rv1908c, Rv1174c, Rv2780, Rv2620c, Rv1793, Rv1349 and Rv3132.

* * * * *

UNITED STATES PATENT AND TRADEMARK OFFICE
CERTIFICATE OF CORRECTION

PATENT NO. : 8,361,482 B2  Page 1 of 1
APPLICATION NO. : 12/618037
DATED : January 29, 2013
INVENTOR(S) : Avigdor Shafferman et al.

It is certified that error appears in the above-identified patent and that said Letters Patent is hereby corrected as shown below:

Title page, Item [75], Inventors should read:

--[75] Inventors: Avigdor Shafferman, Ness Ziona (IL); Anat Zvi, Gedera (IL); Naomi Ariel, Ness Ziona (IL); John Fulkerson, Silver Spring, MD (US); Ronggai Sun, Ellicott City, MD (US); Rosemary Chang, Bethesda, MD (US); Jerald C. Sadoff, Washington, DC (US).--

Signed and Sealed this
Twelfth Day of May, 2015

Michelle K. Lee
*Director of the United States Patent and Trademark Office*

SEQUENCE LISTING

<160> NUMBER OF SEQ ID NOS: 40

<210> SEQ ID NO 1
<211> LENGTH: 338
<212> TYPE: PRT
<213> ORGANISM: Mycobacterium tuberculosis

<400> SEQUENCE: 1

```
Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
                20                  25                  30

Gly Ala Val Gly Gly Thr Ala Thr Ala Gly Ala Phe Ser Arg Pro Gly
            35                  40                  45

Leu Pro Val Glu Tyr Leu Gln Val Pro Ser Pro Ser Met Gly Arg Asp
        50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
    210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270
```

-continued

```
Glu Gly Phe Val Arg Thr Ser Asn Ile Lys Phe Gln Asp Ala Tyr Asn
        275                 280                 285

Ala Gly Gly His Asn Gly Val Phe Asp Phe Pro Asp Ser Gly Thr
    290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
            325                 330                 335

Gly Ala

<210> SEQ ID NO 2
<211> LENGTH: 1017
<212> TYPE: DNA
<213> ORGANISM: Mycobacterium tuberculosis

<400> SEQUENCE: 2
atgcagcttg ttgacagggt tcgtggcgcc gtcacgggta tgtcgcgtcg actcgtggtc    60
ggggccgtcg gcgcggccct agtgtcgggt ctggtcggcg ccgtcggtgg cacggcgacc   120 gcggggcat tttcccggcc gggcttgccg gtggagtacc tgcaggtgcc gtcgccgtcg    180
atgggccgtg acatcaaggt ccaattccaa agtggtggtg ccaactcgcc cgccctgtac   240
ctgctcgacg gcctgcgcgc gcaggacgac ttcagcggct gggacatcaa caccccggcg   300
ttcgagtggt acgaccagtc gggcctgtcg gtggtcatgc cggtgggtgg ccagtcaagc   360
ttctactccg actggtacca gcccgcctgc ggcaaggccg gttgccagac ttacaagtgg   420
gagaccttcc tgaccagcga gctgccgggg tggctgcagg ccaacaggca cgtcaagccc   480
accggaagcg ccgtcgtcgg tctttcgatg gctgcttctt cggcgctgac gctggcgatc   540
tatcaccccc agcagttcgt ctacgcggga gcgatgtcgg gcctgttgga ccctcccag   600 gcgatgggtc ccaccctgat cggcctggca atgggtgacg ctggcggcta caaggcctcc   660
gacatgtggg gcccgaagga ggacccggcg tgcagcgca acgacccgct gttgaacgtc   720
gggaagctga tcgccaacaa caccccgcgtc tgggtgtact gcggcaacgg caagccgtcg   780
gatctgggtg gcaacaacct gccggccaag ttcctcgagg gcttcgtgcg accagcaac   840 atcaagttcc aagacgccta caacgccggt ggcggccaca acggcgtgtt cgacttcccg   900
gacagcggta cgcacagctg ggagtactgg ggcgcgcagc tcaacgctat gaagcccgac   960
ctgcaacggg cactgggtgc cacgcccaac accgggcccg cgccccaggg cgcctag    1017

<210> SEQ ID NO 3
<211> LENGTH: 325
<212> TYPE: PRT
<213> ORGANISM: Mycobacterium tuberculosis

<400> SEQUENCE: 3

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
```

```
                85                  90                  95
Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
    130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
                325

<210> SEQ ID NO 4
<211> LENGTH: 978
<212> TYPE: DNA
<213> ORGANISM: Mycobacterium tuberculosis

<400> SEQUENCE: 4
atgacagacg tgagccgaaa gattcgagct tggggacgcc gattgatgat cggcacggca    60
gcggctgtag tccttccggg cctggtgggg cttgccggcg gagcggcaac cgcgggcgcg   120
ttctcccggc cggggctgcc ggtcgagtac ctgcaggtgc cgtcgccgtc gatgggccgc   180
gacatcaagg ttcagttcca gagcggtggg aacaactcac ctgcggttta tctgctcgac   240
ggcctgcgcg cccaagacga ctacaacggc tgggatatca acaccccggc gttcgagtgg   300
tactaccagt cgggactgtc gatagtcatg ccggtcggcg gcagtccag cttctacagc    360 gactggtaca gcccggcctg cggtaaggct ggctgccaga cttacaagtg gaaaccttc    420 ctgaccagcg agctgccgca atggttgtcc gccaacaggg ccgtgaagcc caccggcagc   480
gctgcaatcg gcttgtcgat ggccggctcg tcggcaatga tcttggccgc ctaccacccc   540
cagcagttca tctacgccgg ctcgctgtcg gccctgctgg accctctcca ggggatgggg   600
cctagcctga tcggcctcgc gatgggtgac gccggcggtt acaaggccgc agacatgtgg   660
ggtccctcga gtgacccggc atgggagcgc aacgacccta cgcagcagat ccccaagctg   720
gtcgcaaaca acacccggct atgggtttat tgcgggaacg gcaccccgaa cgagttgggc   780
```

```
ggtgccaaca tacccgccga gttcttggag aacttcgttc gtagcagcaa cctgaagttc      840
caggatgcgt acaacgccgc gggcgggcac aacgccgtgt caacttccc gcccaacggc       900 acgcacagct gggagtactg gggcgctcag ctcaacgcca tgaagggtga cctgcagagt      960
tcgttaggcg ccggctga                                                    978
```

<210> SEQ ID NO 5
<211> LENGTH: 407
<212> TYPE: PRT
<213> ORGANISM: Mycobacterium tuberculosis

<400> SEQUENCE: 5

```
Met Ser Gly Arg His Arg Lys Pro Thr Thr Ser Asn Val Ser Val Ala
1               5                   10                  15

Lys Ile Ala Phe Thr Gly Ala Val Leu Gly Gly Gly Ile Ala Met
            20                  25                  30

Ala Ala Gln Ala Thr Ala Ala Thr Asp Gly Glu Trp Asp Gln Val Ala
        35                  40                  45

Arg Cys Glu Ser Gly Gly Asn Trp Ser Ile Asn Thr Gly Asn Gly Tyr
    50                  55                  60

Leu Gly Gly Leu Gln Phe Thr Gln Ser Thr Trp Ala Ala His Gly Gly
65                  70                  75                  80

Gly Glu Phe Ala Pro Ser Ala Gln Leu Ala Ser Arg Glu Gln Gln Ile
                85                  90                  95

Ala Val Gly Glu Arg Val Leu Ala Thr Gln Gly Arg Gly Ala Trp Pro
            100                 105                 110

Val Cys Gly Arg Gly Leu Ser Asn Ala Thr Pro Arg Glu Val Leu Pro
        115                 120                 125

Ala Ser Ala Ala Met Asp Ala Pro Leu Asp Ala Ala Val Asn Gly
    130                 135                 140

Glu Pro Ala Pro Leu Ala Pro Pro Ala Asp Pro Ala Pro Pro Val
145                 150                 155                 160

Glu Leu Ala Ala Asn Asp Leu Pro Ala Pro Leu Gly Glu Pro Leu Pro
                165                 170                 175

Ala Ala Pro Ala Asp Pro Ala Pro Pro Ala Asp Leu Ala Pro Pro Ala
            180                 185                 190

Pro Ala Asp Val Ala Pro Val Glu Leu Ala Val Asn Asp Leu Pro
        195                 200                 205

Ala Pro Leu Gly Glu Pro Leu Pro Ala Ala Pro Ala Asp Pro Ala Pro
    210                 215                 220

Pro Ala Asp Leu Ala Pro Pro Ala Pro Ala Asp Leu Ala Pro Pro Ala
225                 230                 235                 240

Pro Ala Asp Leu Ala Pro Pro Ala Pro Ala Asp Leu Ala Pro Pro Val
                245                 250                 255

Glu Leu Ala Val Asn Asp Leu Pro Ala Pro Leu Gly Glu Pro Leu Pro
            260                 265                 270

Ala Ala Pro Ala Glu Leu Ala Pro Pro Ala Asp Leu Ala Pro Ala Ser
        275                 280                 285

Ala Asp Leu Ala Pro Pro Ala Pro Ala Asp Leu Ala Pro Pro Ala Pro
    290                 295                 300

Ala Glu Leu Ala Pro Pro Ala Pro Ala Asp Leu Ala Pro Pro Ala Ala
305                 310                 315                 320

Val Asn Glu Gln Thr Ala Pro Gly Asp Gln Pro Ala Thr Ala Pro Gly
                325                 330                 335
```

-continued

```
Gly Pro Val Gly Leu Ala Thr Asp Leu Glu Leu Pro Glu Pro Asp Pro
            340                 345                 350

Gln Pro Ala Asp Ala Pro Pro Gly Asp Val Thr Glu Ala Pro Ala
        355                 360                 365

Glu Thr Pro Gln Val Ser Asn Ile Ala Tyr Thr Lys Lys Leu Trp Gln
370                 375                 380

Ala Ile Arg Ala Gln Asp Val Cys Gly Asn Asp Ala Leu Asp Ser Leu
385                 390                 395                 400

Ala Gln Pro Tyr Val Ile Gly
                405

<210> SEQ ID NO 6
<211> LENGTH: 1224
<212> TYPE: DNA
<213> ORGANISM: Mycobacterium tuberculosis

<400> SEQUENCE: 6
atgagtggac gccaccgtaa gcccaccaca tccaacgtca gcgtcgccaa gatcgccttt      60
accggcgcag tactcggtgg cggcggcatc gccatggccg ctcaggcgac gcggccacc     120 gacggggaat gggatcaggt ggcccgctgc gagtcgggcg gcaactggtc gatcaacacc     180
ggcaacggtt acctcggtgg cttgcagttc actcaaagca cctgggccgc catggtggc     240 ggcgagttcg ccccgtcggc tcagctggcc agccgggagc agcagattgc cgtcggtgag     300
cgggtgctgg ccacccaggg tcgcggcgcc tggccggtgt gcggccgcgg gttatcgaac     360
gcaacacccc gcgaagtgct tcccgcttcg cagcgatgg acgctccgtt ggacgcggcc     420
gcggtcaacg gcgaaccagc accgctggcc ccgccgcccg ccgacccggc gccacccgtg     480
gaacttgccg ctaacgacct gcccgcaccg ctgggtgaac ccctcccggc agctcccgcc     540
gacccggcac caccgccgga cctggcacca cccgcgcccg ccgacgtcgc gccacccgtg     600
gaacttgccg taaacgacct gcccgcaccg ctgggtgaac ccctcccggc agctcccgcc     660
gacccggcac caccgccgga cctggcacca cccgcgcccg ccgacctggc gccacccgcg     720
cccgccgacc tggcgccacc cgcgcccgcc gacctggcac acccgtgga acttgccgta     780 aacgacctgc ccgcgccgct gggtgaaccc ctcccggcag ctcccgccga actggcgcca     840
cccgccgatc tggcacccgc gtccgccgac ctggcgccac ccgcgcccgc cgacctggcg     900
ccacccgcgc cgccgaact ggcgccaccc gcgcccgccg acctggcacc acccgctgcg     960
gtgaacgagc aaaccgcgcc gggcgatcag cccgccacag ctccaggcgg cccggttggc    1020
cttgccaccg atttggaact ccccgagccc gaccccaac cagctgacgc accgccgccc    1080
ggcgacgtca ccgaggcgcc cgccgaaacg ccccaagtct cgaacatcgc ctatacgaag    1140
aagctgtggc aggcgattcg ggcccaggac gtctgcggca acgatgcgct ggactcgctc    1200
gcacagccgt acgtcatcgg ctga                                            1224

<210> SEQ ID NO 7
<211> LENGTH: 362
<212> TYPE: PRT
<213> ORGANISM: Mycobacterium tuberculosis

<400> SEQUENCE: 7

Met Leu Arg Leu Val Val Gly Ala Leu Leu Leu Val Leu Ala Phe Ala
1               5                   10                  15

Gly Gly Tyr Ala Val Ala Ala Cys Lys Thr Val Thr Leu Thr Val Asp
                20                  25                  30

Gly Thr Ala Met Arg Val Thr Thr Met Lys Ser Arg Val Ile Asp Ile
```

```
                35                  40                  45
Val Glu Glu Asn Gly Phe Ser Val Asp Asp Arg Asp Leu Tyr Pro
 50                  55                  60

Ala Ala Gly Val Gln Val His Asp Ala Asp Thr Ile Val Leu Arg Arg
 65                  70                  75                  80

Ser Arg Pro Leu Gln Ile Ser Leu Asp Gly His Asp Ala Lys Gln Val
                 85                  90                  95

Trp Thr Thr Ala Ser Thr Val Asp Glu Ala Leu Ala Gln Leu Ala Met
                100                 105                 110

Thr Asp Thr Ala Pro Ala Ala Ser Arg Ala Ser Arg Val Pro Leu
            115                 120                 125

Ser Gly Met Ala Leu Pro Val Val Ser Ala Lys Thr Val Gln Leu Asn
            130                 135                 140

Asp Gly Gly Leu Val Arg Thr Val His Leu Pro Ala Pro Asn Val Ala
145                 150                 155                 160

Gly Leu Leu Ser Ala Ala Gly Val Pro Leu Leu Gln Ser Asp His Val
                165                 170                 175

Val Pro Ala Ala Thr Ala Pro Ile Val Glu Gly Met Gln Ile Gln Val
            180                 185                 190

Thr Arg Asn Arg Ile Lys Lys Val Thr Glu Arg Leu Pro Leu Pro Pro
            195                 200                 205

Asn Ala Arg Arg Val Glu Asp Pro Glu Met Asn Met Ser Arg Glu Val
210                 215                 220

Val Glu Asp Pro Gly Val Pro Gly Thr Gln Asp Val Thr Phe Ala Val
225                 230                 235                 240

Ala Glu Val Asn Gly Val Glu Thr Gly Arg Leu Pro Val Ala Asn Val
                245                 250                 255

Val Val Thr Pro Ala His Glu Ala Val Val Arg Val Gly Thr Lys Pro
            260                 265                 270

Gly Thr Glu Val Pro Pro Val Ile Asp Gly Ser Ile Trp Asp Ala Ile
            275                 280                 285

Ala Gly Cys Glu Ala Gly Gly Asn Trp Ala Ile Asn Thr Gly Asn Gly
            290                 295                 300

Tyr Tyr Gly Gly Val Gln Phe Asp Gln Gly Thr Trp Glu Ala Asn Gly
305                 310                 315                 320

Gly Leu Arg Tyr Ala Pro Arg Ala Asp Leu Ala Thr Arg Glu Glu Gln
                325                 330                 335

Ile Ala Val Ala Glu Val Thr Arg Leu Arg Gln Gly Trp Gly Ala Trp
            340                 345                 350

Pro Val Cys Ala Ala Arg Ala Gly Ala Arg
            355                 360
```

<210> SEQ ID NO 8
<211> LENGTH: 1089
<212> TYPE: DNA
<213> ORGANISM: Mycobacterium tuberculosis

<400> SEQUENCE: 8

```
atgttgcgcc tggtagtcgg tgcgctgctg ctggtgttgg cgttcgccgg tggctatgcg    60
gtcgccgcat gcaaaacggt gacgttgacc gtcgacggaa ccgcgatgcg ggtgaccacg   120
atgaaatcgc gggtgatcga catcgtcgaa gagaacgggt tctcagtcga cgaccgcgac   180
gacctgtatc ccgcggccgg cgtgcaggtc catgacgccg acaccatcgt gctgcggcgt   240
agccgtccgc tgcagatctc gctggatggt cacgacgcta agcaggtgtg gacgaccgcg   300
```

```
tcgacggtgg acgaggcgct ggcccaactc gcgatgaccg acacggcgcc ggccgcggct      360
tctcgcgcca gccgcgtccc gctgtccggg atggcgctac cggtcgtcag cgccaagacg      420
gtgcagctca acgacggcgg gttggtgcgc acggtgcact tgccggcccc caatgtcgcg      480
gggctgctga gtcggccgg cgtgccgctg ttgcaaagcg accacgtggt gcccgccgcg       540
acggccccga tcgtcgaagg catgcagatc caggtgaccc gcaatcggat caagaaggtc      600
accgagcggc tgccgctgcc gccgaacgcg cgtcgtgtcg aggacccgga gatgaacatg      660
agccgggagg tcgtcgaaga cccgggggtt ccggggaccc aggatgtgac gttcgcggta      720
gctgaggtca acgcgtcga gaccggccgt ttgcccgtcg ccaacgtcgt ggtgaccccg       780
gcccacgaag ccgtggtgcg ggtgggcacc aagcccggta ccgaggtgcc cccggtgatc      840
gacggaagca tctgggacgc gatcgccggc tgtgaggccg gtggcaactg gcgatcaac       900 accggcaacg ggtattacgg tggtgtgcag tttgaccagg gcacctggga ggccaacggc      960
gggctgcggt atgcaccccg cgctgacctc gccaccccgcg aagagcagat cgccgttgcc    1020
gaggtgaccc gactgcgtca aggttgggg gcctggccgg tatgtgctgc acgagcgggt     1080
gcgcgctga                                                            1089
```

<210> SEQ ID NO 9
<211> LENGTH: 176
<212> TYPE: PRT
<213> ORGANISM: Mycobacterium tuberculosis

<400> SEQUENCE: 9

```
Met His Pro Leu Pro Ala Asp His Gly Arg Ser Arg Cys Asn Arg His
1               5                   10                  15

Pro Ile Ser Pro Leu Ser Leu Ile Gly Asn Ala Ser Ala Thr Ser Gly
            20                  25                  30

Asp Met Ser Ser Met Thr Arg Ile Ala Lys Pro Leu Ile Lys Ser Ala
        35                  40                  45

Met Ala Ala Gly Leu Val Thr Ala Ser Met Ser Leu Ser Thr Ala Val
    50                  55                  60

Ala His Ala Gly Pro Ser Pro Asn Trp Asp Ala Val Ala Gln Cys Glu
65                  70                  75                  80

Ser Gly Gly Asn Trp Ala Ala Asn Thr Gly Asn Gly Lys Tyr Gly Gly
                85                  90                  95

Leu Gln Phe Lys Pro Ala Thr Trp Ala Ala Phe Gly Gly Val Gly Asn
            100                 105                 110

Pro Ala Ala Ala Ser Arg Glu Gln Gln Ile Ala Val Ala Asn Arg Val
        115                 120                 125

Leu Ala Glu Gln Gly Leu Asp Ala Trp Pro Thr Cys Gly Ala Ala Ser
    130                 135                 140

Gly Leu Pro Ile Ala Leu Trp Ser Lys Pro Ala Gln Gly Ile Lys Gln
145                 150                 155                 160

Ile Ile Asn Glu Ile Ile Trp Ala Gly Ile Gln Ala Ser Ile Pro Arg
                165                 170                 175
```

<210> SEQ ID NO 10
<211> LENGTH: 531
<212> TYPE: DNA
<213> ORGANISM: Mycobacterium tuberculosis

<400> SEQUENCE: 10

```
gtgcatcctt tgccggccga ccacggccgg tcgcggtgca atagacaccc gatctcacca       60
ctctctctaa tcggtaacgc ttcggccact tccggcgata tgtcgagcat gacaagaatc      120
```

```
gccaagccgc tcatcaagtc cgccatggcc gcaggactcg tcacggcatc catgtcgctc    180
tccaccgccg ttgcccacgc cggtcccagc ccgaactggg acgccgtcgc gcagtgcgaa    240
tccgggggca actgggcggc caacaccgga acggcaaat acggcggact gcagttcaag     300
ccggccacct gggccgcatt cggcggtgtc ggcaacccag cagctgcctc tcgggaacaa    360
caaatcgcag ttgccaatcg ggttctcgcc gaacagggat tggacgcgtg gccgacgtgc    420
ggcgccgcct ctggccttcc gatcgcactg tggtcgaaac ccgcgcaggg catcaagcaa    480
atcatcaacg agatcatttg gcaggcatt caggcaagta ttccgcgctg a              531
```

<210> SEQ ID NO 11
<211> LENGTH: 154
<212> TYPE: PRT
<213> ORGANISM: Mycobacterium tuberculosis

<400> SEQUENCE: 11

```
Met Thr Pro Gly Leu Leu Thr Thr Ala Gly Ala Gly Arg Pro Arg Asp
1               5                   10                  15

Arg Cys Ala Arg Ile Val Cys Thr Val Phe Ile Glu Thr Ala Val Val
                20                  25                  30

Ala Thr Met Phe Val Ala Leu Leu Gly Leu Ser Thr Ile Ser Ser Lys
            35                  40                  45

Ala Asp Asp Ile Asp Trp Asp Ala Ile Ala Gln Cys Glu Ser Gly Gly
        50                  55                  60

Asn Trp Ala Ala Asn Thr Gly Asn Gly Leu Tyr Gly Gly Leu Gln Ile
65                  70                  75                  80

Ser Gln Ala Thr Trp Asp Ser Asn Gly Gly Val Gly Ser Pro Ala Ala
                85                  90                  95

Ala Ser Pro Gln Gln Gln Ile Glu Val Ala Asp Asn Ile Met Lys Thr
            100                 105                 110

Gln Gly Pro Gly Ala Trp Pro Lys Cys Ser Ser Cys Ser Gln Gly Asp
        115                 120                 125

Ala Pro Leu Gly Ser Leu Thr His Ile Leu Thr Phe Leu Ala Ala Glu
    130                 135                 140

Thr Gly Gly Cys Ser Gly Ser Arg Asp Asp
145                 150
```

<210> SEQ ID NO 12
<211> LENGTH: 465
<212> TYPE: DNA
<213> ORGANISM: Mycobacterium tuberculosis

<400> SEQUENCE: 12

```
atgacaccgg gtttgcttac tactgcgggt gctggccgac cacgtgacag gtgcgccagg     60
atcgtatgca cggtgttcat cgaaaccgcc gttgtcgcga ccatgtttgt cgcgttgttg    120
ggtctgtcca ccatcagctc gaaagccgac gacatcgatt gggacgccat cgcgcaatgc    180
gaatccggcg gcaattgggc ggccaacacc ggtaacgggt tatacggtgg tctgcagatc    240
agccaggcga cgtgggattc caacggtggt gtcgggtcgc cggcggccgc gagtccccag    300
caacagatcg aggtcgcaga caacattatg aaaacccaag gcccgggtgc gtggccgaaa    360
tgtagttctt gtagtcaggg agacgcaccg ctgggctcgc tcacccacat cctgacgttc    420
ctcgcggccg agactggagg ttgttcgggg agcagggacg attga                    465
```

<210> SEQ ID NO 13
<211> LENGTH: 172

-continued

```
<212> TYPE: PRT
<213> ORGANISM: Mycobacterium tuberculosis

<400> SEQUENCE: 13

Met Lys Asn Ala Arg Thr Thr Leu Ile Ala Ala Ile Ala Gly Thr
1               5                   10                  15

Leu Val Thr Thr Ser Pro Ala Gly Ile Ala Asn Ala Asp Asp Ala Gly
                20                  25                  30

Leu Asp Pro Asn Ala Ala Ala Gly Pro Asp Ala Val Gly Phe Asp Pro
                35                  40                  45

Asn Leu Pro Pro Ala Pro Asp Ala Ala Pro Val Asp Thr Pro Pro Ala
    50                  55                  60

Pro Glu Asp Ala Gly Phe Asp Pro Asn Leu Pro Pro Leu Ala Pro
65                  70                  75                  80

Asp Phe Leu Ser Pro Pro Ala Glu Glu Ala Pro Pro Val Pro Val Ala
                85                  90                  95

Tyr Ser Val Asn Trp Asp Ala Ile Ala Gln Cys Glu Ser Gly Gly Asn
                100                 105                 110

Trp Ser Ile Asn Thr Gly Asn Gly Tyr Tyr Gly Gly Leu Arg Phe Thr
                115                 120                 125

Ala Gly Thr Trp Arg Ala Asn Gly Gly Ser Gly Ser Ala Ala Asn Ala
        130                 135                 140

Ser Arg Glu Glu Gln Ile Arg Val Ala Glu Asn Val Leu Arg Ser Gln
145                 150                 155                 160

Gly Ile Arg Ala Trp Pro Val Cys Gly Arg Arg Gly
                165                 170

<210> SEQ ID NO 14
<211> LENGTH: 519
<212> TYPE: DNA
<213> ORGANISM: Mycobacterium tuberculosis

<400> SEQUENCE: 14
ttgaagaacg cccgtacgac gctcatcgcc gccgcgattg ccgggacgtt ggtgaccacg    60
tcaccagccg gtatcgccaa tgccgacgac gcgggcttgg acccaaacgc cgcagccggc   120
ccggatgccg tgggctttga cccgaacctg ccgccggccc cggacgctgc acccgtcgat   180
actccgccgg ctccggagga cgcgggcttt gatcccaacc tccccccgcc gctggccccg   240
gacttcctgt ccccgcctgc ggaggaagcg cctcccgtgc ccgtggccta cagcgtgaac   300
tgggacgcga tcgcgcagtg cgagtccggt ggaaactggt cgatcaacac cggtaacggt   360
tactacggcg gcctgcggtt caccgccggc acctggcgtg ccaacggtgg ctcggggtcc   420
gcggccaacg cgagccggga ggagcagatc cgggtggctg agaacgtgct gcgttcgcag   480
ggtatccgcg cctggccggt ctgcggccgc cgcggctga                          519

<210> SEQ ID NO 15
<211> LENGTH: 297
<212> TYPE: PRT
<213> ORGANISM: Mycobacterium tuberculosis

<400> SEQUENCE: 15

Met Ser Ser Gly Asn Ser Ser Leu Gly Ile Ile Val Gly Ile Asp Asp
1               5                   10                  15

Ser Pro Ala Ala Gln Val Ala Val Arg Trp Ala Ala Arg Asp Ala Glu
                20                  25                  30

Leu Arg Lys Ile Pro Leu Thr Leu Val His Ala Val Ser Pro Glu Val
                35                  40                  45
```

```
Ala Thr Trp Leu Glu Val Pro Leu Pro Pro Gly Val Leu Arg Trp Gln
     50                  55                  60

Gln Asp His Gly Arg His Leu Ile Asp Asp Ala Leu Lys Val Val Glu
 65                  70                  75                  80

Gln Ala Ser Leu Arg Ala Gly Pro Pro Thr Val His Ser Glu Ile Val
                 85                  90                  95

Pro Ala Ala Ala Val Pro Thr Leu Val Asp Met Ser Lys Asp Ala Val
                100                 105                 110

Leu Met Val Val Gly Cys Leu Gly Ser Gly Arg Trp Pro Gly Arg Leu
            115                 120                 125

Leu Gly Ser Val Ser Ser Gly Leu Leu Arg His Ala His Cys Pro Val
        130                 135                 140

Val Ile Ile His Asp Glu Asp Ser Val Met Pro His Pro Gln Gln Ala
145                 150                 155                 160

Pro Val Leu Val Gly Val Asp Gly Ser Ser Ala Ser Glu Leu Ala Thr
                165                 170                 175

Ala Ile Ala Phe Asp Glu Ala Ser Arg Arg Asn Val Asp Leu Val Ala
                180                 185                 190

Leu His Ala Trp Ser Asp Val Asp Val Ser Glu Trp Pro Gly Ile Asp
            195                 200                 205

Trp Pro Ala Thr Gln Ser Met Ala Glu Gln Val Leu Ala Glu Arg Leu
210                 215                 220

Ala Gly Trp Gln Glu Arg Tyr Pro Asn Val Ala Ile Thr Arg Val Val
225                 230                 235                 240

Val Arg Asp Gln Pro Ala Arg Gln Leu Val Gln Ser Glu Glu Ala
                245                 250                 255

Gln Leu Val Val Val Gly Ser Arg Gly Arg Gly Tyr Ala Gly Met
            260                 265                 270

Leu Val Gly Ser Val Gly Glu Thr Val Ala Gln Leu Ala Arg Thr Pro
        275                 280                 285

Val Ile Val Ala Arg Glu Ser Leu Thr
290                 295

<210> SEQ ID NO 16
<211> LENGTH: 894
<212> TYPE: DNA
<213> ORGANISM: Mycobacterium tuberculosis

<400> SEQUENCE: 16
atgtcatcgg gcaattcatc tctgggaatt atcgtcggga tcgacgattc accggccgca      60
caggttgcgg tgcggtgggc agctcgggat gcggagttgc gaaaaatccc tctgacgctc     120
gtgcacgcgg tgtcgccgga agtagccacc tggctggagg tgccactgcc gccgggcgtg     180
ctgcgatggc agcaggatca cgggcgccac ctgatcgacg acgcactcaa ggtggttgaa     240
caggcttcgc tgcgcgctgg tccccccacg gtccacagtg aaatcgttcc ggcggcagcc     300
gttcccacat tggtcgacat gtccaaagac gcagtgctga tggtcgtggg ttgtctcgga     360
agtgggcggt ggccgggccg gctgctcggt tcggtcagtt ccggcctgct ccgccacgcg     420
cactgtccgg tcgtgatcat ccacgacgaa gattcggtga tgccgcatcc ccagcaagcg     480
ccggtgctag ttggcgttga cggctcgtcg gcctccgagc tggcgaccgc aatcgcattc     540
gacgaagcgt cgcggcgaaa cgtggacctg gtggcgctgc acgcatggag cgacgtcgat     600
gtgtcggagt ggcccggaat cgattggccg gcaactcagt cgatggccga gcaggtgctg     660
gccgagcggt tggcgggttg gcaggagcgg tatcccaacg tagccataac ccgcgtggtg     720
```

```
gtgcgcgatc agccggcccg ccagctcgtc caacgctccg aggaagccca gctggtcgtg    780
gtcggcagcc ggggccgcgg cggctacgcc ggaatgctgg tggggtcggt aggcgaaacc    840
gttgctcagc tggcgcggac gccggtcatc gtggcacgcg agtcgctgac ttag          894
```

<210> SEQ ID NO 17
<211> LENGTH: 96
<212> TYPE: PRT
<213> ORGANISM: Mycobacterium tuberculosis

<400> SEQUENCE: 17

```
Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95
```

<210> SEQ ID NO 18
<211> LENGTH: 291
<212> TYPE: DNA
<213> ORGANISM: Mycobacterium tuberculosis

<400> SEQUENCE: 18

```
atgtcgcaaa tcatgtacaa ctaccccgcg atgttgggtc acgccgggga tatggccgga    60
tatgccggca cgctgcagag cttgggtgcc gagatcgccg tggagcaggc cgcgttgcag    120
agtgcgtggc agggcgatac cgggatcacg tatcaggcgt ggcaggcaca gtggaaccag    180
gccatggaag atttggtgcg ggcctatcat gcgatgtcca gcacccatga agccaacacc    240
atggcgatga tggcccgcga cacggccgaa gccgccaaat ggggcggcta g             291
```

<210> SEQ ID NO 19
<211> LENGTH: 143
<212> TYPE: PRT
<213> ORGANISM: Mycobacterium tuberculosis

<400> SEQUENCE: 19

```
Met Thr Thr Ala Arg Asp Ile Met Asn Ala Gly Val Thr Cys Val Gly
1               5                   10                  15

Glu His Glu Thr Leu Thr Ala Ala Ala Gln Tyr Met Arg Glu His Asp
            20                  25                  30

Ile Gly Ala Leu Pro Ile Cys Gly Asp Asp Asp Arg Leu His Gly Met
        35                  40                  45

Leu Thr Asp Arg Asp Ile Val Ile Lys Gly Leu Ala Ala Gly Leu Asp
    50                  55                  60

Pro Asn Thr Ala Thr Ala Gly Glu Leu Ala Arg Asp Ser Ile Tyr Tyr
65                  70                  75                  80

Val Asp Ala Asn Ala Ser Ile Gln Glu Met Leu Asn Val Met Glu Glu
                85                  90                  95

His Gln Val Arg Arg Val Pro Val Ile Ser Glu His Arg Leu Val Gly
                100                 105                 110
```

```
Ile Val Thr Glu Ala Asp Ile Ala Arg His Leu Pro Glu His Ala Ile
    115                 120                 125

Val Gln Phe Val Lys Ala Ile Cys Ser Pro Met Ala Leu Ala Ser
130                 135                 140

<210> SEQ ID NO 20
<211> LENGTH: 432
<212> TYPE: DNA
<213> ORGANISM: Mycobacterium tuberculosis

<400> SEQUENCE: 20
atgaccaccg cacgcgacat catgaacgca ggtgtgacct gtgttggcga acacgagacg     60
ctaaccgctg ccgctcaata catgcgtgag cacgacatcg gcgcgttgcc gatctgcggg    120
gacgacgacc ggctgcacgg catgctcacc gaccgcgaca ttgtgatcaa aggcctggct    180
gcgggcctag acccgaatac cgccacggct ggcgagttgg cccgggacag catctactac    240
gtcgatgcga acgcaagcat ccaggagatg ctcaacgtca tggaagaaca tcaggtccgc    300
cgtgttccgg tcatctcaga gcaccgcttg gtcggaatcg tcaccgaagc cgacatcgcc    360
cgacacctgc ccgagcacgc cattgtgcag ttcgtcaagg caatctgctc gcccatggcc    420
ctcgccagct ag                                                        432

<210> SEQ ID NO 21
<211> LENGTH: 295
<212> TYPE: PRT
<213> ORGANISM: Mycobacterium tuberculosis

<400> SEQUENCE: 21

Met Ser Lys Pro Arg Lys Gln His Gly Val Val Gly Val Asp Gly
1               5                   10                  15

Ser Leu Glu Ser Asp Ala Ala Ala Cys Trp Gly Ala Thr Asp Ala Ala
                20                  25                  30

Met Arg Asn Ile Pro Leu Thr Val Val His Val Asn Ala Asp Val
            35                  40                  45

Ala Thr Trp Pro Pro Met Pro Tyr Pro Glu Thr Trp Gly Val Trp Gln
        50                  55                  60

Glu Asp Glu Gly Arg Gln Ile Val Ala Asn Ala Val Lys Leu Ala Lys
65                  70                  75                  80

Glu Ala Val Gly Ala Asp Arg Lys Leu Ser Val Lys Ser Glu Leu Val
                85                  90                  95

Phe Ser Thr Pro Val Pro Thr Met Val Glu Ile Ser Asn Glu Ala Glu
            100                 105                 110

Met Val Val Leu Gly Ser Ser Gly Arg Gly Ala Leu Ala Arg Gly Leu
        115                 120                 125

Leu Gly Ser Val Ser Ser Ser Leu Val Arg Arg Ala Gly Cys Pro Val
    130                 135                 140

Ala Val Ile His Ser Asp Asp Val Ile Pro Asp Pro Gln His Ala
145                 150                 155                 160

Pro Val Leu Val Gly Ile Asp Gly Ser Pro Val Ser Glu Leu Ala Thr
                165                 170                 175

Ala Val Ala Phe Asp Glu Ala Ser Arg Arg Gly Val Glu Leu Ile Ala
            180                 185                 190

Val His Ala Trp Ser Asp Val Glu Val Glu Leu Pro Gly Leu Asp
        195                 200                 205

Phe Ser Ala Val Gln Gln Glu Ala Glu Leu Ser Leu Ala Glu Arg Leu
    210                 215                 220
```

-continued

```
Ala Gly Trp Gln Glu Arg Tyr Pro Asp Val Pro Val Ser Arg Val Val
225                 230                 235                 240

Val Cys Asp Arg Pro Ala Arg Lys Leu Val Gln Lys Ser Ala Ser Ala
            245                 250                 255

Gln Leu Val Val Val Gly Ser His Gly Arg Gly Gly Leu Thr Gly Met
            260                 265                 270

Leu Leu Gly Ser Val Ser Asn Ala Val Leu His Ala Ala Arg Val Pro
        275                 280                 285

Val Ile Val Ala Arg Gln Ser
    290                 295

<210> SEQ ID NO 22
<211> LENGTH: 888
<212> TYPE: DNA
<213> ORGANISM: Mycobacterium tuberculosis

<400> SEQUENCE: 22
atgtctaaac cccgcaagca gcacggagtt gtcgtcgggg tagatggttc gctcgaatcg      60
gatgccgccg cctgttgggg tgccaccgat gcggcgatga ggaacattcc gctgaccgtg     120
gtccacgtgg tgaacgccga tgtagcgacg tggccgccga tgccgtatcc ggagacctgg     180
ggggtttggc aggaggacga gggtcgccag atcgtcgcca acgccgtcaa gctcgccaaa     240
gaggcggttg gagcggatcg aaagctcagc gtaaagagcg agctcgtatt ttccacgccg     300
gtacctacca tggttgaaat ctccaacgag gcagagatgg tggtgttggg cagctcgggc     360
cggggagcgc tggcccgagg cttgctcggt tcggtcagct cgagcctggt gcgacgcgcc     420
gggtgcccgg tcgcggtcat ccacagcgat gatgcggtga tccctgatcc gcagcacgct     480
cccgtgctgg tgggaatcga cggttcgccg gtttcggagc ttgcgacggc ggtggcattt     540
gacgaggcgt cgcgccgcgg cgtcgaactg atcgccgtgc acgcgtggag tgacgtcgaa     600
gtggtggaac ttccgggttt ggacttctcg gctgtacagc aggaagcgga gcttagtctc     660
gccgaacgct tggcaggttg gcaagaacgc tatcccgatg tgccggtgag ccgggttgtc     720
gtttgcgatc gcccggcgcg gaagctggtg caaaagtcgg cgtccgccca gcttgtcgtc     780
gttggcagtc atggccgagg tggcttgacc ggcatgcttc tggggtcggt cagtaacgcg     840
gtcttacacg ccgcgcgggt gccagtgatc gtggcacggc agtcgtga                  888

<210> SEQ ID NO 23
<211> LENGTH: 317
<212> TYPE: PRT
<213> ORGANISM: Mycobacterium tuberculosis

<400> SEQUENCE: 23

Met Ser Ala Gln Gln Thr Asn Leu Gly Ile Val Val Gly Val Asp Gly
1               5                   10                  15

Ser Pro Cys Ser His Thr Ala Val Glu Trp Ala Ala Arg Asp Ala Gln
            20                  25                  30

Met Arg Asn Val Ala Leu Arg Val Val Gln Val Val Pro Pro Val Ile
        35                  40                  45

Thr Ala Pro Glu Gly Trp Ala Phe Glu Tyr Ser Arg Phe Gln Glu Ala
    50                  55                  60

Gln Lys Arg Glu Ile Val Glu His Ser Tyr Leu Val Ala Gln Ala His
65                  70                  75                  80

Gln Ile Val Glu Gln Ala His Lys Val Ala Leu Glu Ala Ser Ser Ser
                85                  90                  95

Gly Arg Ala Ala Gln Ile Thr Gly Glu Val Leu His Gly Gln Ile Val
```

```
                    100                 105                 110
Pro Thr Leu Ala Asn Ile Ser Arg Gln Val Ala Met Val Val Leu Gly
            115                 120                 125

Tyr Arg Gly Gln Gly Ala Val Ala Gly Ala Leu Leu Gly Ser Val Ser
        130                 135                 140

Ser Ser Leu Val Arg His Ala His Gly Pro Val Ala Val Ile Pro Glu
145                 150                 155                 160

Glu Pro Arg Pro Ala Arg Pro Pro His Ala Pro Val Val Val Gly Ile
                165                 170                 175

Asp Gly Ser Pro Thr Ser Gly Leu Ala Ala Glu Ile Ala Phe Asp Glu
            180                 185                 190

Ala Ser Arg Arg Gly Val Asp Leu Val Ala Leu His Ala Trp Ser Asp
        195                 200                 205

Met Gly Pro Leu Asp Phe Pro Arg Leu Asn Trp Ala Pro Ile Glu Trp
    210                 215                 220

Arg Asn Leu Glu Asp Glu Gln Glu Lys Met Leu Ala Arg Arg Leu Ser
225                 230                 235                 240

Gly Trp Gln Asp Arg Tyr Pro Asp Val Val His Lys Val Val
                245                 250                 255

Cys Asp Arg Pro Ala Pro Arg Leu Leu Glu Leu Ala Gln Thr Ala Gln
                260                 265                 270

Leu Val Val Val Gly Ser His Gly Arg Gly Phe Pro Gly Met His
            275                 280                 285

Leu Gly Ser Val Ser Arg Ala Val Val Asn Ser Gly Gln Ala Pro Val
        290                 295                 300

Ile Val Ala Arg Ile Pro Gln Asp Pro Ala Val Pro Ala
305                 310                 315

<210> SEQ ID NO 24
<211> LENGTH: 954
<212> TYPE: DNA
<213> ORGANISM: Mycobacterium tuberculosis

<400> SEQUENCE: 24
atgtcagccc aacaaacgaa cctcggaatc gtggtcggtg tggatggttc accctgctcg      60
catacggcag tcgaatgggc cgcgcgcgat gcgcagatgc gcaacgttgc gctccgcgtg     120
gtgcaggtcg tgcccccggt aataaccgcc ccggaagggt gggcatttga gtattcgcgg     180
tttcaagaag cccaaaagcg cgaaatcgtc gaacactcgt acctggtcgc caagcgcac      240 caaatcgtcg aacaggccca aggtcgcc ctcgaggcat cctcctcagg tcgcgccgcg       300
caaatcaccg cgaagtgct gcacggccag atagtgccca cgctggccaa catctccagg      360
caggtcgcga tggtcgtgct gggctaccga ggtcagggcg ccgtagccgg cgccttgctg     420
ggatcggtca gctcaagcct ggttcgccac gctcatggcc ctgtcgccgt aatacccgag     480
gagccgcgac cggcgcgccc gccgcacgcg ccggttgtgg tgggcatcga cggctcgccc     540
acctcgggat ggcggccga gatcgccttc gacgaggcat cgcgccgcgg cgtggacttg     600
gtggcgctgc acgcgtggag cgacatgggc cccctcgact ttcctaggct caattgggcg    660
ccgatcgaat ggagaaacct cgaagacgag caggagaaaa tgctcgcccg cgtctgagc     720 ggatggcaag accggtatcc cgatgtcgtc gtgcacaaag tcgtggtgtg cgatcgaccg    780 gcacccccgcc tgctcgaatt ggcacaaacc gctcagcttg tggtggttgg cagccacggc    840 cgcgggggggt tccccggcat gcatctcggc tcagtcagca gagcggtggt caattccggt    900
caggctccgg ttatcgtcgc ccgaatcccc caagatccgg cagtgccggc ctga           954
```

<210> SEQ ID NO 25
<211> LENGTH: 396
<212> TYPE: PRT
<213> ORGANISM: Mycobacterium tuberculosis

<400> SEQUENCE: 25

Met Ala Lys Ala Lys Phe Gln Arg Thr Lys Pro His Val Asn Ile Gly
1               5                   10                  15

Thr Ile Gly His Val Asp His Gly Lys Thr Thr Leu Thr Ala Ala Ile
            20                  25                  30

Thr Lys Val Leu His Asp Lys Phe Pro Asp Leu Asn Glu Thr Lys Ala
        35                  40                  45

Phe Asp Gln Ile Asp Asn Ala Pro Glu Glu Arg Gln Arg Gly Ile Thr
50                  55                  60

Ile Asn Ile Ala His Val Glu Tyr Gln Thr Asp Lys Arg His Tyr Ala
65                  70                  75                  80

His Val Asp Ala Pro Gly His Ala Asp Tyr Ile Lys Asn Met Ile Thr
                85                  90                  95

Gly Ala Ala Gln Met Asp Gly Ala Ile Leu Val Val Ala Ala Thr Asp
            100                 105                 110

Gly Pro Met Pro Gln Thr Arg Glu His Val Leu Leu Ala Arg Gln Val
        115                 120                 125

Gly Val Pro Tyr Ile Leu Val Ala Leu Asn Lys Ala Asp Ala Val Asp
130                 135                 140

Asp Glu Glu Leu Leu Glu Leu Val Glu Met Glu Val Arg Glu Leu Leu
145                 150                 155                 160

Ala Ala Gln Glu Phe Asp Glu Asp Ala Pro Val Val Arg Val Ser Ala
                165                 170                 175

Leu Lys Ala Leu Glu Gly Asp Ala Lys Trp Val Ala Ser Val Glu Glu
            180                 185                 190

Leu Met Asn Ala Val Asp Glu Ser Ile Pro Asp Pro Val Arg Glu Thr
        195                 200                 205

Asp Lys Pro Phe Leu Met Pro Val Glu Asp Val Phe Thr Ile Thr Gly
210                 215                 220

Arg Gly Thr Val Val Thr Gly Arg Val Glu Arg Gly Val Ile Asn Val
225                 230                 235                 240

Asn Glu Glu Val Glu Ile Val Gly Ile Arg Pro Ser Thr Thr Lys Thr
                245                 250                 255

Thr Val Thr Gly Val Glu Met Phe Arg Lys Leu Leu Asp Gln Gly Gln
            260                 265                 270

Ala Gly Asp Asn Val Gly Leu Leu Leu Arg Gly Val Lys Arg Glu Asp
        275                 280                 285

Val Glu Arg Gly Gln Val Val Thr Lys Pro Gly Thr Thr Thr Pro His
290                 295                 300

Thr Glu Phe Glu Gly Gln Val Tyr Ile Leu Ser Lys Asp Glu Gly Gly
305                 310                 315                 320

Arg His Thr Pro Phe Phe Asn Asn Tyr Arg Pro Gln Phe Tyr Phe Arg
                325                 330                 335

Thr Thr Asp Val Thr Gly Val Val Thr Leu Pro Glu Gly Thr Glu Met
            340                 345                 350

Val Met Pro Gly Asp Asn Thr Asn Ile Ser Val Lys Leu Ile Gln Pro
        355                 360                 365

Val Ala Met Asp Glu Gly Leu Arg Phe Ala Ile Arg Glu Gly Gly Arg
370                 375                 380

Thr Val Gly Ala Gly Arg Val Thr Lys Ile Ile Lys
385                 390                 395

<210> SEQ ID NO 26
<211> LENGTH: 1191
<212> TYPE: DNA
<213> ORGANISM: Mycobacterium tuberculosis

<400> SEQUENCE: 26

```
gtggcgaagg cgaagttcca gcggaccaag ccccacgtca acatcgggac catcggtcac        60
gttgaccacg gcaagaccac cctgaccgcg gctatcacca aggtcctgca cgacaaattc       120
cccgatctga acgagacgaa ggcattcgac cagatcgaca acgccccga ggagcgtcag        180
cgcggtatca ccatcaacat cgcgcacgtg gagtaccaga ccgacaagcg gcactacgca       240
cacgtcgacg ccctggcca cgccgactac atcaagaaca tgatcaccgg cgccgcgcag        300
atggacggtg cgatcctggt ggtcgccgcc accgacggcc cgatgcccca gacccgcgag       360
cacgttctgc tggcgcgtca gtgggtgtg ccctacatcc tggtagcgct gaacaaggcc        420
gacgcagtgg acgacgagga gctgctcgaa ctcgtcgaga tggaggtccg cgagctgctg       480
gctgcccagg aattcgacga ggacgccccg gttgtgcggg tctcggcgct caaggcgctc       540
gagggtgacg cgaagtgggt tgcctctgtc gaggaactga tgaacgcggt cgacgagtcg       600
attccggacc cggtccgcga gaccgacaag ccgttcctga tgccggtcga ggacgtcttc       660
accattaccg gccgcggaac cgtggtcacc ggacgtgtgg agcgcggcgt gatcaacgtg       720
aacgaggaag ttgagatcgt cggcattcgc ccatcgacca ccaagaccac cgtcaccggt       780
gtggagatgt tccgcaagct gctcgaccag ggccaggcgg gcgacaacgt tggtttgctg       840
ctgcggggcg tcaagcgcga ggacgtcgag cgtggccagg ttgtcaccaa gcccggcacc       900
accacgccgc acaccgagtt cgaaggccag gtctacatcc tgtccaagga cgagggcggc       960
cggcacacgc cgttcttcaa caactaccgt ccgcagttct acttccgcac caccgacgtg      1020
accggtgtgg tgacactgcc ggagggcacc gagatggtga tgcccggtga caacaccaac      1080
atctcggtga agttgatcca gcccgtcgcc atggacgaag gtctgcgttt cgcgatccgc      1140
gagggtggcc gcaccgtggg cgccggccgg gtcaccaaga tcatcaagta g               1191
```

<210> SEQ ID NO 27
<211> LENGTH: 338
<212> TYPE: PRT
<213> ORGANISM: Mycobacterium tuberculosis

<400> SEQUENCE: 27

Met Ser Ala Lys Leu Thr Asp Leu Gln Leu Leu His Glu Leu Glu Pro
1               5                   10                  15

Val Val Glu Lys Tyr Leu Asn Arg His Leu Ser Met His Lys Pro Trp
            20                  25                  30

Asn Pro His Asp Tyr Ile Pro Trp Ser Asp Gly Lys Asn Tyr Tyr Ala
        35                  40                  45

Leu Gly Gly Gln Asp Trp Asp Pro Asp Gln Ser Lys Leu Ser Asp Val
    50                  55                  60

Ala Gln Val Ala Met Val Gln Asn Leu Val Thr Glu Asp Asn Leu Pro
65                  70                  75                  80

Ser Tyr His Arg Glu Ile Ala Met Asn Met Gly Met Asp Gly Ala Trp
                85                  90                  95

Gly Gln Trp Val Asn Arg Trp Thr Ala Glu Glu Asn Arg His Gly Ile
            100                 105                 110

```
Ala Leu Arg Asp Tyr Leu Val Val Thr Arg Ser Val Asp Pro Val Glu
        115                 120                 125

Leu Glu Lys Leu Arg Leu Glu Val Val Asn Arg Gly Phe Ser Pro Gly
    130                 135                 140

Gln Asn His Gln Gly His Tyr Phe Ala Glu Ser Leu Thr Asp Ser Val
145                 150                 155                 160

Leu Tyr Val Ser Phe Gln Glu Leu Ala Thr Arg Ile Ser His Arg Asn
                165                 170                 175

Thr Gly Lys Ala Cys Asn Asp Pro Val Ala Asp Gln Leu Met Ala Lys
            180                 185                 190

Ile Ser Ala Asp Glu Asn Leu His Met Ile Phe Tyr Arg Asp Val Ser
        195                 200                 205

Glu Ala Ala Phe Asp Leu Val Pro Asn Gln Ala Met Lys Ser Leu His
    210                 215                 220

Leu Ile Leu Ser His Phe Gln Met Pro Gly Phe Gln Val Pro Glu Phe
225                 230                 235                 240

Arg Arg Lys Ala Val Ile Ala Val Gly Gly Val Tyr Asp Pro Arg
                245                 250                 255

Ile His Leu Asp Glu Val Val Met Pro Val Leu Lys Lys Trp Arg Ile
            260                 265                 270

Phe Glu Arg Glu Asp Phe Thr Gly Glu Gly Ala Lys Leu Arg Asp Glu
        275                 280                 285

Leu Ala Leu Val Ile Lys Asp Leu Glu Leu Ala Cys Asp Lys Phe Glu
    290                 295                 300

Val Ser Lys Gln Arg Gln Leu Asp Arg Glu Ala Arg Thr Gly Lys Lys
305                 310                 315                 320

Val Ser Ala His Glu Leu His Lys Thr Ala Gly Lys Leu Ala Met Ser
                325                 330                 335

Arg Arg

<210> SEQ ID NO 28
<211> LENGTH: 1017
<212> TYPE: DNA
<213> ORGANISM: Mycobacterium tuberculosis

<400> SEQUENCE: 28
atgtcagcca agctgaccga cctgcagctg ctgcacgaac ttgaaccggt cgtcgagaag      60
tacctgaacc ggcacctgag catgcacaag ccctggaacc cgcacgacta catcccgtgg     120
tcggacggga agaactacta cgcgctcggc gggcaggatt gggaccccga ccagagcaag     180
ctttctgatg tcgcccaggt ggcgatggtg cagaacctgg tcaccgagga caacctgccg     240
tcgtatcacc gcgagatcgc gatgaacatg ggcatggacg gcgcgtgggg gcagtgggtc     300
aaccgttgga ccgccgagga gaatcggcac ggcatcgcgc tgcgcgacta cctggtggtg     360
acccgatcgg tcgaccctgt cgagttggag aaacttcgcc tcgaggtagt caaccggggc     420
ttcagcccag gccaaaacca ccagggccac tatttcgcgg agagcctcac cgactccgtc     480
ctctatgtca gtttccagga actggcaacc cggatttcgc accgcaatac cggcaaggca     540
tgtaacgacc ccgtcgccga ccagctcatg gccaagatct cggcagacga gaatctgcac     600
atgatcttct accgcgacgt cagcgaggcc gcgttcgacc tcgtgcccaa ccaggccatg     660
aagtcgctgc acctgatttt gagccacttc cagatgcccg gcttccaagt acccgagttc     720
cggcgcaaag ccgtggtcat cgccgtcggg ggtgtctacg acccgcgcat ccacctcgac     780
gaagtcgtca tgccggtact gaagaaatgg cgtatcttcg agcgcgagga cttcaccggc     840
```

```
gaggggggcta agctgcgcga cgagctggcc ctggtgatca aggacctcga gctggcctgc    900
gacaagttcg aggtgtccaa gcaacgccaa ctcgaccggg aagcccgtac gggcaagaag    960
gtcagcgcac acgagctgca taaaaccgct ggcaaactgg cgatgagccg tcgttag       1017
```

<210> SEQ ID NO 29
<211> LENGTH: 339
<212> TYPE: PRT
<213> ORGANISM: Mycobacterium tuberculosis

<400> SEQUENCE: 29

```
Met Thr Glu Pro Ala Ala Trp Asp Glu Gly Lys Pro Arg Ile Ile Thr
1               5                   10                  15

Leu Thr Met Asn Pro Ala Leu Asp Ile Thr Thr Ser Val Asp Val Val
            20                  25                  30

Arg Pro Thr Glu Lys Met Arg Cys Gly Ala Pro Arg Tyr Asp Pro Gly
        35                  40                  45

Gly Gly Gly Ile Asn Val Ala Arg Ile Val His Val Leu Gly Gly Cys
    50                  55                  60

Ser Thr Ala Leu Phe Pro Ala Gly Gly Ser Thr Gly Ser Leu Leu Met
65                  70                  75                  80

Ala Leu Leu Gly Asp Ala Gly Val Pro Phe Arg Val Ile Pro Ile Ala
                85                  90                  95

Ala Ser Thr Arg Glu Ser Phe Thr Val Asn Glu Ser Arg Thr Ala Lys
            100                 105                 110

Gln Tyr Arg Phe Val Leu Pro Gly Pro Ser Leu Thr Val Ala Glu Gln
        115                 120                 125

Glu Gln Cys Leu Asp Glu Leu Arg Gly Ala Ala Ser Ala Ala Phe
    130                 135                 140

Val Val Ala Ser Gly Ser Leu Pro Pro Gly Val Ala Ala Asp Tyr Tyr
145                 150                 155                 160

Gln Arg Val Ala Asp Ile Cys Arg Arg Ser Ser Thr Pro Leu Ile Leu
                165                 170                 175

Asp Thr Ser Gly Gly Gly Leu Gln His Ile Ser Ser Gly Val Phe Leu
            180                 185                 190

Leu Lys Ala Ser Val Arg Glu Leu Arg Glu Cys Val Gly Ser Glu Leu
        195                 200                 205

Leu Thr Glu Pro Glu Gln Leu Ala Ala His Glu Leu Ile Asp Arg
    210                 215                 220

Gly Arg Ala Glu Val Val Val Ser Leu Gly Ser Gln Gly Ala Leu
225                 230                 235                 240

Leu Ala Thr Arg His Ala Ser His Arg Phe Ser Ser Ile Pro Met Thr
                245                 250                 255

Ala Val Ser Gly Val Gly Ala Gly Asp Ala Met Val Ala Ala Ile Thr
            260                 265                 270

Val Gly Leu Ser Arg Gly Trp Ser Leu Ile Lys Ser Val Arg Leu Gly
        275                 280                 285

Asn Ala Ala Gly Ala Ala Met Leu Leu Thr Pro Gly Thr Ala Ala Cys
    290                 295                 300

Asn Arg Asp Asp Val Glu Arg Phe Phe Glu Leu Ala Ala Glu Pro Thr
305                 310                 315                 320

Glu Val Gly Gln Asp Gln Tyr Val Trp His Pro Ile Val Asn Pro Glu
                325                 330                 335

Ala Ser Pro
```

<210> SEQ ID NO 30
<211> LENGTH: 1019
<212> TYPE: DNA
<213> ORGANISM: Mycobacterium tuberculosis

<400> SEQUENCE: 30

```
atgacggagc cagcggcgtg ggacgaaggc aagccgcgaa tcatcacttt gaccatgaac      60
cccgccttgg acatcacgac gagcgtcgac gtggtgcgcc cgaccgagaa aatgcgttgt     120
ggcgcacctc gctacgatcc cggcggcggc ggtatcaatg tcgcccgcat tgtgcatgtc     180
ctcggcggtt gctcgacagc actgttcccg gccggcgggt cgaccgggag cctgctgatg     240
gcgctgctcg gtgatgcggg agtgccattt cgcgtcattc cgatcgcggc ctcgacgcgg     300
gagagcttca cggtcaacga gtccaggacc gccaagcagt atcgtttcgt gcttccgggc     360
cgtcgctgac cgtcgcggag caggagcaat gcctcgacga actgcgcggt cggcggcttt     420
cggccgccct tgtggtggcc agtggcagcc tgccgccagg tgtggctgcc gactactatc     480
agcgggttgc cgacatctgc cgccgatcga gcactccgct gatcctggat acatctggtg     540
gcgggttgca gcacatttcg tccggggtgt ttcttctcaa ggcgagcgtg cgggaactgc     600
gcgagtgcgt cggatccgaa ctgctgaccg agcccgaaca actggccgcc gcacacgaac     660
tcattgaccg tgggcgcgcc gaggtcgtgg tggtctcgct tggatctcag ggcgcgctat     720
tggccacacg acatgcgagc catcgatttt cgtcgattcc gatgaccgcg gttagcggtg     780
tcggcgccgg cgacgcgatg gtggccgcga ttaccgtggg cctcagccgt ggctggtcgc     840
tcatcaagtc cgttcgcttg ggaaacgcgg caggtgcagc catgctgctg acgccaggca     900
ccgcggcctg caatcgcgac gatgtggaga ggttcttcga gctggcggcc gaacccaccg     960
aagtcgggca ggatcaatac gtttggcacc cgatcgttaa cccggaagcc tcgccatga    1019
```

<210> SEQ ID NO 31
<211> LENGTH: 413
<212> TYPE: PRT
<213> ORGANISM: Mycobacterium tuberculosis

<400> SEQUENCE: 31

Met Ala Ser Ser Ala Ser Asp Gly Thr His Glu Arg Ser Ala Phe Arg
1               5                   10                  15

Leu Ser Pro Pro Val Leu Ser Gly Ala Met Gly Pro Phe Met His Thr
            20                  25                  30

Gly Leu Tyr Val Ala Gln Ser Trp Arg Asp Tyr Leu Gly Gln Gln Pro
        35                  40                  45

Asp Lys Leu Pro Ile Ala Arg Pro Thr Ile Ala Leu Ala Ala Gln Ala
    50                  55                  60

Phe Arg Asp Glu Ile Val Leu Leu Gly Leu Lys Ala Arg Arg Pro Val
65                  70                  75                  80

Ser Asn His Arg Val Phe Glu Arg Ile Ser Gln Glu Val Ala Ala Gly
                85                  90                  95

Leu Glu Phe Tyr Gly Asn Arg Arg Trp Leu Glu Lys Pro Ser Gly Phe
            100                 105                 110

Phe Ala Gln Pro Pro Leu Thr Glu Val Ala Val Arg Lys Val Lys
            115                 120                 125

Asp Arg Arg Ser Phe Tyr Arg Ile Phe Asp Ser Gly Phe Thr
    130                 135                 140

Pro His Pro Gly Glu Pro Gly Ser Gln Arg Trp Leu Ser Tyr Thr Ala
145                 150                 155                 160

```
            Asn Asn Arg Glu Tyr Ala Leu Leu Arg His Pro Glu Pro Arg Pro
                            165                 170                 175

Trp Leu Val Cys Val His Gly Thr Glu Met Gly Arg Ala Pro Leu Asp
                        180                 185                 190

Leu Ala Val Phe Arg Ala Trp Lys Leu His Asp Glu Leu Gly Leu Asn
                        195                 200                 205

Ile Val Met Pro Val Leu Pro Met His Gly Pro Arg Gly Gln Gly Leu
                    210                 215                 220

Pro Lys Gly Ala Val Phe Pro Gly Glu Asp Val Leu Asp Asp Val His
            225                 230                 235                 240

Gly Thr Ala Gln Ala Val Trp Asp Ile Arg Arg Leu Leu Ser Trp Ile
                        245                 250                 255

Arg Ser Gln Glu Glu Glu Ser Leu Ile Gly Leu Asn Gly Leu Ser Leu
                        260                 265                 270

Gly Gly Tyr Ile Ala Ser Leu Val Ala Ser Leu Glu Glu Gly Leu Ala
                        275                 280                 285

Cys Ala Ile Leu Gly Val Pro Val Ala Asp Leu Ile Glu Leu Leu Gly
                        290                 295                 300

Arg His Cys Gly Leu Arg His Lys Asp Pro Arg His Thr Val Lys
            305                 310                 315                 320

Met Ala Glu Pro Ile Gly Arg Met Ile Ser Pro Leu Ser Leu Thr Pro
                            325                 330                 335

Leu Val Pro Met Pro Gly Arg Phe Ile Tyr Ala Gly Ile Ala Asp Arg
                        340                 345                 350

Leu Val His Pro Arg Glu Gln Val Thr Arg Leu Trp Glu His Trp Gly
                        355                 360                 365

Lys Pro Glu Ile Val Trp Tyr Pro Gly Gly His Thr Gly Phe Phe Gln
            370                 375                 380

Ser Arg Pro Val Arg Arg Phe Val Gln Ala Ala Leu Glu Gln Ser Gly
            385                 390                 395                 400

Leu Leu Asp Ala Pro Arg Thr Gln Arg Asp Arg Ser Ala
                        405                 410

<210> SEQ ID NO 32
<211> LENGTH: 1242
<212> TYPE: DNA
<213> ORGANISM: Mycobacterium tuberculosis

<400> SEQUENCE: 32
atggcaagtt ctgcgagcga cggcacccac gaacgctcgg cttttcgcct gagtccaccg      60
gtcttgagcg gcgccatggg accgttcatg cacaccggtc tgtacgtcgc tcaatcgtgg     120
cgcgactatc tgggtcaaca gcccgataaa ctgccgatcg cacggcccac tattgcctta     180
gcggcgcaag cctttcgaga cgaaatcgtc ctgctgggcc tcaaggcacg acgtccggtc     240
agcaatcatc gagtgttcga gcgcatcagc caagaagtgg ccgctggact ggagttctat     300
gggaatcgca gatggctgga gaagcctagc ggatttttg cccagccccc accgctcacc      360
gaggtcgcgg tccgaaaggt caaggaccgc agacgctcct tttatcgcat cttcttcgac     420
agtgggttta cgccgcatcc gggtgaaccg ggcagccaac ggtggctctc atacactgcg     480
aacaatcgcg agtacgccct gttactgcgg cacccagagc cgcgtccctg ctggtttgt     540 gtacacggca ccgagatggg cagggccccg ttggatctcg cggtgttccg cgcctggaag     600
ctgcatgacg aactcggcct gaacattgtc atgccggttc ttccgatgca tggtccccgc     660
gggcaaggtc tgccgaaggg cgccgttttt cccggagaag atgttctcga cgatgtgcat     720
```

```
gggacggctc aagcggtgtg ggatatccgg cggctgttgt cctggatacg atcgcaggag    780
gaggagtcgc tgatcgggtt gaacggtctc tcgctgggcg gctacatcgc gtcattggtc    840
gccagcctcg aagaaggtct cgcctgcgcg attctcggtg tcccagtggc tgatctgatc    900
gagttgttgg gccgccactg cggtcttcgg cacaaagacc cccgccgcca caccgtcaag    960
atggccgaac cgatcggccg aatgatctcg ccgctctcac ttacgccact ggtgcccatg   1020
ccgggccgct ttatctacgc gggcattgcc gaccgactcg tgcatccacg cgaacaggtg   1080
actcgcctct gggagcactg ggcaaaccc gaaatcgtgt ggtatccagg cggtcacact   1140
ggcttcttcc agtcgcggcc ggtacgacgg tttgtccagg ctgcgctgga gcagtcgggc   1200
ctgttggacg cgccacggac acagcgcgac cgttccgcct aa                      1242
```

<210> SEQ ID NO 33
<211> LENGTH: 270
<212> TYPE: PRT
<213> ORGANISM: Mycobacterium tuberculosis

<400> SEQUENCE: 33

```
Met Ala Asn Pro Phe Val Lys Ala Trp Lys Tyr Leu Met Ala Leu Phe
1               5                   10                  15

Ser Ser Lys Ile Asp Glu His Ala Asp Pro Lys Val Gln Ile Gln Gln
            20                  25                  30

Ala Ile Glu Glu Ala Gln Arg Thr His Gln Ala Leu Thr Gln Gln Ala
        35                  40                  45

Ala Gln Val Ile Gly Asn Gln Arg Gln Leu Glu Met Arg Leu Asn Arg
    50                  55                  60

Gln Leu Ala Asp Ile Glu Lys Leu Gln Val Asn Val Arg Gln Ala Leu
65                  70                  75                  80

Thr Leu Ala Asp Gln Ala Thr Ala Gly Asp Ala Ala Lys Ala Thr
                85                  90                  95

Glu Tyr Asn Asn Ala Ala Glu Ala Phe Ala Ala Gln Leu Val Thr Ala
            100                 105                 110

Glu Gln Ser Val Glu Asp Leu Lys Thr Leu His Asp Gln Ala Leu Ser
        115                 120                 125

Ala Ala Ala Gln Ala Lys Lys Ala Val Glu Arg Asn Ala Met Val Leu
    130                 135                 140

Gln Gln Lys Ile Ala Glu Arg Thr Lys Leu Leu Ser Gln Leu Glu Gln
145                 150                 155                 160

Ala Lys Met Gln Glu Gln Val Ser Ala Ser Leu Arg Ser Met Ser Glu
                165                 170                 175

Leu Ala Ala Pro Gly Asn Thr Pro Ser Leu Asp Glu Val Arg Asp Lys
            180                 185                 190

Ile Glu Arg Arg Tyr Ala Asn Ala Ile Gly Ser Ala Glu Leu Ala Glu
        195                 200                 205

Ser Ser Val Gln Gly Arg Met Leu Glu Val Gln Ala Gly Ile Gln
    210                 215                 220

Met Ala Gly His Ser Arg Leu Glu Gln Ile Arg Ala Ser Met Arg Gly
225                 230                 235                 240

Glu Ala Leu Pro Ala Gly Gly Thr Thr Ala Thr Pro Arg Pro Ala Thr
                245                 250                 255

Glu Thr Ser Gly Gly Ala Ile Ala Glu Gln Pro Tyr Gly Gln
            260                 265                 270
```

<210> SEQ ID NO 34
<211> LENGTH: 813

-continued

```
<212> TYPE: DNA
<213> ORGANISM: Mycobacterium tuberculosis

<400> SEQUENCE: 34
atggccaatc cgttcgttaa agcctggaag tacctcatgg cgctgttcag ctcgaagatc      60
gacgagcatg ccgaccccaa ggtgcagatt caacaggcca ttgaggaagc acagcgcacc     120
caccaagcgc tgactcaaca ggcggcgcaa gtgatcggta accagcgtca attggagatg     180
cgactcaacc gacagctggc ggacatcgaa aagcttcagg tcaatgtgcg ccaagccctg     240
acgctggccg accaggccac cgccgccgga cgctgccaa ggccaccga atacaacaac       300
gccgccgagg cgttcgcagc ccagctggtg accgccgagc agagcgtcga agacctcaag     360
acgctgcatg accaggcgct tagcgccgca gctcaggcca agaaggccgt cgaacgaaat     420
gcgatggtgc tgcagcagaa gatcgccgag cgaaccaagc tgctcagcca gctcgagcag     480
gcgaagatgc aggagcaggt cagcgcatcg ttgcggtcga tgagtgagct cgccgcgcca     540
ggcaacacgc cgagcctcga cgaggtgcgc gacaagatcg agcgtcgcta cgccaacgcg     600
atcggttcgg ctgaacttgc cgagagttcg gtgcagggcc ggatgctcga ggtggagcag     660
gccgggatcc agatggccgg tcattcacgg ttggaacaga tccgcgcatc gatgcgcggt     720
gaagcgttgc cggccggcgg gaccacggct accccagac cggccaccga acttctggc      780
ggggctattg ccgagcagcc ctacggtcag tag                                   813

<210> SEQ ID NO 35
<211> LENGTH: 3157
<212> TYPE: PRT
<213> ORGANISM: Mycobacterium tuberculosis

<400> SEQUENCE: 35

Met Asn Phe Pro Val Leu Pro Pro Glu Ile Asn Ser Val Leu Met Tyr
  1               5                  10                  15
Ser Gly Ala Gly Ser Ser Pro Leu Leu Ala Ala Ala Ala Trp Asp
             20                  25                  30
Gly Leu Ala Glu Glu Leu Gly Ser Ala Ala Val Ser Phe Gly Gln Val
         35                  40                  45
Thr Ser Gly Leu Thr Ala Gly Val Trp Gln Gly Ala Ala Ala Ala
     50                  55                  60
Met Ala Ala Ala Ala Pro Tyr Ala Gly Trp Leu Gly Ser Val Ala
 65                  70                  75                  80
Ala Gln Ala Val Ala Val Ala Gly Gln Ala Arg Ala Ala Val Ala Ala
                 85                  90                  95
Phe Glu Ala Ala Leu Ala Ala Thr Val Asp Pro Ala Ala Val Ala Val
                100                 105                 110
Asn Arg Met Ala Met Arg Ala Leu Ala Met Ser Asn Leu Leu Gly Gln
            115                 120                 125
Asn Ala Ala Ala Ile Ala Ala Val Glu Ala Glu Tyr Glu Leu Met Trp
        130                 135                 140
Ala Ala Asp Val Ala Ala Met Ala Gly Tyr His Ser Gly Ala Ser Ala
145                 150                 155                 160
Ala Ala Ala Ala Leu Pro Ala Phe Ser Pro Pro Ala Gln Ala Leu Gly
                165                 170                 175
Gly Gly Val Gly Ala Phe Leu Asn Ala Leu Phe Ala Gly Pro Ala Lys
            180                 185                 190
Met Leu Arg Leu Asn Ala Gly Leu Gly Asn Val Gly Asn Tyr Asn Val
        195                 200                 205
```

-continued

```
Gly Leu Gly Asn Val Gly Ile Phe Asn Leu Gly Ala Ala Asn Val Gly
            210                 215                 220

Ala Gln Asn Leu Gly Ala Asn Ala Gly Ser Gly Asn Phe Gly Phe
225                 230                 235                 240

Gly Asn Ile Gly Asn Ala Asn Phe Gly Phe Gly Asn Ser Gly Leu Gly
                245                 250                 255

Leu Pro Pro Gly Met Gly Asn Ile Gly Leu Gly Asn Ala Gly Ser Ser
            260                 265                 270

Asn Tyr Gly Leu Ala Asn Leu Gly Val Gly Asn Ile Gly Phe Ala Asn
        275                 280                 285

Thr Gly Ser Asn Asn Ile Gly Ile Gly Leu Thr Gly Asp Asn Leu Thr
290                 295                 300

Gly Ile Gly Gly Leu Asn Ser Gly Thr Gly Asn Leu Gly Leu Phe Asn
305                 310                 315                 320

Ser Gly Thr Gly Asn Ile Gly Phe Phe Asn Ser Gly Thr Gly Asn Phe
                325                 330                 335

Gly Val Phe Asn Ser Gly Ser Tyr Asn Thr Gly Val Gly Asn Ala Gly
                340                 345                 350

Thr Ala Ser Thr Gly Leu Phe Asn Val Gly Phe Asn Thr Gly Val
            355                 360                 365

Ala Asn Val Gly Ser Tyr Asn Thr Gly Ser Phe Asn Ala Gly Asn Thr
370                 375                 380

Asn Thr Gly Gly Phe Asn Pro Gly Asn Val Asn Thr Gly Trp Leu Asn
385                 390                 395                 400

Thr Gly Asn Thr Asn Thr Gly Ile Ala Asn Ser Gly Asn Val Asn Thr
                405                 410                 415

Gly Ala Phe Ile Ser Gly Asn Phe Ser Asn Gly Val Leu Trp Arg Gly
                420                 425                 430

Asp Tyr Glu Gly Leu Trp Gly Leu Ser Gly Gly Ser Thr Ile Pro Ala
            435                 440                 445

Ile Pro Ile Gly Leu Glu Leu Asn Gly Gly Val Gly Pro Ile Thr Val
        450                 455                 460

Leu Pro Ile Gln Ile Leu Pro Thr Ile Pro Leu Asn Ile His Gln Thr
465                 470                 475                 480

Phe Ser Leu Gly Pro Leu Val Val Pro Asp Ile Val Ile Pro Ala Phe
                485                 490                 495

Gly Gly Gly Thr Ala Ile Pro Ile Ser Val Gly Pro Ile Thr Ile Ser
            500                 505                 510

Pro Ile Thr Leu Phe Pro Ala Gln Asn Phe Asn Thr Thr Phe Pro Val
        515                 520                 525

Gly Pro Phe Phe Gly Leu Gly Val Val Asn Ile Ser Gly Ile Glu Ile
530                 535                 540

Lys Asp Leu Ala Gly Asn Val Thr Leu Gln Leu Gly Asn Leu Asn Ile
545                 550                 555                 560

Asp Thr Arg Ile Asn Gln Ser Phe Pro Val Thr Val Asn Trp Ser Thr
                565                 570                 575

Pro Ala Val Thr Ile Phe Pro Asn Gly Ile Ser Ile Pro Asn Asn Pro
            580                 585                 590

Leu Ala Leu Leu Ala Ser Ala Ser Ile Gly Thr Leu Gly Phe Thr Ile
        595                 600                 605

Pro Gly Phe Thr Ile Pro Ala Ala Pro Leu Pro Leu Thr Ile Asp Ile
610                 615                 620

Asp Gly Gln Ile Asp Gly Phe Ser Thr Pro Pro Ile Thr Ile Asp Arg
625                 630                 635                 640
```

```
Ile Pro Leu Asn Leu Gly Ala Ser Val Thr Val Gly Ile Leu Ile
                645                 650                 655

Asn Gly Val Asn Ile Pro Ala Thr Pro Gly Phe Gly Asn Thr Thr Thr
                660                 665                 670

Ala Pro Ser Ser Gly Phe Phe Asn Ser Gly Asp Gly Val Ser Gly
                675                 680                 685

Phe Gly Asn Phe Gly Ala Gly Ser Ser Gly Trp Trp Asn Gln Ala Gln
                690                 695                 700

Thr Glu Val Ala Gly Ala Gly Ser Gly Phe Ala Asn Phe Gly Ser Leu
705                 710                 715                 720

Gly Ser Gly Val Leu Asn Phe Gly Ser Gly Val Ser Gly Leu Tyr Asn
                725                 730                 735

Thr Gly Gly Leu Pro Pro Gly Thr Pro Ala Val Val Ser Gly Ile Gly
                740                 745                 750

Asn Val Gly Glu Gln Leu Ser Gly Leu Ser Ser Ala Gly Thr Ala Leu
                755                 760                 765

Asn Gln Ser Leu Ile Ile Asn Leu Gly Leu Ala Asp Val Gly Ser Val
                770                 775                 780

Asn Val Gly Phe Gly Asn Val Gly Asp Phe Asn Leu Gly Ala Ala Asn
785                 790                 795                 800

Ile Gly Asp Leu Asn Val Gly Leu Gly Asn Val Gly Gly Gly Asn Val
                805                 810                 815

Gly Phe Gly Asn Ile Gly Asp Ala Asn Phe Gly Leu Gly Asn Ala Gly
                820                 825                 830

Leu Ala Ala Gly Leu Ala Gly Val Gly Asn Ile Gly Leu Gly Asn Ala
                835                 840                 845

Gly Ser Gly Asn Val Gly Phe Gly Asn Met Gly Val Gly Asn Ile Gly
                850                 855                 860

Phe Gly Asn Thr Gly Thr Asn Asn Leu Gly Ile Gly Leu Thr Gly Asp
865                 870                 875                 880

Asn Gln Thr Gly Ile Gly Gly Leu Asn Ser Gly Ala Gly Asn Ile Gly
                885                 890                 895

Leu Phe Asn Ser Gly Thr Gly Asn Val Gly Leu Phe Asn Ser Gly Thr
                900                 905                 910

Gly Asn Phe Gly Leu Phe Asn Ser Gly Ser Phe Asn Thr Gly Ile Gly
                915                 920                 925

Asn Gly Gly Thr Gly Ser Thr Gly Leu Phe Asn Ala Gly Asn Phe Asn
930                 935                 940

Thr Gly Val Ala Asn Pro Gly Ser Tyr Asn Thr Gly Ser Phe Asn Val
945                 950                 955                 960

Gly Asp Thr Asn Thr Gly Gly Phe Asn Pro Gly Ser Ile Asn Thr Gly
                965                 970                 975

Trp Phe Asn Thr Gly Asn Ala Asn Thr Gly Val Ala Asn Ser Gly Asn
                980                 985                 990

Val Asp Thr Gly Ala Leu Met Ser Gly Asn Phe Ser Asn Gly Ile Leu
                995                 1000                1005

Trp Arg Gly Asn Phe Glu Gly Leu Phe Gly Leu Asn Val Gly Ile
        1010                1015                1020

Thr Ile Pro Glu Phe Pro Ile His Trp Thr Ser Thr Gly Gly Ile
        1025                1030                1035

Gly Pro Ile Ile Ile Pro Asp Thr Thr Ile Leu Pro Pro Ile His
        1040                1045                1050

Leu Gly Leu Thr Gly Gln Ala Asn Tyr Gly Phe Ala Val Pro Asp
```

-continued

```
              1055                1060                1065

Ile Pro Ile Pro Ala Ile His Ile Asp Phe Asp Gly Ala Ala Asp
     1070                1075                1080

Ala Gly Phe Thr Ala Pro Ala Thr Thr Leu Leu Ser Ala Leu Gly
     1085                1090                1095

Ile Thr Gly Gln Phe Arg Phe Gly Pro Ile Thr Val Ser Asn Val
     1100                1105                1110

Gln Leu Asn Pro Phe Asn Val Asn Leu Lys Leu Gln Phe Leu His
     1115                1120                1125

Asp Ala Phe Pro Asn Glu Phe Pro Asp Pro Thr Ile Ser Val Gln
     1130                1135                1140

Ile Gln Val Ala Ile Pro Leu Thr Ser Ala Thr Leu Gly Gly Leu
     1145                1150                1155

Ala Leu Pro Leu Gln Gln Thr Ile Asp Ala Ile Glu Leu Pro Ala
     1160                1165                1170

Ile Ser Phe Ser Gln Ser Ile Pro Ile Asp Ile Pro Pro Ile Asp
     1175                1180                1185

Ile Pro Ala Ser Thr Ile Asn Gly Ile Ser Met Ser Glu Val Val
     1190                1195                1200

Pro Ile Asp Val Ser Val Asp Ile Pro Ala Val Thr Ile Thr Gly
     1205                1210                1215

Thr Arg Ile Asp Pro Ile Pro Leu Asn Phe Asp Val Leu Ser Ser
     1220                1225                1230

Ala Gly Pro Ile Asn Ile Ser Ile Ile Asp Ile Pro Ala Leu Pro
     1235                1240                1245

Gly Phe Gly Asn Ser Thr Glu Leu Pro Ser Ser Gly Phe Phe Asn
     1250                1255                1260

Thr Gly Gly Gly Gly Ser Gly Ile Ala Asn Phe Gly Ala Gly
     1265                1270                1275

Val Ser Gly Leu Leu Asn Gln Ala Ser Ser Pro Met Val Gly Thr
     1280                1285                1290

Leu Ser Gly Leu Gly Asn Ala Gly Ser Leu Ala Ser Gly Val Leu
     1295                1300                1305

Asn Ser Gly Val Asp Ile Ser Gly Met Phe Asn Val Ser Thr Leu
     1310                1315                1320

Gly Ser Ala Pro Ala Val Ile Ser Gly Phe Gly Asn Leu Gly Asn
     1325                1330                1335

His Val Ser Gly Val Ser Ile Asp Gly Leu Leu Ala Met Leu Thr
     1340                1345                1350

Ser Gly Gly Ser Gly Gly Ser Gly Gln Pro Ser Ile Ile Asp Ala
     1355                1360                1365

Ala Ile Ala Glu Leu Arg His Leu Asn Pro Leu Asn Ile Val Asn
     1370                1375                1380

Leu Gly Asn Val Gly Ser Tyr Asn Leu Gly Phe Ala Asn Val Gly
     1385                1390                1395

Asp Val Asn Leu Gly Ala Gly Asn Leu Gly Asn Leu Asn Leu Gly
     1400                1405                1410

Gly Gly Asn Leu Gly Gly Gln Asn Leu Gly Leu Gly Asn Leu Gly
     1415                1420                1425

Asp Gly Asn Val Gly Phe Gly Asn Leu Gly His Gly Asn Val Gly
     1430                1435                1440

Phe Gly Asn Ser Gly Leu Gly Ala Leu Pro Gly Ile Gly Asn Ile
     1445                1450                1455
```

-continued

Gly Leu Gly Asn Ala Gly Ser Asn Val Gly Phe Gly Asn Met
1460            1465            1470

Gly Leu Gly Asn Ile Gly Phe Gly Asn Thr Gly Thr Asn Asn Leu
1475            1480            1485

Gly Ile Gly Leu Thr Gly Asp Asn Gln Thr Gly Phe Gly Gly Leu
1490            1495            1500

Asn Ser Gly Ala Gly Asn Leu Gly Leu Phe Asn Ser Gly Thr Gly
1505            1510            1515

Asn Ile Gly Phe Phe Asn Thr Gly Thr Gly Asn Trp Gly Leu Phe
1520            1525            1530

Asn Ser Gly Ser Tyr Asn Thr Gly Ile Gly Asn Ser Gly Thr Gly
1535            1540            1545

Ser Thr Gly Leu Phe Asn Ala Gly Ser Phe Asn Thr Gly Leu Ala
1550            1555            1560

Asn Ala Gly Ser Tyr Asn Thr Gly Ser Leu Asn Ala Gly Asn Thr
1565            1570            1575

Asn Thr Gly Gly Phe Asn Pro Gly Asn Val Asn Thr Gly Trp Phe
1580            1585            1590

Asn Ala Gly His Thr Asn Thr Gly Gly Phe Asn Thr Gly Asn Val
1595            1600            1605

Asn Thr Gly Ala Phe Asn Ser Gly Ser Phe Asn Asn Gly Ala Leu
1610            1615            1620

Trp Thr Gly Asp His His Gly Leu Val Gly Phe Ser Tyr Ser Ile
1625            1630            1635

Glu Ile Thr Gly Ser Thr Leu Val Asp Ile Asn Glu Thr Leu Asn
1640            1645            1650

Leu Gly Pro Val His Ile Asp Gln Ile Asp Ile Pro Gly Met Ser
1655            1660            1665

Leu Phe Asp Ile His Glu Leu Val Asn Ile Gly Pro Phe Arg Ile
1670            1675            1680

Glu Pro Ile Asp Val Pro Ala Val Val Leu Asp Ile His Glu Thr
1685            1690            1695

Met Val Ile Pro Pro Ile Val Phe Leu Pro Ser Met Thr Ile Gly
1700            1705            1710

Gly Gln Thr Tyr Thr Ile Pro Leu Asp Thr Pro Pro Ala Pro Ala
1715            1720            1725

Pro Pro Pro Phe Arg Leu Pro Leu Leu Phe Val Asn Ala Leu Gly
1730            1735            1740

Asp Asn Trp Ile Val Gly Ala Ser Asn Ser Thr Gly Met Ser Gly
1745            1750            1755

Gly Phe Val Thr Ala Pro Thr Gln Gly Ile Leu Ile His Thr Gly
1760            1765            1770

Pro Ser Ser Ala Thr Thr Gly Ser Leu Ala Leu Thr Leu Pro Thr
1775            1780            1785

Val Thr Ile Pro Thr Ile Thr Thr Ser Pro Ile Pro Leu Lys Ile
1790            1795            1800

Asp Val Ser Gly Gly Leu Pro Ala Phe Thr Leu Phe Pro Gly Gly
1805            1810            1815

Leu Asn Ile Pro Gln Asn Ala Ile Pro Leu Thr Ile Asp Ala Ser
1820            1825            1830

Gly Val Leu Asp Pro Ile Thr Ile Phe Pro Gly Gly Phe Thr Ile
1835            1840            1845

Asp Pro Leu Pro Leu Ser Leu Ala Leu Asn Ile Ser Val Pro Asp
1850            1855            1860

```
Ser Ser Val Pro Ile Ile Ile Val Pro Pro Thr Pro Gly Phe Gly
    1865            1870            1875

Asn Ala Thr Ala Thr Pro Ser Ser Gly Phe Phe Asn Ser Gly Ala
    1880            1885            1890

Gly Gly Val Ser Gly Phe Gly Asn Phe Gly Ala Gly Ser Ser Gly
    1895            1900            1905

Trp Trp Asn Gln Ala His Ala Ala Leu Ala Gly Ala Gly Ser Gly
    1910            1915            1920

Val Leu Asn Val Gly Thr Leu Asn Ser Gly Val Leu Asn Val Gly
    1925            1930            1935

Ser Gly Ile Ser Gly Leu Tyr Asn Thr Ala Ile Val Gly Leu Gly
    1940            1945            1950

Thr Pro Ala Leu Val Ser Gly Ala Gly Asn Val Gly Gln Gln Leu
    1955            1960            1965

Ser Gly Val Leu Ala Ala Gly Thr Ala Leu Thr Gln Ser Pro Ile
    1970            1975            1980

Ile Asn Leu Gly Leu Ala Asp Val Gly Asn Tyr Asn Leu Gly Leu
    1985            1990            1995

Gly Asn Val Gly Asp Phe Asn Leu Gly Ala Ala Asn Leu Gly Asp
    2000            2005            2010

Leu Asn Leu Gly Leu Gly Asn Ile Gly Asn Ala Asn Val Gly Phe
    2015            2020            2025

Gly Asn Ile Gly His Gly Asn Val Gly Phe Gly Asn Ser Gly Leu
    2030            2035            2040

Gly Ala Ala Leu Gly Ile Gly Asn Ile Gly Leu Gly Asn Ala Gly
    2045            2050            2055

Ser Thr Asn Val Gly Leu Ala Asn Met Gly Val Gly Asn Ile Gly
    2060            2065            2070

Phe Ala Asn Thr Gly Thr Asn Asn Leu Gly Ile Gly Leu Thr Gly
    2075            2080            2085

Asp Asn Gln Thr Gly Ile Gly Gly Leu Asn Ser Gly Ala Gly Asn
    2090            2095            2100

Ile Gly Leu Phe Asn Ser Gly Thr Gly Asn Ile Gly Phe Phe Asn
    2105            2110            2115

Ser Gly Thr Gly Asn Trp Gly Leu Phe Asn Ser Gly Ser Phe Asn
    2120            2125            2130

Thr Gly Ile Gly Asn Ser Gly Thr Gly Ser Thr Gly Leu Phe Asn
    2135            2140            2145

Ala Gly Gly Phe Thr Thr Gly Leu Ala Asn Ala Gly Ser Tyr Asn
    2150            2155            2160

Thr Gly Ser Phe Asn Val Gly Asp Thr Asn Thr Gly Gly Phe Asn
    2165            2170            2175

Pro Gly Ser Ile Asn Thr Gly Trp Phe Asn Thr Gly Asn Ala Asn
    2180            2185            2190

Thr Gly Ile Ala Asn Ser Gly Asn Val Asp Thr Gly Ala Leu Met
    2195            2200            2205

Ser Gly Asn Phe Ser Asn Gly Ile Leu Trp Arg Gly Asn Tyr Glu
    2210            2215            2220

Gly Leu Phe Ser Tyr Ser Tyr Ser Leu Asp Val Pro Arg Ile Thr
    2225            2230            2235

Ile Leu Asp Ala His Phe Thr Gly Ala Phe Gly Pro Val Val Val
    2240            2245            2250

Pro Pro Ile Pro Val Leu Ala Ile Asn Ala His Leu Thr Gly Asn
```

-continued

```
            2255                2260                2265

Ala Ala Met Gly Ala Phe Thr Ile Pro Gln Ile Asp Ile Pro Ala
2270                2275                2280

Leu Asn Pro Asn Val Thr Gly Ser Val Gly Phe Gly Pro Ile Ala
2285                2290                2295

Val Pro Ser Val Thr Ile Pro Ala Leu Thr Ala Ala Arg Ala Val
2300                2305                2310

Leu Asp Met Ala Ala Ser Val Gly Ala Thr Ser Glu Ile Glu Pro
2315                2320                2325

Phe Ile Val Trp Thr Ser Ser Gly Ala Ile Gly Pro Thr Trp Tyr
2330                2335                2340

Ser Val Gly Arg Ile Tyr Asn Ala Gly Asp Leu Phe Val Gly Gly
2345                2350                2355

Asn Ile Ile Ser Gly Ile Pro Thr Leu Ser Thr Thr Gly Pro Val
2360                2365                2370

His Ala Val Phe Asn Ala Ala Ser Gln Ala Phe Asn Thr Pro Ala
2375                2380                2385

Leu Asn Ile His Gln Ile Pro Leu Gly Phe Gln Val Pro Gly Ser
2390                2395                2400

Ile Asp Ala Ile Thr Leu Phe Pro Gly Gly Leu Thr Phe Pro Ala
2405                2410                2415

Asn Ser Leu Leu Asn Leu Asp Val Phe Val Gly Thr Pro Gly Ala
2420                2425                2430

Thr Ile Pro Ala Ile Thr Phe Pro Glu Ile Pro Ala Asn Ala Asp
2435                2440                2445

Gly Glu Leu Tyr Val Ile Ala Gly Asp Ile Pro Leu Ile Asn Ile
2450                2455                2460

Pro Pro Thr Pro Gly Ile Gly Asn Thr Thr Thr Val Pro Ser Ser
2465                2470                2475

Gly Phe Phe Asn Thr Gly Ala Gly Gly Ser Gly Phe Gly Asn
2480                2485                2490

Phe Gly Ala Asn Met Ser Gly Trp Trp Asn Gln Ala His Thr Ala
2495                2500                2505

Leu Ala Gly Ala Gly Ser Gly Ile Ala Asn Val Gly Thr Leu His
2510                2515                2520

Ser Gly Val Leu Asn Leu Gly Ser Gly Leu Ser Gly Ile Tyr Asn
2525                2530                2535

Thr Ser Thr Leu Pro Leu Gly Thr Pro Ala Leu Val Ser Gly Leu
2540                2545                2550

Gly Asn Val Gly Asp His Leu Ser Gly Leu Leu Ala Ser Asn Val
2555                2560                2565

Gly Gln Asn Pro Ile Thr Ile Val Asn Ile Gly Leu Ala Asn Val
2570                2575                2580

Gly Asn Gly Asn Val Gly Leu Gly Asn Ile Gly Asn Leu Asn Leu
2585                2590                2595

Gly Ala Ala Asn Ile Gly Asp Val Asn Leu Gly Phe Gly Asn Ile
2600                2605                2610

Gly Asp Val Asn Leu Gly Phe Gly Asn Ile Gly Gly Asn Val
2615                2620                2625

Gly Phe Gly Asn Ile Gly Asp Ala Asn Phe Gly Phe Gly Asn Ser
2630                2635                2640

Gly Leu Ala Ala Gly Leu Ala Gly Met Gly Asn Ile Gly Leu Gly
2645                2650                2655
```

-continued

```
Asn Ala Gly Ser Gly Asn Val Gly Trp Ala Asn Met Gly Leu Gly
         2660            2665                2670

Asn Ile Gly Phe Gly Asn Thr Gly Thr Asn Asn Leu Gly Ile Gly
         2675            2680                2685

Leu Thr Gly Asp Asn Gln Ser Gly Ile Gly Gly Leu Asn Ser Gly
         2690            2695                2700

Thr Gly Asn Ile Gly Leu Phe Asn Ser Gly Thr Gly Asn Ile Gly
         2705            2710                2715

Phe Phe Asn Ser Gly Thr Ala Asn Phe Gly Leu Phe Asn Ser Gly
         2720            2725                2730

Ser Tyr Asn Thr Gly Ile Gly Asn Ser Gly Val Ala Ser Thr Gly
         2735            2740                2745

Leu Val Asn Ala Gly Gly Phe Asn Thr Gly Val Ala Asn Ala Gly
         2750            2755                2760

Ser Tyr Asn Thr Gly Ser Phe Asn Ala Gly Asp Thr Asn Thr Gly
         2765            2770                2775

Gly Phe Asn Pro Gly Ser Thr Asn Thr Gly Trp Phe Asn Thr Gly
         2780            2785                2790

Asn Ala Asn Thr Gly Val Ala Asn Ala Gly Asn Val Asn Thr Gly
         2795            2800                2805

Ala Leu Ile Thr Gly Asn Phe Ser Asn Gly Ile Leu Trp Arg Gly
         2810            2815                2820

Asn Tyr Glu Gly Leu Ala Gly Phe Ser Phe Gly Tyr Pro Ile Pro
         2825            2830                2835

Leu Phe Pro Ala Val Gly Ala Asp Val Thr Gly Asp Ile Gly Pro
         2840            2845                2850

Ala Thr Ile Ile Pro Pro Ile His Ile Pro Ser Ile Pro Leu Gly
         2855            2860                2865

Phe Ala Ala Ile Gly His Ile Gly Pro Ile Ser Ile Pro Asn Ile
         2870            2875                2880

Ala Ile Pro Ser Ile His Leu Gly Ile Asp Pro Thr Phe Asp Val
         2885            2890                2895

Gly Pro Ile Thr Val Asp Pro Ile Thr Leu Thr Ile Pro Gly Leu
         2900            2905                2910

Ser Leu Asp Ala Ala Val Ser Glu Ile Arg Met Thr Ser Gly Ser
         2915            2920                2925

Ser Ser Gly Phe Lys Val Arg Pro Ser Phe Ser Phe Phe Ala Val
         2930            2935                2940

Gly Pro Asp Gly Met Pro Gly Gly Glu Val Ser Ile Leu Gln Pro
         2945            2950                2955

Phe Thr Val Ala Pro Ile Asn Leu Asn Pro Thr Thr Leu His Phe
         2960            2965                2970

Pro Gly Phe Thr Ile Pro Thr Gly Pro Ile His Ile Gly Leu Pro
         2975            2980                2985

Leu Ser Leu Thr Ile Pro Gly Phe Thr Ile Pro Gly Gly Thr Leu
         2990            2995                3000

Ile Pro Gln Leu Pro Leu Gly Leu Gly Leu Ser Gly Gly Thr Pro
         3005            3010                3015

Pro Phe Asp Leu Pro Thr Val Val Ile Asp Arg Ile Pro Val Glu
         3020            3025                3030

Leu His Ala Ser Thr Thr Ile Gly Pro Val Ser Leu Pro Ile Phe
         3035            3040                3045

Gly Phe Gly Gly Ala Pro Gly Phe Gly Asn Asp Thr Thr Ala Pro
         3050            3055                3060
```

| Ser | Ser | Gly | Phe | Phe | Asn | Thr | Gly | Gly | Gly | Gly | Ser | Gly | Phe |
|---|---|---|---|---|---|---|---|---|---|---|---|---|---|
| 3065 | | | | | 3070 | | | | | 3075 | | | |
| Ser | Asn | Ser | Gly | Ser | Gly | Met | Ser | Gly | Val | Leu | Asn | Ala | Ile | Ser |
| 3080 | | | | | 3085 | | | | | 3090 | | | | |
| Asp | Pro | Leu | Leu | Gly | Ser | Ala | Ser | Gly | Phe | Ala | Asn | Phe | Gly | Thr |
| 3095 | | | | | 3100 | | | | | 3105 | | | | |
| Gln | Leu | Ser | Gly | Ile | Leu | Asn | Arg | Gly | Ala | Gly | Ile | Ser | Gly | Val |
| 3110 | | | | | 3115 | | | | | 3120 | | | | |
| Tyr | Asn | Thr | Gly | Thr | Leu | Gly | Leu | Val | Thr | Ser | Ala | Phe | Val | Ser |
| 3125 | | | | | 3130 | | | | | 3135 | | | | |
| Gly | Phe | Met | Asn | Val | Gly | Gln | Gln | Leu | Ser | Gly | Leu | Leu | Phe | Ala |
| 3140 | | | | | 3145 | | | | | 3150 | | | | |
| Gly | Thr | Gly | Pro |
| 3155 | | | |

<210> SEQ ID NO 36
<211> LENGTH: 9474
<212> TYPE: DNA
<213> ORGANISM: Mycobacterium tuberculosis

<400> SEQUENCE: 36

```
ttgaattttc cagttctgcc accggaaatc aactccgtgc tgatgtattc gggtgcgggg      60
tcgagcccgt tgctggcggc ggccgcggcg tgggatgggc tggctgagga gttggggtcg     120
gcggcggtgt cgtttgggca ggtgacgtcg ggcctgacgg cggggggtgtg gcagggtgcg   180
gcggcggcgg cgatggcggc cgcggcggcc ccgtatgcgg ggtggttggg ttcggtggcg     240
gcgcaggccg tggcggtggc cgggcaggcg cgggccgcgg tggcggcgtt tgaggcggcg     300
ttggcggcga cggtggatcc ggcggcggtg gcggtcaacc ggatggcgat gcgggcgttg     360
gcgatgtcga acctgctggg gcagaacgcc gcagcgatcg cggccgtcga ggccgagtac     420
gagttgatgt gggccgccga tgtggcggcg atggccggct accattccgg cgcgtcggct     480
gctgccgcgg cgttgccggc gttcagccca ccgcgcagg cgttgggggg tggtgtcggc      540
gcgttcctca atgctctatt tgccggaccc gcgaagatgt tgaggcttaa cgcgggcttg     600
ggcaatgtcg gtaattacaa cgtcgggttg gcaatgtcg ggatattcaa cctgggcgca     660
gccaatgtcg gtgcgcagaa tttgggtgct gccaacgccg gtagcgggaa tttcggtttc     720
ggcaatatcg gcaacgccaa cttcgggttc ggcaactcgg gtcttgggtt gccgccgggc     780
atgggcaata ttgggttggg caatgcgggc agcagcaact acggcctcgc aaacctgggt     840
gtgggcaaca tcggttttgc caacacgggt agcaacaaca tcgggatcgg gttgaccggg     900
gacaacctga ctggcattgg gggcctgaat tcaggaaccg gtaatctggg gttgttcaac     960
tccggcaccg gcaacattgg gttcttcaat tcggggaccg gcaacttcgg ggtattcaac    1020
tcgggcagct acaacaccgg tgtcggtaat gcggggacgg ccagtaccgg gttgttcaac    1080
gttggtgggt caacacgggg tgtggccaac gtgggtagct ataacacggg cagcttcaac    1140
gcgggcaaca ccaatacggg tggcttcaac ccgggcaacg tcaacaccgg ctggctgaac    1200
accggcaaca ccaacaccgg catcgccaac tcgggcaatg tcaacaccgg cgcgttcatc    1260
tcgggcaact cagcaacggt gtgctgtgg cggggtgact acgagggcct gtgggggctc    1320
tccggtggat cgaccattcc ggcgatcccc attggtctcg agctcaacgg cggcgtcggc    1380
cccatcaccg tgttgccgat ccagattttg cccaccatcc cgctcaacat tcaccaaacc    1440
ttcagcctcg gcccgctggt cgttccggac atcgtgatcc ccgcttttgg tggcggtacg    1500
```

```
gccatacccta tcagcgtcgg ccccatcacc atctcgccca tcaccctgtt cccggctcag    1560
aacttcaaca cgactttccc cgtcggcccc ttctttggct tgggggtcgt caacatttca    1620
ggaatcgaaa tcaaagatct tgccggcaac gtcaccctcc aattaggtaa ccttaatatc    1680
gacaccagaa ttaaccagtc attcccggtg accgtcaact ggagtacccc ggcagtaacg    1740
atcttcccga atggcatcag tattcccaac aatccactgg cgctgctggc cagcgcgtcg    1800
atcggcacgc tgggattcac gatcccgggc ttcaccattc ccgctgcgcc gctgccgctg    1860
acgatcgaca tagacggcca gattgacggc ttcagcaccc cgccgatcac gatcgaccgc    1920
atcccgctga acctcggcgc cagcgtcact gtcggcccta tcctgatcaa cggcgttaat    1980
atcccggcga ccccgggctt tggcaacacg accaccgctc cgtcgtcggg tttcttcaac    2040
tccggcgacg gtggggtgtc gggcttcggg aatttcggtg cgggcagctc gggttggtgg    2100
aaccaggcgc agaccgaggt ggctggggcg ggttcgggtt tcgccaattt cggttcgctg    2160
ggatcgggtg tgctgaactt cggctcgggt gtgtcggggc tgtacaacac cggcgggttg    2220
ccgccgggga ccccggcggt ggtctcgggc atcggcaatg ttggtgagca gctgtcgggg    2280
ttgtcctcgg cggggacggc actcaaccag agcctcatca tcaatctcgg gttggccgat    2340
gtgggcagcg taaacgtcgg tttcggcaac gtcgggact tcaacctggg tgcggccaat    2400
atcggcgact tgaacgtggg tttgggcaat gtcggcggcg gcaacgtcgg gttcggcaat    2460
atcggcgatg ccaacttcgg gttgggcaat gcgggtctgg cggcgggcct ggccggggtg    2520
ggcaacatcg ggttgggcaa tgccggcagc ggcaacgtcg gcttcggcaa catgggtgtg    2580
ggcaacatcg ggttcggtaa caccggcacc aacaacctcg ggattgggct gaccggggac    2640
aaccagactg ggatcggcgg cttgaactcc ggtgccggca acatcgggtt gttcaactcc    2700
ggcaccggca acgtcgggtt gttcaactcc gggaccggga acttcgggtt gttcaactcg    2760
ggcagcttca acaccggcat cggcaatggc ggaacgggca gtactgggct tttcaatgcc    2820
ggtaatttca ataccggtgt ggccaaccct gggtcgtaca acacgggcag cttcaatgtg    2880
ggtgacacca acaccggtgg tttcaacccg ggcagcatca acaccggctg gttcaacacc    2940
ggcaacgcca acaccggcgt cgccaattcg ggcaatgtcg acaccggcgc cctcatgtcg    3000
ggcaacttca gcaacggcat cttgtggcga ggcaacttcg agggcctgtt cggcctgaac    3060
gtcggcatca cgattcccga attcccgatc cactggactt caaccggcgg catcggcccc    3120
attatcatcc cggacaccac gatccttccc cccatccacc tgggcctcac gggacaagcg    3180
aactacggct tcgccgtgcc ggacatcccc attccggcaa tccacatcga cttcgacggt    3240
gccgccgacg ccggcttcac cgccccggcc accaccctgc tttctgcgct gggcattacc    3300
ggacaattca ggttcggccc gatcaccgtc tcaaacgtcc agctcaatcc gttcaacgtt    3360
aacctcaagc ttcagttcct ccacgacgcg ttcccaaatg aatttcccga tcccacaatc    3420
tcggttcaga tacaggtcgc catacccctt acttcggcaa cgctgggcgg attggccctg    3480
ccgctgcagc agaccatcga cgccatcgaa ttgccggcaa tctcgttcag ccaatccata    3540
cccatcgaca ttccgccgat cgacatcccg gcctccacta tcaacggaat ttcgatgtcg    3600
gaggtcgtgc cgatcgatgt gtccgtcgac attccggcgg tcaccatcac cggcaccagg    3660
atcgacccga ttccgctgaa cttcgacgtt ctcagcagcg ccggacccat caacatctcg    3720
atcatcgaca ttcggcgct gccgggcttt ggcaactcga ccgagctgcc gtcgtcgggc    3780
ttcttcaaca ccggcggcgg tggcggctcg ggcatcgcca acttcggcgc ggggtgtcc    3840 ggcttgctga accaggcctc gagtccgatg gtggggacgc tctccggcct gggcaatgcc    3900
```

```
ggcagcctgg catccggtgt gctgaactcc ggcgtcgaca tctcgggcat gttcaacgtg    3960
agcacgctgg gctccgcgcc ggcggtgatc tcgggtttcg gcaacctggg caaccacgtg    4020 tcggggtgt ccatcgatgg cctgctggcg atgctgacca gcggcgggtc gggcggctcc    4080
gggcagccga gcatcatcga cgcggcgatc gccgagctgc ggcacctgaa tccgctgaac    4140
atcgtcaacc tgggcaacgt cggcagctac aacctcggct tcgccaacgt cggcgacgtc    4200
aacctgggcg cgggcaacct cggcaacctc aacctcggcg tggcaacct cggcgggcag    4260 aacctggggt tgggcaacct cggggacggc aacgtcgggt tcggcaacct cggccacggc    4320
aatgtcgggt tcggcaactc gggcctgggg gcgctgccgg ggatcggcaa catcgggttg    4380
ggcaacgccg gcagcaacaa cgtcggcttc ggcaacatgg gcctgggcaa catcgggttc    4440
ggcaataccg gcaccaacaa cctcgggatc gggctgaccg gcgacaacca gaccgggttc    4500
ggcggcctga actccggtgc cggcaacctg gggttgttca actccggcac cggcaacatc    4560
gggttcttca acaccgggac cggaaactgg gggttgttca actcgggcag ctacaacacc    4620
ggcatcggta acagcggaac gggcagtacc gggcttttca atgccgggag tttcaacacg    4680
ggtctggcca atgccggtag ttacaacacc ggcagcctca acgcgggcaa caccaacacc    4740
ggcggcttca accctggcaa tgtcaacacc ggctggttca acgccggcca caccaacacc    4800
ggcggcttca acacgggcaa tgtcaacacc ggcgcgttca actccggcag cttcaacaac    4860
ggcgcgctgt ggaccggtga tcaccacggg ctggtcggct tctcctacag catcgaaatc    4920
accggcagca ccctggtgga catcaacgaa accctcaacc tcggtcccgt ccacatcgat    4980
cagatcgata ttcccggcat gtcgctgttc gacatccacg aactcgtcaa catcgggccc    5040
ttcaggatcg agcccatcga tgtccccgca gtggtgctgg acatccacga acgatggtc     5100 atcccgccca tcgtcttcct gccgagcatg acgatcggcg gtcagaccta cacgattccg    5160
ctcgacacgc cccggccc cgccccgccg cccttcagac ttccgttgct gttcgtgaat      5220
gcgctcggcg acaactggat cgttggggcg tccaactcaa ccggaatgag tggtggcttt    5280
gtcaccgcac ccactcaggg catcctgatc cataccggtc ccagcagcgc aaccaccggt    5340
agcctcgcac taaccctccc aaccgtcacc atcccaacga tcacgacatc gcctatcccg    5400
ctcaagatcg atgtgtcggg cggtcttccg gccttcacgc tgttcccgg tggcctcaac     5460 atcccgcaaa atgcgatccc gttgaccatc gatgcgtccg gcgtgctgga tccgatcacg    5520
atattcccgg gtggtttcac gatcgatccg ctgccactga gcctggccct caacatcagc    5580
gtgccggaca gcagcgttcc gatcatcatc gttccgccga cgcccggctt cgggaacgcg    5640
accgccaccc cgtcgtcggg tttcttcaac tccggcgcgg gcggggtgtc gggtttcggc    5700
aacttcgggg ccggcagctc aggctggtgg aaccaggcgc atgccgcgtt ggcgggcgcg    5760
ggctcgggcg ttctcaacgt tggcacgctg aactcgggtg tgctgaacgt cggctcgggg    5820
atatcggggc tgtacaacac cgctatcgtg gtttgggga cgccgcgct ggtgtcgggt      5880 gccggcaacg tgggccagca gctgtcgggg gtgttggcgg ccgggacggc gttgacccaa    5940
agccccatca tcaacctcgg gttggccgat gtcggcaact acaacctcgg gttgggcaac    6000
gttggggact tcaacctggg cgcggccaac ctcggcgacc tcaacctagg gttgggcaat    6060
atcgggaacg ccaacgtcgg cttcggcaat atcggccacg caacgtcgg gtttggcaat    6120 tcgggcctgg gggcggcgct cggcatcggc aatatcgggt tgggcaatgc gggcagcacc    6180
aacgttggcc tggccaacat gggtgtgggc aacatcgggt tcgccaacac cggcaccaac    6240
aacctcggga ttgggctgac cggcgacaac cagaccggca tcggcggctt gaactccggt    6300
```

```
gccggcaaca ttggcctgtt caactccggc accggcaaca tcgggttctt caactccggg    6360
accggaaact gggggttgtt caactcgggc agcttcaaca ccggcatcgg taatagcgga    6420
acgggcagta ctgggctttt caatgccggt ggtttcacta cgggtctggc caacgccggg    6480
tcgtacaaca cgggcagctt caatgtcggt gacaccaaca ccggtggctt caacccgggc    6540
agcatcaaca ccggctggtt caacaccggt aacgccaaca ccggcatcgc gaactcgggc    6600
aatgtcgaca ccggcgccct catgtcgggc aacttcagca acggcatcct gtggcgggc    6660 aactacgaag gcctattcag ctattcctac agcctcgacg ttccccggat caccatcctg    6720
gacgcgcatt tcaccggggc cttcggcccg gtggtcgtcc cgcccatccc ggttctggcg    6780
atcaacgcgc acctgaccgg caacgcggcg atgggcgcct tcaccatccc gcaaatcgat    6840
attcccgccc tcaatccgaa cgtcaccgga agcgtcggct tcggcccat cgcggtcccc    6900 tcggtcacca ttcccgccct gaccgccgca cgagcggtcc tcgatatggc cgcgtcggtc    6960
ggggcgacca gcgaaataga gccgtttatc gtctggacgt catccggtgc gatcggccca    7020
acgtggtact cggtcggcag aatctacaac gccggtgacc tgttcgtcgg cggcaatatc    7080
atctcgggaa tcccgacgct cagcacgacc ggcccggtgc atgccgtctt caatgcggca    7140
tctcaggcgt tcaacacccc ggcgctcaat attcaccaga tcccgttggg tttccaggtg    7200
ccgggcagca tcgacgcgat caccctgttc cccggtggtc tgacgttccc ggcgaactcg    7260
ctgctgaacc tggatgtgtt cgtcggcacc cccggcgcca ccattccggc gatcacgttc    7320
ccggagatcc cggcgaacgc cgacggcgaa ctctacgtca tcgccggcga catcccgctg    7380
atcaacatcc cgcccacccc gggcattggg aacaccacca ccgttccgtc gtcgggcttc    7440
ttcaacaccg gggcgggcgg gggctcgggt ttcggcaact tcggcgcgaa catgtcgggg    7500
tggtggaacc aggcgcacac cgctttggca ggcgcgggtt cgggtattgc caacgtcggc    7560
acactgcact ccggcgtgct caacctcggt tcggggctgt cggggatcta caacaccagc    7620
acgctgccgc ttgggacgcc ggcgttggtg tcgggcctgg gcaacgtcgg tgatcacctg    7680
tcgggcttgt tggcctccaa cgtggggcaa aaccccatca ccatcgtcaa catcgggttg    7740
gctaacgtcg gcaacggcaa cgtcggcctc ggcaacatcg gcaacctcaa cctgggtgcg    7800
gccaacattg gcgacgtgaa cctgggattc ggcaacattg gcgacgtgaa cctgggcttc    7860
ggcaacatcg gcgcggcaa cgtcgggttc ggcaatatcg gcgatgccaa cttcgggttc    7920
gggaattcgg gtctggcggc gggcctggcc ggcatgggca atatcgggct gggcaacgcc    7980
ggcagcggca acgtcggctg ggccaacatg ggcctgggca acatcgggtt tggcaacacc    8040
ggcaccaaca acctcgggat cgggctcacc ggcgacaacc agtccggcat cggcggcttg    8100
aactccggca ctggcaacat tggcctgttc aactccggca caggcaatat cggcttcttc    8160
aactccggga ctgccaactt cgggttgttc aactccggca gctacaacac cggtatcggc    8220
aactccgggg tggccagcac cggggttgtc aacgccggcg gcttcaacac cggtgtggca    8280
aacgccgggt cgtacaacac gggcagcttc aatgctggtg acaccaacac cggtggcttc    8340
aacccaggca gcaccaacac cggctggttc aacaccggta acgccaacac cggcgtcgcc    8400
aacgcgggca atgtcaacac cggcgccctc atcacgggca ctttagcaa cggcatctta    8460 tggcggggca attacgaggg cttggccggc ttctcccttcg ggtaccccat tccgctgttc    8520
cccgcggtgg gcgccgacgt caccggcgac atcgcccccg ccaccatcat tccgcccatc    8580
cacatcccgt ccatcccgtt gggcttcgcc gcgatcggcc acatcgggcc gatcagcatc    8640
ccgaacatcg ccatcccctc gatccacctg ggcatcgatc ccaccttcga cgtcggccct    8700
```

```
atcaccgtgg acccatcac cctcaccatc cctggcctaa gtttggatgc tgccgtctcg   8760
gagatcagga tgacgtccgg aagcagctcc ggattcaagg tcagacccag cttttcattc   8820
ttcgcggtcg gacccgacgg catgcccggg ggcgaggtct ccatacttca accattcacc   8880
gtggcaccca tcaacttgaa cccgacgaca ctgcacttcc ccggattcac cattcccacc   8940
ggacccatcc acatcggcct gccgctgtcg ctgaccattc cgggcttcac catcccgggc   9000
ggcaccctga ttccccaact cccgctgggc ctcggtttgt ccggcggcac ccaccctttt   9060
gatctcccga cggtcgttat cgaccggatc ccggtggagt acacgccag caccaccatc   9120
ggccccgtca gcctcccgat tttcgggttc ggcggagcac cgggctttgg caacgacacc   9180
accgcgccgt cgtcgggctt cttcaacacc ggcggtggtg gcgggtccgg cttctccaac   9240
tccgggtcgg gcatgtcggg ggtgctcaac gcgatctcgg atccgctgct cgggtcggcg   9300
tcgggcttcg ccaatttcgg cacccagctc tccggcatcc tcaaccgtgg cgcgggcatc   9360
tcgggcgtgt acaacacggg cacgcttggc ctggtcacat cggccttcgt ctcgggcttt   9420
atgaacgtcg gccagcagct gtcgggcctg ctgttcgcgg gcaccgggcc gtaa         9474
```

<210> SEQ ID NO 37
<211> LENGTH: 526
<212> TYPE: PRT
<213> ORGANISM: Mycobacterium tuberculosis

<400> SEQUENCE: 37

```
Met Pro Asp Gln Asp Thr Lys Val Arg Phe Phe Arg Val Phe Cys Trp
 1               5                  10                  15

Cys Pro Val Leu Arg Met Val Arg Ile Met Leu Met His Ala Val Arg
                20                  25                  30

Ala Trp Arg Ser Ala Asp Asp Phe Pro Cys Thr Glu His Met Ala Tyr
            35                  40                  45

Lys Ile Ala Gln Val Ala Ala Asp Pro Val Asp Val Asp Pro Glu Val
        50                  55                  60

Ala Asp Met Val Cys Asn Arg Ile Ile Asp Asn Ala Ala Val Ser Ala
65                  70                  75                  80

Ala Ser Met Val Arg Arg Pro Val Thr Val Ala Arg His Gln Ala Leu
                85                  90                  95

Ala His Pro Val Arg His Gly Ala Lys Val Phe Gly Val Glu Gly Ser
            100                 105                 110

Tyr Ser Ala Asp Trp Ala Ala Trp Ala Asn Gly Val Ala Ala Arg Glu
        115                 120                 125

Leu Asp Phe His Asp Thr Phe Leu Ala Ala Asp Tyr Ser His Pro Ala
    130                 135                 140

Asp Asn Ile Pro Pro Leu Val Ala Val Ala Gln Gln Leu Gly Val Cys
145                 150                 155                 160

Gly Ala Glu Leu Ile Arg Gly Leu Val Thr Ala Tyr Glu Ile His Ile
                165                 170                 175

Asp Leu Thr Arg Gly Ile Cys Leu His Glu His Lys Ile Asp His Val
            180                 185                 190

Ala His Leu Gly Pro Ala Val Ala Ala Gly Ile Gly Thr Met Leu Arg
        195                 200                 205

Leu Asp Gln Glu Thr Ile Tyr His Ala Ile Gly Gln Ala Leu His Leu
    210                 215                 220

Thr Thr Ser Thr Arg Gln Ser Arg Lys Gly Ala Ile Ser Ser Trp Lys
225                 230                 235                 240

Ala Phe Ala Pro Ala His Ala Gly Lys Val Gly Ile Glu Ala Val Asp
```

```
                  245                 250                 255
Arg Ala Met Arg Gly Glu Gly Ser Pro Ala Pro Ile Trp Glu Gly Glu
            260                 265                 270

Asp Gly Val Ile Ala Trp Leu Leu Ala Gly Pro Glu His Thr Tyr Arg
            275                 280                 285

Val Pro Leu Pro Ala Pro Gly Glu Pro Lys Arg Ala Ile Leu Asp Ser
            290                 295                 300

Tyr Thr Lys Gln His Ser Ala Glu Tyr Gln Ser Gln Ala Pro Ile Asp
305                 310                 315                 320

Leu Ala Cys Arg Leu Arg Glu Arg Ile Gly Asp Leu Asp Gln Ile Ala
                325                 330                 335

Ser Ile Val Leu His Thr Ser His Thr His Val Val Ile Gly Thr
                340                 345                 350

Gly Ser Gly Asp Pro Gln Lys Phe Asp Pro Asp Ala Ser Arg Glu Thr
            355                 360                 365

Leu Asp His Ser Leu Pro Tyr Ile Phe Ala Val Ala Leu Gln Asp Gly
            370                 375                 380

Cys Trp His His Glu Arg Ser Tyr Ala Pro Glu Arg Ala Arg Arg Ser
385                 390                 395                 400

Asp Thr Val Ala Leu Trp His Lys Ile Ser Thr Val Glu Asp Pro Glu
                405                 410                 415

Trp Thr Arg Arg Tyr His Cys Ala Asp Pro Ala Lys Lys Ala Phe Gly
                420                 425                 430

Ala Arg Ala Glu Val Thr Leu His Ser Gly Val Ile Val Asp Glu
                435                 440                 445

Leu Ala Val Ala Asp Ala His Pro Leu Gly Thr Arg Pro Phe Glu Arg
450                 455                 460

Lys Gln Tyr Val Glu Lys Phe Thr Glu Leu Ala Asp Gly Val Val Glu
465                 470                 475                 480

Pro Val Glu Gln Gln Arg Phe Leu Ala Val Val Glu Ser Leu Ala Asp
                485                 490                 495

Leu Glu Ser Gly Ala Val Gly Gly Leu Asn Val Leu Val Asp Pro Arg
            500                 505                 510

Val Leu Asp Lys Ala Pro Val Ile Pro Pro Gly Ile Phe Arg
515                 520                 525

<210> SEQ ID NO 38
<211> LENGTH: 1581
<212> TYPE: DNA
<213> ORGANISM: Mycobacterium tuberculosis

<400> SEQUENCE: 38
gtgccggatc aggacacaaa agtacgcttt ttcagggtct tttgttggtg tcctgtgctg      60
cgtatggtgc ggattatgtt gatgcatgcg gtccgggcgt ggcgcagcgc cgacgatttc     120
ccgtgcaccg agcacatggc ctacaagatc gcccaggtgc tgccgatccc ggttgacgtc     180
gacccggagg tagcggacat ggtgtgcaac cgcatcatcg acaacgctgc ggtgagcgcc     240
gcatcaatgg tgcgcagacc ggtcaccgtg gcccgccacc aggcactggc catccggtg      300 cgacacgggg cgaaggtatt tggcgtcgag ggcagctact cggcggactg ggcggcctgg     360
gccaacggcg tcgccgcgcg tgaacttgac tttcacgaca cgtttctggc cgccgactat     420
tcgcacccgg cggacaacat accccccactg gtggcggtcg cccagcagct cggcgtgtgc     480
ggcgcggagc tgatccgcgg tctggtaacc gcctatgaga tccacatcga cctaacccgc     540
ggaatctgct tgcacgagca caagatcgac catgtcgccc acctgggccc ggcggtggcc     600
```

```
gccggcatcg ggaccatgct gcggctcgac caagagacca tctaccacgc gatcggccag       660
gccctgcatc tgaccaccag cacccgtcaa tcccgcaagg gcgccatctc cagctggaag       720
gcgttcgcgc cggcgcatgc cggcaaggtc ggcatcgagg cggtcgatcg ggcgatgcgc       780
ggcgagggct caccggctcc gatctgggag ggcgaggacg gggtgatcgc ctggctgctg       840
gccggacccg agcacaccta ccgggtgccg ttgcccgcac ctggtgaacc caagcgcgcc       900
attctggaca gctacaccaa gcaacactcc gcggagtacc agagccaggc gccgatcgac       960
ctggcctgcc ggctacgtga gcgtatcggc gatctcgacc agatcgcgtc gatcgtgctg      1020
cacaccagcc accacaccca tgtagtgatc ggaacgggat ccggcgatcc gcagaagttc      1080
gacccggacg cgtcacgcga aaccctcgac cactcgctgc cctacatctt cgccgtggca      1140
ctgcaggacg gctgctggca ccacgagcgc tcctacgcgc ccgagcgggc gcgccgttcc      1200
gacacggtgg cactgtggca caagatttcc accgtcgagg atcccgagtg acccgccgc       1260 tatcactgcg ccgatccggc caaaaggcg ttcggggcgc gcgcggaggt gacgctgcac       1320
agcggtgaag tgatcgtgga cgaactggcg gtggccgacg cccatccgct gggcacccgg      1380
ccgttcgagc gcaagcagta cgtagagaag ttcaccgagc tcgccgatgg tgtagtggaa      1440
cccgttgaac agcaacggtt cctggccgta gtagagagtc tcgccgatct cgagagcggt      1500
gccgtgggtg ggctgaacgt gttggtcgat ccgcgggtgc tggacaaagc gccggtgatt      1560
ccaccaggaa tctttcgatg a                                                1581
```

<210> SEQ ID NO 39
<211> LENGTH: 100
<212> TYPE: PRT
<213> ORGANISM: Mycobacterium tuberculosis

<400> SEQUENCE: 39

```
Met Ser Phe Val Thr Thr Arg Pro Asp Ser Ile Gly Glu Thr Ala Ala
1               5                   10                  15

Asn Leu His Glu Ile Gly Val Thr Met Ser Ala His Asp Asp Gly Val
            20                  25                  30

Thr Pro Leu Ile Thr Asn Val Glu Ser Pro Ala His Asp Leu Val Ser
        35                  40                  45

Ile Val Thr Ser Met Leu Phe Ser Met His Gly Glu Leu Tyr Lys Ala
    50                  55                  60

Ile Ala Arg Gln Ala His Val Ile His Glu Ser Phe Val Gln Thr Leu
65                  70                  75                  80

Gln Thr Ser Lys Thr Ser Tyr Trp Leu Thr Glu Leu Ala Asn Arg Ala
                85                  90                  95

Gly Thr Ser Thr
            100
```

<210> SEQ ID NO 40
<211> LENGTH: 303
<212> TYPE: DNA
<213> ORGANISM: Mycobacterium tuberculosis

<400> SEQUENCE: 40

```
gtgtcttttg tcaccacacg gcccgattcg attggggaaa cggccgccaa cctccacgag        60
atcggggtga cgatgagcgc ccatgatgac ggggtcacgc cgctgatcac caatgtggaa       120
tcccccgccc acgatcttgt gtccatcgtg acgtcgatgc tgttttccat gcacggcgag       180
```

```
ctgtacaagg cgatcgcgcg ccaggcccat gtgatccacg agtcatttgt ccaaacactt    240
cagaccagca agacttcgta ttggctcacc gaattagcca accgcgcggg cacctccacc    300
tag                                                                  303
```